United States Patent
Shanks et al.

(10) Patent No.: US 11,529,389 B2
(45) Date of Patent: Dec. 20, 2022

(54) DELIVERING BIOLOGICAL DRUGS TO TISSUES

(71) Applicant: University of Pittsburgh—Of the Commonwealth System of Higher Education, Pittsburgh, PA (US)

(72) Inventors: Robert Michael Queen Shanks, Pittsburgh, PA (US); Jes K. Klarlund, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 126 days.

(21) Appl. No.: 16/979,143

(22) PCT Filed: Mar. 11, 2019

(86) PCT No.: PCT/US2019/021639
§ 371 (c)(1),
(2) Date: Sep. 8, 2020

(87) PCT Pub. No.: WO2019/173829
PCT Pub. Date: Sep. 12, 2019

(65) Prior Publication Data
US 2020/0405805 A1    Dec. 31, 2020

Related U.S. Application Data

(60) Provisional application No. 62/640,859, filed on Mar. 9, 2018.

(51) Int. Cl.
| *A61K 38/00* | (2006.01) |
| *A61K 38/16* | (2006.01) |
| *A61P 29/00* | (2006.01) |
| *A61K 9/06* | (2006.01) |
| *C07K 16/22* | (2006.01) |
| *C07K 16/24* | (2006.01) |

(52) U.S. Cl.
CPC .............. *A61K 38/16* (2013.01); *A61K 9/06* (2013.01); *A61P 29/00* (2018.01); *C07K 16/22* (2013.01); *C07K 16/241* (2013.01); *C07K 16/243* (2013.01); *C07K 16/245* (2013.01); *C07K 16/247* (2013.01); *C07K 16/248* (2013.01); *C07K 16/249* (2013.01); *C07K 2319/70* (2013.01)

(58) Field of Classification Search
CPC ................................ A61K 38/16; A61K 38/12
See application file for complete search history.

(56) References Cited

U.S. PATENT DOCUMENTS

| 9,109,031 B2 | 8/2015 | Dimech et al. |
| 9,187,517 B2 | 11/2015 | Lee |
| 9,309,313 B2* | 4/2016 | Dana .................. A61K 39/3955 |
| 2004/0224010 A1 | 11/2004 | Hofland et al. |
| 2005/0027110 A1* | 2/2005 | Russell .................. A61K 47/64 530/397 |
| 2011/0104236 A1 | 5/2011 | Dana et al. |
| 2012/0207754 A1 | 8/2012 | Giacalone et al. |
| 2016/0031980 A1 | 2/2016 | Schurph et al. |
| 2016/0101161 A1 | 4/2016 | Moss |
| 2017/0152323 A1* | 6/2017 | Chang ................ A61K 31/4745 |

FOREIGN PATENT DOCUMENTS

| JP | 2014-506893 | 3/2014 |
| JP | 2015-522590 | 8/2015 |
| JP | 2016-500323 | 1/2016 |
| JP | 2016-053039 | 4/2016 |
| WO | WO 2000/06195 | 2/2000 |
| WO | WO 2005/093494 A2 | 2/2005 |
| WO | WO 2013/090770 A2 | 6/2013 |
| WO | WO 2013/169609 A1 | 11/2013 |
| WO | WO 2014/004465 A1 | 1/2014 |
| WO | WO 2014/089267 A1 | 6/2014 |
| WO | WO 2014/096028 A1 | 6/2014 |
| WO | WO 2015/065987 A1 | 5/2015 |
| WO | WO 2016/178996 A1 | 11/2016 |
| WO | WO 2018/057522 A1 | 3/2018 |

OTHER PUBLICATIONS

Fischer et al., "Characterization of glycoconjugates of human gastrointestinal mucosa by lectins. I. Histochemical distribution of lectin binding sites in normal alimentary tract as well as in benign and malignant gastric neoplasms," *Journal of Histochemistry & Cytochemistry* 32(7): 681-689 (Dec. 31, 1984).

Grabulovski et al., "A novel, non-immunogenic Fyn SH3-derived binding protein with tumor vascular targeting properties," *Journal of Biological Chemistry* 282(5): 3196-3204 (Nov. 27, 2006).

International Search Report and Written Opinion from parent PCT Application No. PCT/US2019/021639, 15 pages (dated Jun. 20, 2019).

Kosler et al., "Lactic acid bacteria with concomitant IL-17, IL-23 and TNFα-binding ability for the treatment of inflammatory bowel disease," *Current Pharmaceutical Biotechnology* 18(4):318-332 (Jan. 1, 2017)(Abstract).

Nicholls et al., "Lectins in ocular drug delivery: An investigation of lectin binding sites on the corneal and conjunctival surfaces," *International Journal of Pharmaceutics* 138(2): 175-183 (Jul. 26, 1996)(Abstract).

Ahuja et al., "Topical ocular delivery of NSAIDs," The AAPS Journal, 10(2):229-41 (2008).

(Continued)

*Primary Examiner* — Jeanette M Lieb
(74) *Attorney, Agent, or Firm* — Klarquist Sparkman, LLP

(57) ABSTRACT

Disclosed herein are fusion proteins for use in treating an inflammatory or immune disorder and methods of use. In some examples, the fusion proteins include an anchor domain and a therapeutic polypeptide. In some examples, the fusion proteins and methods herein can be used to treat inflammatory or immune disorders.

14 Claims, 14 Drawing Sheets

Specification includes a Sequence Listing.

(56) References Cited

OTHER PUBLICATIONS

Aly and Salem-Bekhit, "Histochemical mapping of glycoconjugates in the eyeball of the one humped camel (*Camelus dromedarius*)," *J. Pharm. Biomed. Sci.* 2(4): 33-46 (2012).
Amparo et al., "Topical interleukin 1 receptor antagonist for treatment of dry eye disease: a randomized clinical trial," *JAMA Ophthalmol.* 131(6): 715-723 (Jun. 2013).
Argüeso, "Human ocular mucins: the endowed guardians of sight," *Advanced Drug Delivery Reviews* 180: 114074, 12 pages (e-PUB Dec. 4, 2021).
Banchonglikitkul et al., "Lectins as targeting agents—the in vitro binding of lectins to lesions in the eye and mouth," *British Journal of Biomedical Science* 59(2): 115-118 (2002).
Bron et al., "TFOS DEWS II pathophysiology report," *The Ocular Surface* 15: 438-510 (2017).
Chen et al., "Interleukin-1 receptor mediates the interplay between $CD4^+T$ cells and ocular resident cells to promote keratinizing squamous metaplasia Sjogren's syndrome," *Laboratory Investigation* 92: 556-570 (e-PUB Jan. 9, 2012).
Dohlman et al., "T Cell-derived granulocyte-macrophage colony-stimulating factor contributes to dry eye disease pathogenesis by promoting CD11bþ myeloid cell maturation and migration," *Invest Ophthalmol Vis Sci.* 58:1330-1336 (2017).
Feizi et al., "Therapeutic approaches for corneal neovascularization," *Eye and Vision* 4:28, 10 pages (2017).
Hamrah et al., "Cutting edge: Topical recombinant nerve growth factor for the treatment of neurotrophic keratopathy-biologicals as a novel therapy for neurotrophic keratopathy," *Cornea* 41(6): 673-679 (e-PUB Feb. 2, 2022).
Hou et al., "Design of a superior cytokine antagonist for topical ophthalmic use," *PNAS* 110(10): 3913-3918 (Mar. 5, 2013).
International Search Report and Written Opinion for PCT/US2017/052288, dated Dec. 28, 2017, by the Israel Patent Office as ISA (14 pages).
Ji et al., "Neutralization of Ocular Surface TNF-α Reduces Ocular Surface and Lacrimal Gland Inflammation Induced by in Vivo Dry Eye," *Investigative Ophthalmology & Visual Science* 54: 7557-7566 (2013).
Leavesley et al., "Vitronectin—master controller or micromanager?" *IUBMB Life* 65(10): 807-818 (ePub Sep. 13, 2013).
Lee et al., "Topical TSG-6 administration protects the ocular surface in two mouse models of inflammation-related dry eye," *Invest Ophthalmol Vis Sci.* 56(9): 5175-5181 (2015).

Mantelli and Argüeso, "Functions of ocular surface mucins in health and disease," *Curr Opin Allergy Clin Immunol.* 8(5): 477-483 (Oct. 2008).
Mochizuki et al., "Evaluation of ocular surface glycocalyx using lectin-conjugated fluorescein," *Clinical Ophthalmology* 4: 925-930 (Aug. 13, 2010).
Parkkari et al., "Handling test of eye drop dispenser comparison of unit-dose pipettes with conventional eye drop bottles," *Journal of Ocular Pharmacology and Therapeutics* 26(3): 273-276 (2010).
Patten and Wang, "Fibronectin in development and wound healing," *Advanced Drug Delivery Reviews* 170: 353-368 (e-Pub Sep. 19, 2020).
Recalde et al., "Transforming Growth Factor-β Inhibition Decreases Diode Laser-Induced Choroidal Neovascularization Development in Rats: P17 and P144 Peptides," *Investigative Ophthalmology & Visual Science* 52: 7090-7097 (2011).
Rittig et al., "Lectin-binding sites in the anterior segment of the human eye," *Graefe's Arch Clin Exp Ophthalmol* 228: 528-532 (1990).
Singh et al., "Pigment epithelium-derived factor secreted by corneal epithelial cells regulates dendritic cell maturation in dry eye disease," *Ocul Surf.* 18(3): 460-469 (Jul. 1, 2020).
Stevenson et al., "Extraorbital lacrimal gland excision: a reproducible model of severe aqueous tear-deficient dry eye disease," *Cornea* 33(12): 1336-1341 (Dec. 2014).
Table from: *Electron Microscopy*, vol. 22, No. 1, p. 25-33, (1987) (table cited in Japanese Patent Application No. 2019-515416).
Tada et al., "Design and synthesis of binding growth factors," *International Journal of Molecular Sciences* 13(5):6053-72 (2012).
Tan et al., "The immunoregulatory role of corneal epithelium-derived thrombospondin-1 in dry eye disease," *Ocul Surf.* 16(4): 470-477 (Oct. 2018).
Tuori et al., "Lectin binding in the anterior segment of the bovine eye," *Histochemical Journal* 26: 787-798 (1994).
Vijmasi et al., "Topical administration of interleukin-1 receptor antagonist as a therapy for aqueous-deficient dry eye in autoimmune disease," *Molecular Vision* 19: 1957-1965 (Sep. 19, 2013).
Vijmasi et al., "Topical administration of lacritin is a novel therapy for aqueous-deficient dry eye disease," *Invest Ophthalmol Vis Sci.* 55:5401-5409 (Jul. 3, 2014).
Wolffsohn et al., "TFOS DEWS II diagnostic methodology report," *The Ocular Surface* 15: 539-574 (2017).
Zhong et al., "Expression and potential role of major inflammatory cytokines in experimental keratomycosis," *Molecular Vision* 15:1303-1311 (Jul. 4, 2009).

\* cited by examiner

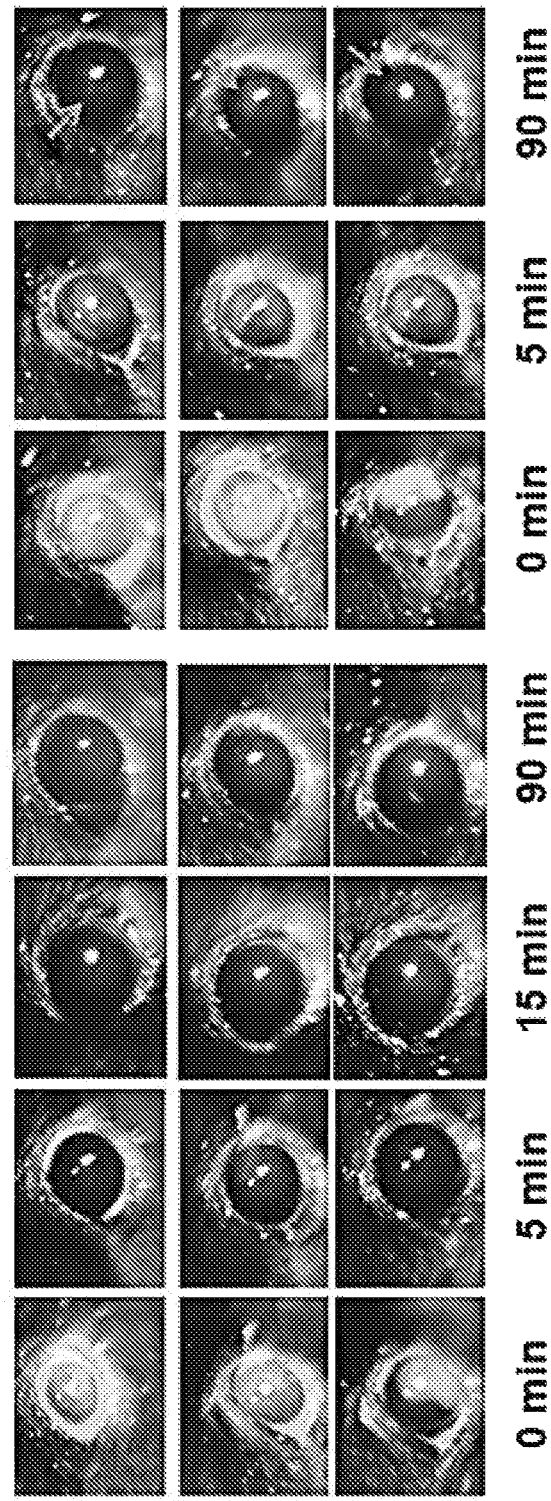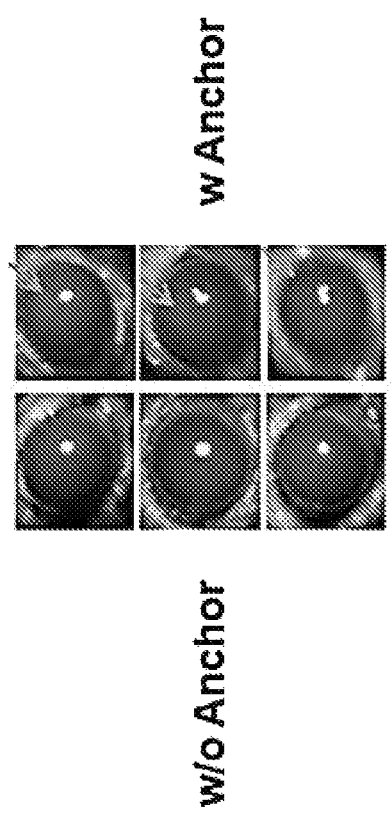

FIG. 13A
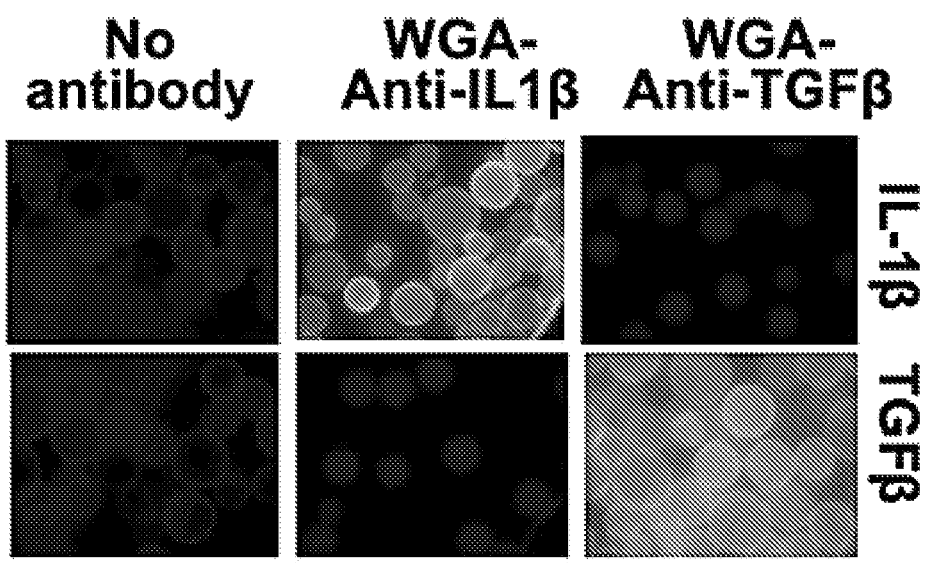
Binding of labeled IL-17
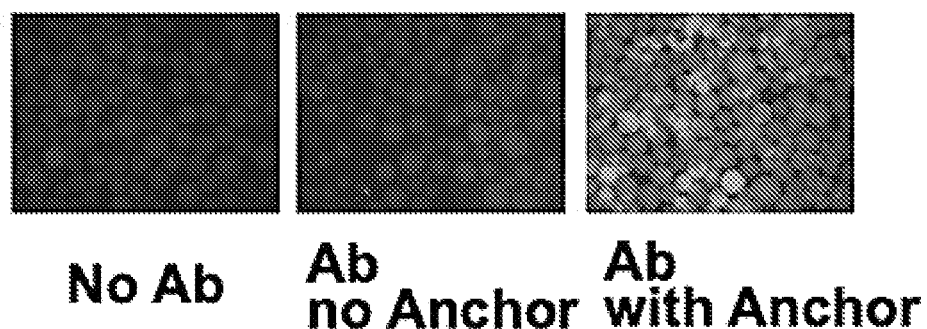
FIG. 13B

FIG. 14 A Scoring Dry Eye in the Mouse Model
FIG. 14 B
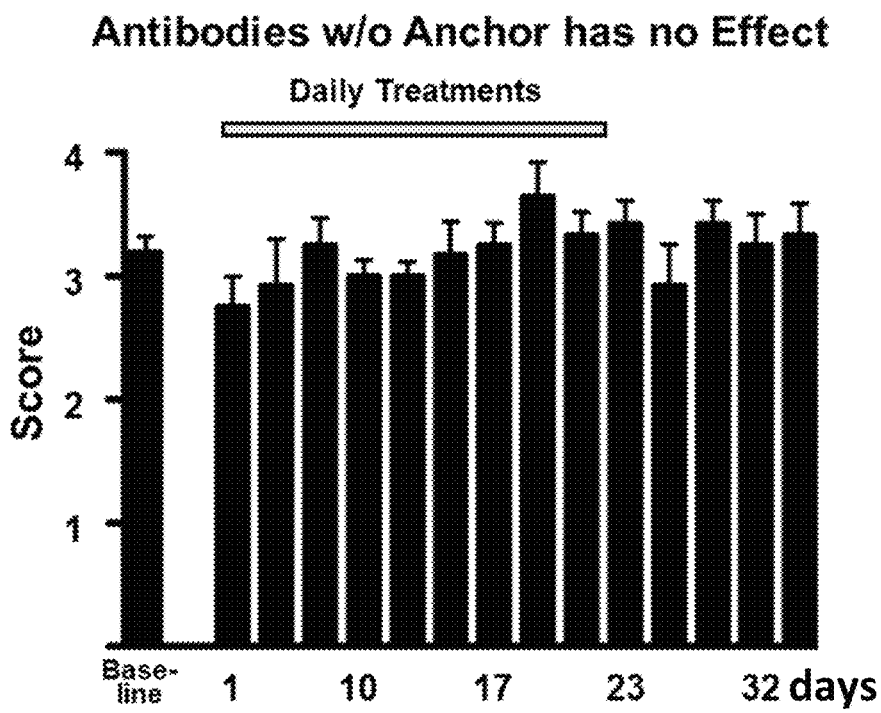
FIG. 14 C
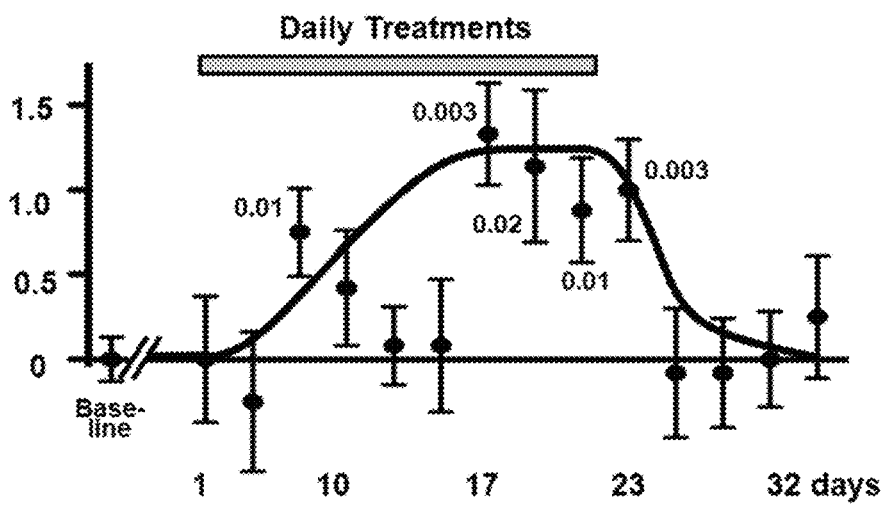

DELIVERING BIOLOGICAL DRUGS TO TISSUES

CROSS REFERENCE TO RELATED APPLICATIONS

This is a § 371 U.S. national stage of International Application No. PCT/US2019/021639, filed Mar. 11, 2019, which claims the benefit of U.S. Provisional Application No. 62/640,859, filed Mar. 9, 2018, which is herein incorporated by reference in its entirety.

FIELD

This disclosure relates to methods and compositions for delivering biological drugs to tissues.

BACKGROUND

The advent of biological therapeutics has dramatically improved treatment of many diseases, especially those with a strong inflammatory or immune system component, such as arthritis, psoriasis, and inflammatory bowel disease. However, foreign substances, including biological therapeutics, are removed effectively from many tissues by flow of fluids or mucus that cover them. Thus, a need remains for methods to target biologicals to many inflamed tissues and maintain contact with diseased tissues for sufficient time to effectuate treatment.

SUMMARY

Disclosed herein are fusion proteins and isolated nucleic acids encoding the fusion proteins. These fusion proteins include an anchor domain and a therapeutic polypeptide. In some embodiments, the fusion proteins is of use for treating an inflammatory or immune disorder.

In some embodiments (a) the anchor domain includes a lectin carbohydrate-binding anchor domain, a von Willebrand factor (vWF) collagen-binding anchor domain, a *Clostridium* collagenase (ColH) collagen-binding anchor domain, or a heparin-binding (HS) anchor domain, and the therapeutic polypeptide includes (i) an antagonist of, or antibody that specifically binds to, interleukin (IL)-9, IL-6, IL-1β, IL-1α, IL-18, interferon (IFN)γ, IL-12, granulocyte-macrophage colony-stimulating factor (GM-CSF), transforming growth factor beta (TGFβ), IL-4, IL-5, IL-13, IL-17F, IL-17A, IL-21, IL-22, IL-23, or VEGF-A, or (ii) an immunoglobulin-binding (Ig) polypeptide or an antagonist of tumor necrosis factor alpha (TNFα); or (b) the anchor domain includes a lectin carbohydrate-binding anchor domain, a von Willebrand factor (vWF) collagen-binding anchor domain, or a *Clostridium* collagenase (ColH) collagen-binding anchor domain, and the therapeutic polypeptide includes (i) an anti-inflammatory cytokine or (ii) an antagonist of, or antibody that specifically binds to, a pro-inflammatory cytokine.

The disclosed fusion proteins and nucleic acids encoding these fusion proteins are of use for treating an inflammatory or immune disorder. In some embodiments, methods are disclosed for treating a subject with an inflammatory or immune disorder. In other embodiments, pharmaceutical compositions that include these fusion proteins and nucleic acids encoding the fusion proteins are also disclosed.

The foregoing and other objects, features, and advantages of the invention will become more apparent from the following detailed description, which proceeds with reference to the accompanying figures.

BRIEF DESCRIPTION OF THE DRAWINGS

Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention. In the following description, numerous specific details are set forth to provide a thorough understanding of the present invention. The present invention may be practiced without some or all of these specific details. In other instances, well-known process operations have not been described in details so as to not unnecessarily obscure the present invention.

FIGS. 12A-12B: In FIG. 12A images of 6-8 week female-c57BL/6 mice are shown with extraorbital lacrimal glands removed and treated once with fluorescently-labeled IL-17A antibodies with and without WGA anchor. Antibodies without the WGA anchor are removed rapidly, but antibodies with WGA anchors are retained. FIG. 12B shows images of 6-8 week female-c57BL/6 mice with extraorbital lacrimal glands removed that are treated once with fluorescently-labeled IL-17A antibodies, which can be detected 8 hours after application when conjugated to a WGA anchor.

FIGS. 13A-13B: In FIG. 13A beads bound to the indicated antibodies are shown incubated with Alexa Fluor® 488-labeled IL-1β or TGFβ. FIG. 13B shows beads bound to anti-IL-17A antibodies and incubated with Alexa Fluor 488®-labeled IL-17A.

FIGS. 14A-14C show the effect of attaching a WGA anchor to anti-IL-17A antibodies on therapeutic efficacy.

SEQUENCE LISTING

Figure 1:
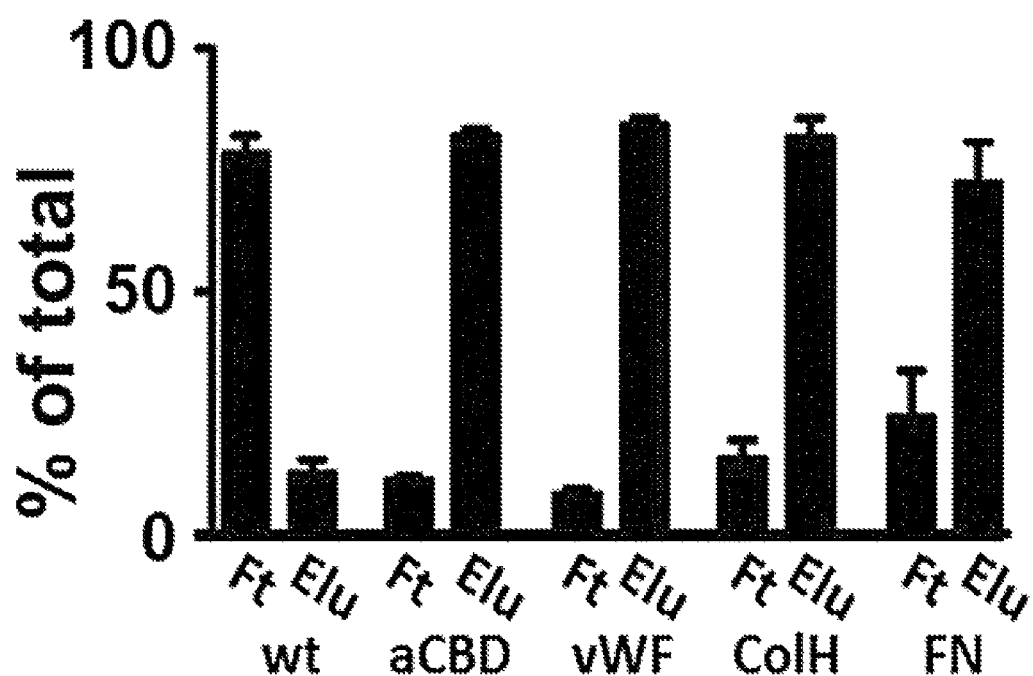
FIG. 1 is a bar graph illustrating binding of LacZ fusion proteins to collagen. Abbreviations: Ft, flow-through; Elu, eluate; wt, wild type (no anchor domain); a CBD, an artificial collagen binding domain; vWF, the binding domain from von Willebrand factor; ColH a binding domain from a bacterial collagenase; FN, a binding domain from fibronectin.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 8, 2020, 20.1 KB, which is incorporated by reference herein. In the accompanying sequence listing:

SEQ ID NO: 1 is an amino acid sequence of a collagen-binding anchor domain from the von Willebrand factor (vWF).

SEQ ID NO: 2 is an amino acid sequence of a collagen-binding anchor domain from the von Willebrand factor (vWF).

SEQ ID NO: 3 is an amino acid sequence of a collagen-binding anchor domain from Clostridiumcollagenase (ColH).

SEQ ID NO: 4 is an amino acid sequence of a heparin-binding (HS) anchor domain.

SEQ ID NO: 5 is an amino acid sequence of a heparin-binding (HS) anchor domain.

SEQ ID NO: 6 is an amino acid sequence of a carbohydrate-binding anchor domain from concanavalin A (ConA).

SEQ ID NO: 7 is an amino acid sequence of a carbohydrate-binding anchor domain from wheat germ agglutinin (WGA).

SEQ ID NO: 8 is an amino acid sequence of a carbohydrate-binding anchor domain from jacalin (Jac).

SEQ ID NO: 9 is an amino acid sequence of a linker.

SEQ ID NO: 10 is an amino acid sequence of a protein A immunoglobulin (Ig) binding fragment.

SEQ ID NO: 11 is an amino acid sequence of a protein G immunoglobulin (Ig) binding fragment.

SEQ ID NO: 12 is an amino acid sequence of an inhibitor of TNFα polypeptide from the TNF receptor 1.

SEQ ID NO: 13 is an amino acid sequence of a P144 polypeptide.

SEQ ID NO: 14 is an amino acid sequence of a P17 polypeptide.

SEQ ID NO: 15 is an amino acid sequence of a fusion peptide that includes a protein G polypeptide as the Ig-binding polypeptide and a vWF polypeptide as an anchor domain.

SEQ ID NO: 16 is an amino acid sequence of a fusion peptide that includes a protein G polypeptide as the Ig-binding polypeptide and a vWF polypeptide as an anchor domain.

SEQ ID NO: 17 is an amino acid sequence that includes two copies of P144 as a therapeutic polypeptide and a vWF polypeptide as an anchor domain.

SEQ ID NO: 18 is an amino acid sequence that includes two copies of P17 as a therapeutic polypeptide and a vWF polypeptide as an anchor domain.

SEQ ID NO: 19 is an amino acid sequence of a linker.

SEQ ID NOS: 20-26 are variants of a vWF anchor domain.

DETAILED DESCRIPTION

Disclosed herein are fusion proteins, and isolated nucleic acid molecules encoding the fusion proteins. These fusion proteins include an anchor domain and a therapeutic polypeptide. In some embodiments, the fusion proteins is of use for treating an inflammatory or immune disorder.

In some embodiments the anchor domain includes a lectin carbohydrate-binding anchor domain, a von Willebrand factor (vWF) collagen-binding anchor domain, a *Clostridium* collagenase (ColH) collagen-binding anchor domain, or a heparin-binding (HS) anchor domain, and the therapeutic polypeptide includes: (i) an antagonist of, or antibody that specifically binds to, interleukin (IL)-9, IL-6, IL-1β, IL-1α, IL-18, interferon (IFN)γ, IL-12, granulocyte-macrophage colony-stimulating factor (GM-CSF), transforming growth factor beta (TGFβ), IL-4, IL-5, IL-13, IL-17F, IL-17A, IL-21, IL-22, or IL-23, or (ii) an immunoglobulin-binding (Ig) polypeptide or an antagonist of tumor necrosis factor alpha (TNFα). In some embodiments, (b) the anchor domain includes a lectin carbohydrate-binding anchor domain, a von Willebrand factor (vWF) collagen-binding anchor domain, or a *Clostridium* collagenase (ColH) collagen-binding anchor domain, and the therapeutic polypeptide includes (i) an anti-inflammatory cytokine or (ii) an antagonist of, or antibody that specifically binds to, a pro-inflammatory cytokine.

In other embodiments, the anchor domain includes a lectin carbohydrate-binding anchor domain, a von Willebrand factor (vWF) collagen-binding anchor domain, or a *Clostridium* collagenase (ColH) collagen-binding anchor domain; and the therapeutic polypeptide includes IL-10, interleukin-1 receptor antagonist (IL-1Ra), or an antibody that specifically binds tumor necrosis factor alpha (TNFα) antagonist.

In specific non-limiting examples, the anchor domain includes a lectin carbohydrate-binding anchor domain (such as WGA), and the therapeutic polypeptide includes the inhibitor of TNFα polypeptide from the TNF receptor 1, IL-10, IL-1Ra, or an antibody that specifically binds TGFβ, TNFα, IL-1β, IL-6, IFNγ, IL-4, IL-5, IL-13, IL-17F, or IL-17A. In other examples, the anchor domain includes the vWF collagen-binding anchor domain or the ColH collagen-binding anchor domain, and the therapeutic polypeptide includes the inhibitor of TNFα polypeptide from the TNF receptor 1, IL-1Ra, IL-10, P17, P144, or the Ig-binding polypeptide. In further examples, the anchor domain includes the HS anchor domain, and the therapeutic polypeptide includes the inhibitor of TNFα polypeptide from the TNF receptor 1.

The fusion proteins herein can further include a label, solubility enhancing sequence, purification tag, or combinations thereof. In some examples, the anchor domain, therapeutic peptide or combination thereof are further benzylated, glycosylated, acetylated, phosphorylated, amidated, pegylated, or combinations thereof.

Methods for treating an inflammatory disorder or an immune disorder are also disclosed. In some embodiments, the fusion protein can be administered to a tissue in a mouth, a bladder, a nasal cavity, a gastrointestinal tract, a lung, a joint, an eye, or the reproductive system of a subject. In other embodiments, the inflammatory or immune disorder includes chronic obstructive pulmonary disease, asthma, bronchitis, rhinosinusitis, mucositis, left-sided ulcerative colitis, inflammatory bowel disease, periodontal disease, peri-implantitis, interstitial cystitis, atrophic vaginitis, or arthritis. In further embodiments, the methods include administering to the tissue of the subject a therapeutically effective amount of any fusion protein disclosed herein, thereby treating the inflammatory disorder or an immune disorder of the tissue in the subject. In some examples, the methods further include administering to the tissue of the subject a therapeutically effective amount any fusion protein disclosed herein, wherein the therapeutic polypeptide includes the Ig-binding polypeptide, and any therapeutically effective antibody, thereby treating the inflammatory disorder or an immune disorder of the tissue in the subject.

In some embodiments, the subject has an inflammatory disorder or an immune disorder that affects the eye (such as dry eye or Sjögren's syndrome), and the therapeutic polypeptide includes an antibody that specifically binds IL-17A or IL-23.

Also disclosed herein are pharmaceutical compositions that include a therapeutically effective amount of any of the fusion proteins disclosed herein and a pharmaceutically acceptable carrier. These pharmaceutical compositions can be formulated for external and/or topical administration to a tissue. The pharmaceutical compositions can further include a unit dose dispenser for dispensing any of the pharmaceutical compositions disclosed herein locally to an inflamed tissue. In specific non-limiting examples, the pharmaceutical composition is formulated as a gel, cream, lotion, or ointment.

I. Terms

Unless otherwise noted, technical terms are used according to conventional usage. Definitions of common terms in molecular biology can be found in Lewin B, Genes VII, 1999; Kendrew et al., The Encyclopedia of Molecular Biology, 1994; Meyers R, Molecular Biology and Biotechnology: a Comprehensive Desk Reference, 1995; and other similar references.

Where a range of values is provided, it is intended that each intervening value between the upper and lower limit of that range and any other stated or intervening value in that stated range is encompassed within the disclosure. For example, a range of 0.01, 0.1, 1, 10, 100, or 1000 µg/ml per day is also intended to explicitly disclose a range of values greater than or equal to 0.01 µg/ml per day and the range of values less than or equal to 1000 µg/ml per day.

All percentages, parts and ratios are based upon the total weight of the topical compositions and all measurements made are at about 25° C. unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, such as, "about 100 µg/ml per day" means 90 to 110 µg/ml per day, etc., unless the context of the disclosure indicates otherwise or is inconsistent with such an interpretation. For example, in a list of numerical values, such as "10, 100, or 1000 µg/ml per day," "100 µg/ml per day" means a range extending to less than half the interval(s) between the preceding and subsequent values, for example, more than 55 to less than 550. Furthermore, the phrases "less than about" a value or "greater than about" a value should be understood in view of the definition of the term "about" provided herein. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

The term "comprises" means "includes." All publications, patent applications, patents, and other references mentioned herein, such as GENBANK® references, are incorporated by reference in their entirety. Dates of GENBANK® Accession Nos. referred to herein are the sequences available at least as early as Mar. 19, 2019. In case of conflict, the present specification, including explanations of terms, will control. In addition, the materials, methods, and examples are illustrative only and not intended to be limiting.

To facilitate review of the various embodiments, the following explanations of terms are provided.

*Acanthamoeba keratitis*: A rare but serious infection of the eye that can result in permanent visual impairment or blindness. This infection is caused by a microscopic, free-living ameba (single-celled living organism) called *Acanthamoeba*.

Administration/delivery: To provide or give a subject an agent by any effective route. Exemplary routes of administration include, but are not limited to, topical application, such as eye drops. For example, if the chosen route is local, the composition is administered by introducing the composition into the eye, such as onto the ocular surface of the subject. The term also encompasses long-term administration, such as is accomplished using a continuous release formulation.

The three primary methods of delivery of ocular medications to the eye are topical, local ocular (i.e., subconjunctival, intravitreal, retrobulbar, and intracameral), and systemic. The most appropriate method of administration depends on the area of the eye to be medicated. The conjunctiva, cornea, anterior chamber, and iris typically respond well to topical therapy. Typically, the eyelids can be treated with topical therapy but more frequently require systemic therapy.

Amino acid substitution: The replacement of one amino acid in peptide with a different amino acid.

Agent: Any substance or any combination of substances that is useful for achieving an end or result. Agents include proteins, nucleic acid molecules, compounds, small molecules, organic compounds, inorganic compounds, or other molecules of interest, such as viruses, such as recombinant viruses. An agent can include a therapeutic agent, a diagnostic agent, or a pharmaceutical agent. A therapeutic agent is a substance that demonstrates some therapeutic effect by restoring or maintaining health, such as by alleviating the symptoms associated with a disease or physiological disorder, delaying (including preventing) progression or onset of a disease, or allowing for a specific molecule with a biological function to be retained locally. In some embodiments, the agent is a polypeptide agent. For example, protein A, protein G, and protein L are therapeutic agents because they can bind a therapeutic antibody and thus achieve therapeutic efficacy when used with a monoclonal or polyclonal antibody. The skilled artisan will understand that particular agents may be useful to achieve more than one result.

Anchor domain: A protein domain that can attach to a cell surface by binding extracellular molecules, such as collagen and heparin. Anchor domains generally bind molecules at a tissue surface through non-covalent bonds.

Animal: Living multi-cellular vertebrate organisms, a category that includes, for example, mammals and birds. The term mammal includes both human and non-human mammals. Similarly, the term "subject" includes both human and veterinary subjects.

Antagonist: A molecule that binds to another molecule (such as a cytokine) and neutralizes it, or a molecule that binds to a receptor and, for example, blocks binding of the cytokine. In specific examples, the antagonist is not an antibody, or is a non-antibody antagonist.

Antibody: A polypeptide substantially encoded by an immunoglobulin gene or immunoglobulin genes or fragments thereof, which specifically binds and recognizes an analyte (antigen). Immunoglobulin genes include the kappa, lambda, alpha, gamma, delta, epsilon, and mu constant region genes as well as myriad immunoglobulin variable region genes.

Antibodies exist, for example, as intact immunoglobulins and as a number of well-characterized fragments produced by digestion with various peptidases, such as Fabs, Fvs, and single-chain Fvs (SCFvs). Included are intact immunoglobulins as well as the variants and portions thereof that are well known in the art, such as Fab' fragments, F(ab)$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while, in dsFvs, the chains have been mutated to introduce a disulfide bond to stabilize the association of the chains. The term also includes genetically engineered forms, such as chimeric antibodies (e.g., humanized murine antibodies) and heteroconjugate antibodies (e.g., bispecific antibodies). See also, Pierce Catalog and Handbook, 1994-1995 (Pierce Chemical Co., Rockford, Ill.); Kuby, J., Immunology, 3 rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance, by making hybrid antibody-forming cells from a fusion of myeloma cells with immune spleen cells. These fused cells and their progeny are termed "hybridomas." Monoclonal antibodies include humanized monoclonal antibodies. In some examples, monoclonal antibodies are isolated from a subject. The amino acid sequences of such isolated monoclonal antibodies can be determined.

A "polyclonal antibody" is an antibody that is secreted by different B cell lineages within the body (whereas monoclonal antibodies come from a single cell lineage). It includes a collection of immunoglobulin molecules that react against a specific antigen, each identifying a different epitope.

Antigen: A polypeptide that can stimulate the production of antibodies or a T cell response in an animal, including polypeptides that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation.

Autoimmune disorder: A disorder in which the immune system produces an immune response (e.g., a B cell or a T cell response) against an endogenous (self) antigen, with consequent injury to tissues. The injury may be localized to certain organs, such as thyroiditis, or may involve a particular tissue at different locations, such as Goodpasture's disease, or may be systemic, such as lupus erythematosus. In specific examples, the tissues include tissue in the eye, mouth, bladder, or joint (or other cartilage-containing tissue).

In some examples, autoimmune diseases include type I diabetes, ankylosing spondylitis, Behcet's syndrome, dermatomyositis, Graves' disease, juvenile rheumatoid arthritis, multiple sclerosis, psoriatic arthritis, Reiter's syndrome, rheumatoid arthritis, Sjögren's syndrome, systemic lupus erythematosus, Wegener's granulatomatosis, myasthenia gravis, ankylosing spondylitis, celiac disease, Crohn's disease, Hashimoto's thyroiditis, or autoimmune uveitis), graft versus host disease, and allograft rejection.

Chronic condition: A human health condition or disease that is persistent or otherwise long-lasting in its effects or a disease that comes with time. The term chronic is often applied when the course of the disease lasts for more than three months. Common chronic diseases include autoimmune diseases.

*Clostridium* collagenase (ColH): One of several bacterial collagenases that have been widely studied for their biochemical and enzymatic properties. It is a metalloproteinase that is able to digest triple-helical type I, II, and III collagen into simple peptides under physiological conditions. Examples of sequences are available in GENBANK® (e.g., Accession Nos. D29981.1 and BAA06251.1, incorporated by reference herein as available on Mar. 9, 2018, which provide exemplary nucleotide and protein sequences for ColH); other examples are available herein (e.g., SEQ ID NO: 2).

Collagen: The main structural protein in the extracellular space in the various connective tissues in animal bodies. As the main component of connective tissue, it is the most abundant protein in mammals, making up from 25% to 35% of the whole-body protein content. Depending upon the degree of mineralization, collagen tissues may be rigid (bone), compliant (tendon), or have a gradient from rigid to compliant (cartilage). Collagen, in the form of elongated fibrils, is mostly found in fibrous tissues, such as tendons, ligaments, and skin. It is also abundant in corneas, cartilage, bones, blood vessels, the gut, intervertebral discs, and the dentin in teeth. In muscle tissue, it serves as a major component of the endomysium. Collagen constitutes one to two percent of muscle tissue and accounts for 6% of the weight of strong, tendinous muscles. The fibroblast is the most common cell that creates collagen. Twenty-eight types of collagen have been identified. Collagen includes fibrillar (types I, II, II, V, and XI) and non-fibrillar collagen.

Concanavalin A (ConA): A lectin (carbohydrate-binding protein) from the jack-bean, *Canavalia ensiformis*. It binds to mainly internal and non-reducing terminal α-D-mannosyl and α-D-glucosyl groups. ConA binds to surfaces of many cell types and is widely used in biology and biochemistry to characterize glycoproteins and other sugar-containing molecules on the surface of cells. It is also used to purify glycoproteins by affinity chromatography. ConA sequences are publicly available. GENBANK® Accession Nos. AAL09432.1 and AF308777.1, incorporated herein by reference as available on Mar. 9, 2018, provide exemplary jack bean ConA protein and nucleotide sequences, respectively. Other examples are available herein (e.g., SEQ ID NO: 12).

Contacting: Placement in direct physical association; includes both in solid and liquid form. Contacting includes contact between one molecule and another molecule, for example the amino acid on the surface of one polypeptide, such as a therapeutic peptide, that contacts another polypeptide. Contacting can also include contacting a cell for example by placing a peptide in direct physical association with a cell.

Control: A reference standard. In some embodiments, the control is a sample obtained from a healthy patient. In other embodiments, the control is a tissue sample obtained from a patient diagnosed with an inflammatory or immune disorder. In still other embodiments, the control is a historical control or standard reference value or range of values (e.g., a previously tested control sample with a known prognosis or outcome or group of samples that represent baseline or normal values). A difference between a test sample and a control can be an increase or a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Conjunctiva: A thin, clear, moist membrane that coats the inner surfaces of the eyelids (i.e., palpebral conjunctiva) and the outer surface of the eye (i.e., ocular, or bulbar, conjunctiva). The conjunctiva lines the inside of the eyelids and covers the sclera (i.e., the white of the eye); it is composed of a non-keratinized, stratified columnar epithelium with goblet cells and a stratified columnar epithelium. The conjunctiva is highly vascularized with many microvessels that are easily accessible for imaging studies. The conjunctiva helps lubricate the eye by producing mucus and tears, although at a smaller volume of tears than the lacrimal gland. It also contributes to immune surveillance and helps prevent microbes from entering the eye.

Cytokines: A broad category of small proteins (approximately 5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumor necrosis factors but generally not hormones or growth factors. Cytokines are produced by a broad range of cells, including immune cells, such as macrophages, B lymphocytes, T lymphocytes, and mast cells, as well as endothelial cells, fibroblasts, and various stromal cells; a given cytokine may be produced by more than one type of cell. Cytokines are important in health and disease, specifically in host responses to infection, immune responses, inflammation, trauma, sepsis, cancer, and reproduction. They act through receptors and are especially important in the immune system; cytokines modulate the balance between humoral and cell-based immune responses, and they regulate the maturation, growth, and responsiveness of particular cell populations. Cytokines include interleukins.

In some examples, a cytokine can be an anti-inflammatory cytokine, which means that the cytokine functions to decrease an inflammatory response, for example, by inhibiting the release of pro-inflammatory cytokines. Examples of anti-inflammatory cytokines include interleukin (IL)-10, IL-1Ra, IL-6, IL-9, IL-21, IL-22, granulocyte-colony stimulating factor (G-CSF), vascular endothelial growth factor A (VEGF-A), IL-4, IL-5, IL-13, and transforming growth factor (TGF)β. In other examples, a cytokine can be a pro-inflammatory cytokine, which means that the cytokine functions to increase an inflammatory response, for example, by responding to an infection or, in the case of excessive production of pro-inflammatory cytokines, by facilitating an inflammatory or immune disorder. Examples of pro-inflammatory cytokines include IL-9, IL-6, IL-1β, IL-1α, tumor necrosis factor alpha (TNFα), IL-18, interferon (IFN)γ, IL-12, granulocyte-macrophage colony-stimulating factor (GM-CSF), TGFβ, IL-21, IL-22, IL-23, IL-4, IL-5, IL-13, IL-17F, IL-17A, and VEGF-A. In some cases, a cytokine is pleiotropic, which means that the cytokine can function as either anti-inflammatory or pro-inflammatory depending on the context. Examples of pleiotropic cytokines include IL-9, IL-6, TGFβ, IL-21, IL-22, IL-4, IL-5, IL-13, and VEGF-A. Other cytokines that are anti-inflammatory, pro-inflammatory, or pleiotropic are known in the art.

Domain: A domain of a protein is a part of a protein that shares common structural, physiochemical, and functional features, such as hydrophobic, polar, globular, helical domains or properties (e.g., a collagen-binding, carbohydrate-binding, or heparin-binding domain). A domain can also be a functional domain that has a particular enzymatic activity or feature, such as a domain of protein A, protein G, or protein L that binds monoclonal or polyclonal antibodies.

Dry eye: A condition that occurs when either the eye does not produce enough tears or when the tears evaporate too quickly. This can result from meibomian gland dysfunction, allergies, pregnancy, Sjogren's syndrome, vitamin A deficiency, LASIK surgery, certain medications (e.g., antihistamines), certain blood pressure medication, hormone replacement therapy, and antidepressants. Chronic conjunctivitis, such as from tobacco smoke exposure or infection, may also lead to dry eye. Diagnosis is based on symptoms, evaluation of tear secretion, and/or staining of the ocular surface.

Dry eye disease (DED): A condition also known as dry eye syndrome (DES), keratoconjunctivitis sicca (KCS), and keratitis sicca, which is a multifactorial disease of the tears and the ocular surface that results in discomfort, visual disturbance, and tear film instability with potential damage to the ocular surface. Dry eye syndrome is a common form of ocular surface disease (OSD) and may overlap with other causes of OSD, such as ocular allergy and meibomian gland dysfunction (MGD). Dry eye syndrome includes symptoms caused by multiple conditions, such as keratoconjunctivitis sicca, Sjörgen's syndrome, corneal injury, age-related dry eye, Stevens-Johnson syndrome, congenital alachrima, side effects from a drug or drugs, infection, Riley-Day syndrome, conjunctival fibrosis, eye stress, glandular and tissue destruction, ocular cicatrical pemphogoid, blepharitis, autoimmune and other immunodeficient disorders, allergies, diabetes, lacrimal gland deficiency, lupus, Parkinson's disease, Sjogren's syndrome, rheumatoid arthritis, rosacea, environmental exposure to excessively dry air, airborne particulates, smoke, smog, and an inability to blink (see U.S. Patent Pub. No. 2006/0281739, incorporated herein by reference). Symptoms of DED include a burning sensation, itchy eyes, aching sensations, heavy eyes, fatigued eyes, sore eyes, a dryness sensation, red eyes, photophobia (light sensitivity), blurred vision, foreign body sensation (i.e., a feeling that grit or some other object or material is in the eye), and watery eyes.

Epithelium: Epithelial tissues line the cavities and surfaces of blood vessels and organs throughout the body. These tissues can be arranged in a single layer of cells as a simple epithelium, either squamous, columnar, or cuboidal, or in layers of two or more cells deep as a stratified (layered) epithelium, either squamous, columnar, or cuboidal. All glands are made up of epithelial cells. Functions of epithelial cells include secretion, selective absorption, protection, transcellular transport, and sensing. Epithelial layers contain no blood vessels; therefore, they must receive nourishment via diffusion of substances from the underlying connective tissue through the basement membrane.

The "corneal epithelium" is made up of epithelial tissue and covers the front of the cornea. It acts as a barrier to protect the cornea, resisting the free flow of fluids from the tears, and prevents bacteria from entering the epithelium and corneal stroma.

Expression: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which they are operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components the presence of which can influence expression and can also include additional components the presence of which is advantageous, such as leader sequences and fusion partner sequences. Expression control sequences can include a promoter.

A promoter is a minimal sequence sufficient to direct transcription. Also included are promoter elements that are sufficient to render promoter-dependent gene expression controllable for cell-type specificity or tissue-specificity or that is inducible by external signals or agents; such elements may be located in the 5' or 3' regions of the gene. Both constitutive and inducible promoters are included (see, for example, Bitter et al., Methods in Enzymology 153:516-544, 1987). Promoters produced by recombinant DNA or synthetic techniques may also be used to provide for transcription of the nucleic acid sequences.

Expression vector: A vector that includes a recombinant polynucleotide comprising expression control sequences operatively linked to a nucleotide sequence to be expressed.

An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Eye disorder: Any disturbance, defect, or abnormality in eye function or structure, such as corneal haze and scarring, dry eye disease, or ocular inflammation. An eye disorder can be congenital, hereditary, or the result of a trauma, such as an injury, an illness, inflammation, an autoimmune disease, an infection (e.g., an acanthamoebal, a viral, a bacterial, or a fungal infection), a foreign body, ultraviolet light exposure, contact lens overwear, or a drug.

Fusion protein: A composite protein (i.e., a single contiguous amino acid sequence) made up of two (or more) distinct, heterologous polypeptides, which are not normally covalently bound together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid or by chemical synthesis methods (i.e., chemical conjugation) that are well-known in the art. A fusion protein can include an anchor domain and a therapeutic polypeptide as well as, optionally, a linker between the anchor domain and the therapeutic polypeptide.

Glycocalyx: The glycocalyx is a glycoprotein-polysaccharide covering that surrounds the cell membranes of certain bacteria, epithelia, and other cells. Most animal epithelial cells have a fuzz-like coat on the external surface of their plasma membranes. This coating consists of several carbohydrate moieties of membrane glycolipids and glycoproteins, which serve as backbone molecules for support. Generally, the carbohydrate portion of the glycolipids found on the surface of plasma membranes helps these molecules contribute to cell-cell recognition, communication, and intercellular adhesion.

Granulocyte-colony stimulating factor (G-CSF or GCSF): Also known as colony-stimulating factor 3 (CSF 3; e.g., OMIM 138970), G-CSF is an anti-inflammatory cytokine. G-CSF improves white blood cell counts after radiation exposure; can be used to treat heart degeneration; and has been shown to reduce inflammation, reduce amyloid beta burden in Alzheimer's disease, and reverse cognitive impairment. G-CSF may also be used to treat cerebral ischemia and neurological disease (such as amyotrophic lateral sclerosis and chronic traumatic brain injury). Examples of sequences are available in GENBANK® (e.g., Accession Nos. NP_000750.1 and NM_000759.3, incorporated by reference herein as available on Mar. 9, 2019, which provide exemplary protein and nucleotide sequences for G-CSF, respectively). One of ordinary skill in the art can identify additional G-CSF nucleic acid and protein sequences, including G-CSF variants that retain G-CSF biological activity (such as anti-inflammatory and neuroprotective activity).

Granulocyte-macrophage colony-stimulating factor (GM-CSF or GMCSF): Also known as colony-stimulating factor 2 (CSF 2; e.g., OMIM 138960), GM-CSF is a pro-inflammatory cytokine. GM-CSF is a part of the immune/inflammatory cascade, important for fighting infection. GM-CSF also aids in helping white blood cell levels recover following chemotherapy or autologous bone marrow transplantation; aids in alleviating immunosuppression; restores monocyte and neutrophil function. However, GM-CSF further has pro-inflammatory activity (such as in rheumatoid arthritis). Examples of sequences are available in GENBANK® (e.g., Accession Nos. NP_000749.2 and NM_000758.4, incorporated by reference herein as available on Mar. 9, 2019, which provide exemplary protein and nucleotide sequences for GM-CSF, respectively). One of ordinary skill in the art can identify additional GM-CSF nucleic acid and protein sequences, including GM-CSF variants that retain GM-CSF biological activity (such as pro-inflammatory activity).

Heparin: A polysaccharide present in mast cells that is extensively used as an anticoagulant (Oduah et al, Pharmaceuticals, 9, 38, doi:10.3390, 2016). It is structurally similar to heparan sulfate, and the HS domain binds to both heparin and heparan sulfate with high affinity.

Heparan sulfate (HS): A linear polysaccharide found in all animal tissues, occurring as a proteoglycan (HSPG) in which two or three HS chains are attached in close proximity to cell surface or extracellular matrix proteins. In this form, HS binds a variety of protein ligands and regulates a wide variety of biological activities, including developmental processes, angiogenesis, blood coagulation, abolishing detachment activity by GrB (Granzyme B), and tumor metastasis. Heparan sulfate is also a cellular receptor for a number of viruses. It is structurally similar to heparin.

Immune Disorder: A disorder in which the immune response plays a role in the development or progression of the disease. Immune disorders include autoimmune disorders, allograft rejection, graft versus host disease, and inflammatory conditions. Thus, some immune disorders, such as autoimmune disorders, may also be characterized as inflammatory disorders.

Immunoglobulins: A class of proteins found in plasma and other body fluids that exhibit antibody activity and binds with other molecules with a high degree of specificity; immunoglobulins are divided into five classes (IgM, IgG, IgA, IgD, and IgE) on the basis of structure and biological activity. Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125, 023; Faoulkner et al., Nature 298:286, 1982; Morrison, J. Immunol. 123: 793, 1979; Morrison et al., Ann Rev. Immunol 2:239, 1984, all of which are incorporated herein by reference).

Naturally occurring immunoglobulins are made up of four polypeptide chains. There are two long chains referred to as "heavy" or "H" chains, which weigh between about 50 and 75 kilodaltons, and two short chains referred to as "light" or "L" chains, which weigh about 25 kilodaltons. These chains are linked together by disulfide bonds to form a "Y"-shaped molecule. Each heavy chain and light chain can be divided into a variable region and a constant region. An Fc region includes the constant regions of the heavy and the light chains, but not the variable regions. Fc receptors are receptors that specifically bind an Fc region of an immunoglobulin.

Interferon gamma (IFNγ): Also known as IFNG, IFG, and IFN immune (IFI; e.g., OMIM 147570), IFNγ is a cytokine that binds the IFNγ receptor (IFNγR) and exhibits antiviral, antibacterial, and antiprotozan activity. IFNγ is primarily expressed by leukocytes, such as T cells, and aberrant expression of IFNγ has been implicated in various autoinflammatory and autoimmune diseases. Exemplary protein and nucleotide sequences for IFNγ are available at GENBANK® (e.g., Accession Nos. AAB59534.1 and NM_000619.2, respectively, incorporated by reference herein as available on Mar. 9, 2018).

Interleukin (IL)-1 receptor antagonist (Ra): A member of the IL-1 cytokine family, IL-1Ra is secreted by various types of cells, including immune cells, epithelial cells, and adipocytes, and is a natural inhibitor of the pro-inflammatory effect of IL1β. This protein inhibits the activities of interleukin 1, alpha (IL1A) and interleukin 1, beta (IL1B) and modulates a variety of interleukin 1-related immune and inflammatory responses. Exemplary protein and nucleotide sequences for IL-1Ra are available at GENBANK® (e.g., Accession Nos. CAA36262.1 and AJ005835.1, respectively, incorporated by reference herein as available on Mar. 9, 2018).

Interleukin 1-alpha (IL-1α): Also known as IL1A and IL-alpha (e.g., OMIM 147760), IL-1α is a pro-inflammatory cytokine. IL-1α is generated by activated macrophages, as well as neutrophils, epithelial cells, and endothelial cells and produces inflammation, including fever and sepsis. IL-1α plays a role in regulating the immune response. Exemplary protein and nucleotide sequences for IL-1α are available at GENBANK® (e.g., Accession Nos. AAH13142.1 and NM_000575.4, respectively, incorporated by reference herein as available on Mar. 9, 2019).

Interleukin 1-beta (IL-1β): Also known as IL1B, IL1-beta, leukocytic pyrogen, leukocytic endogenous mediator, mononuclear cell factor, and lymphocyte activating factor (e.g., OMIM 147720), IL-1β is a cytokine produced by activated macrophages and is an important mediator of the inflammatory response. IL-1β is involved in a variety of cellular activities, including cell proliferation, differentiation, and apoptosis. Increased production and/or activity of IL-1β causes multiple autoinflammatory syndromes and has been linked to susceptibility to cancer and tuberculosis. Exemplary protein and nucleotide sequences for IL-1β are available at GENBANK® (e.g., Accession Nos. NP_000567.1 and NM_000576.2, respectively, incorporated by reference herein as available on Mar. 9, 2018).

Interleukin 4 (IL-4): Also known as B-cell stimulatory factor 1; (BSF1; for example, OMIM 147780), IL-4 is a pleiotropic cytokine expressed in TH2 cells. IL-4 decreases pathological inflammation but it also associated with development of immune disorders (such as autoimmune diseases) and tumor progression. Examples of sequences are available in GENBANK® (e.g., Accession Nos. P05112.1 and MH644812.1, incorporated by reference herein as available on Mar. 9, 2019, which provide exemplary protein and nucleotide sequences for IL-4, respectively). One of ordinary skill in the art can identify additional IL-4 nucleic acid and protein sequences, including IL-4 variants that retain IL-4 biological activity (such as pleiotropic activity).

Interleukin 5 (IL-5): Also known as eosinophil differentiation facto (EDF; for example, OMIM 147850), IL-5 is a pro-inflammatory cytokine produced by Th2 cells and mast cells. IL-5 plays a role in allergic diseases, such as allergic rhinitis and asthma, but has also been shown to have anti-inflammatory properties. Examples of sequences are available in GENBANK® (e.g., Accession Nos. NP_000870.1 and NM_000879.3, incorporated by reference herein as available on Mar. 9, 2019, which provide exemplary protein and nucleotide sequences for IL-5, respectively). One of ordinary skill in the art can identify additional IL-5 nucleic acid and protein sequences, including IL-5 variants that retain IL-5 biological activity (such as pleiotropic activity).

Interleukin 6 (IL-6): Also known as interferon beta-2; IFNB2, B-cell differentiation factor, B-cell stimulatory factor 2 (BSF2), hepatocyte stimulatory factor (HSF), and hybridoma growth factor (HGF; e.g., OMIM 147620), IL-6 is an interleukin that acts as both a pro-inflammatory cytokine and an anti-inflammatory myokine. IL-6 is secreted by T cells and macrophages to stimulate an immune response (e.g., during infection and after trauma, especially burns or other tissue damage leading to inflammation) and has been implicated in the inflammatory and autoimmune processes of various diseases. Exemplary protein and nucleotide sequences for IL-6 are available at GENBANK® (e.g., Accession Nos. P05231.1 and NM_001318095.1, respectively, incorporated by reference herein as available on Mar. 9, 2019).

Interleukin 9 (IL-9): Also known as T-cell/mast cell growth factor, P40, and HP40 (e.g., OMIM 146931), IL-9 is an interleukin that acts as both a pro-inflammatory cytokine and an anti-inflammatory cytokine. IL-9 is produced by multiple cell types, including mast cells, NKT cells, Th2, Th17, Treg, ILC2, and Th9 cells. IL-9 acts through the IL-9 receptor (IL9R) and regulates multiple hematopoietic cells, stimulates cell proliferation, and prevents apoptosis. IL-9 has been implicated in asthma and is an inhibitor of melanoma growth. Exemplary protein and nucleotide sequences for IL-9 are available at GENBANK® (e.g., Accession Nos. AAC17735.1 and NM_000590.1, respectively, incorporated by reference herein as available on Mar. 9, 2019).

Interleukin 10 (IL-10): Also known as human cytokine synthesis inhibitory factor (CSIF; e.g., OMIM 124092), IL-10 is an anti-inflammatory cytokine. IL-10 signals through a receptor complex consisting of two IL-10 receptor-1 and two IL-10 receptor 2 proteins. Multiple disease states, such as inflammatory diseases, are associated with low levels of IL-10, but IL-10 has shown both immunosuppressive and immunostimulatory effects, depending on the physiological context. Examples of sequences are available in GENBANK® (e.g., Accession Nos. AAI04253.1 and NM_000572.2, incorporated by reference herein as available on Mar. 9, 2018, which provide exemplary protein and nucleotide sequences for IL-10, respectively). One of ordinary skill in the art can identify additional IL-10 nucleic acid and protein sequences, including IL-10 variants that retain IL-10 biological activity (such as anti-inflammatory activity).

Interleukin 12 (IL-12): Also known as p35 subunit; cytotoxic lymphocyte maturation factor (CLMF); natural killer cell stimulatory factor, 35-kd subunit (NKSF1); and IL35, p35 subunit (e.g., OMIM 161560), IL-12 is a pro-inflammatory cytokine. IL-12 is produced by dendritic cells, macrophages, neutrophils, and human B-lymphoblastoid cells (NC-37) in response to antigenic stimulation. L-12 is linked with autoimmunity (such as psoriasis and inflammatory bowel disease), aids in regulating the host immune response (such as against bacterial and fungal infection), and has antiangiogenic activity. Examples of sequences are available in GENBANK® (e.g., Accession Nos. AAB36675.1 and U64198.1, incorporated by reference herein as available on Mar. 9, 2019, which provide exemplary protein and nucleotide sequences for IL-12, respectively). One of ordinary skill in the art can identify additional IL-12 nucleic acid and protein sequences, including IL-12 variants that retain IL-12 biological activity (such as pro-inflammatory activity).

Interleukin 13 (IL-13): IL-13 is a pleiotropic cytokine secreted by multiple cell types, including Th2 cells, CD4 cells, NKT cells, mast cell, basophil cells, eosinophil cells, and nuocyte cells. IL-13 has both pro-inflammatory and anti-inflammatory roles in asthma and other allergies. Examples of sequences are available in GENBANK® (e.g., Accession Nos. AAH96141.2 and U31120.1, incorporated by reference herein as available on Mar. 9, 2019, which provide exemplary protein and nucleotide sequences for IL-13, respectively). One of ordinary skill in the art can identify additional IL-13 nucleic acid and protein sequences, including IL-13 variants that retain IL-13 biological activity (such as pleiotropic activity).

Interleukin 17 (IL-17A): Also known as IL-17 and cytotoxic T-lymphocyte-associated serine esterase 8 (CTLA8; for example, OMIM 603149), IL-17A is a pro-inflammatory cytokine. IL-17A is associated with immune and autoimmune diseases, such as rheumatoid arthritis, asthma, lupus, allograft rejection, anti-tumor immunity, psoriasis, multiple sclerosis, and allergies. Examples of sequences are available in GENBANK® (e.g., Accession Nos. AAH67505.1 and NM_052872.3, incorporated by reference herein as available on Mar. 9, 2019, which provide exemplary protein and nucleotide sequences for IL-17A, respectively). One of ordinary skill in the art can identify additional IL-17A nucleic acid and protein sequences, including IL-17A variants that retain IL-17A biological activity (such as pro-inflammatory activity).

Interleukin 17F (IL-17F): Also known as ML1 (for example, OMIM 606496), IL-17F is a pro-inflammatory cytokine expressed in activated T cells. IL-17F is upregulated during inflammation and is associated with asthma. Examples of sequences are available in GENBANK® (e.g., Accession Nos. AAH70124.1 and NM_002190.3, incorporated by reference herein as available on Mar. 9, 2019, which provide exemplary protein and nucleotide sequences for IL-17F, respectively). One of ordinary skill in the art can identify additional IL-17F nucleic acid and protein sequences, including IL-17F variants that retain IL-17F biological activity (such as pro-inflammatory activity).

Interleukin 18 (IL-18): Also known as interferon-gamma-inducing factor (IGIF); small inducible cytokine subfamily b, member 8 (SCYB8); monocyte-derived neutrophil chemotactic factor; neutrophil-activating peptide 1 (NAP1); granulocyte chemotactic protein 1 (GCP1); and chemokine, CXC motif, ligand 8 (CXCL8) (e.g., OMIM 600953 and 146930), IL-18 is apro-inflammatory cytokine. IL-18 induces the host immune response to infection by microorganisms. IL-18 also induce severe inflammatory reactions and plays a role in inflammatory and autoimmune disorders (such as adenomyosis Hashimoto's thyroiditis, and Alzheimer's disease). Examples of sequences are available in GENBANK® (e.g., Accession Nos. NP_001553.1 and NM_001562.4, incorporated by reference herein as available on Mar. 9, 2019, which provide exemplary protein and nucleotide sequences for IL-18, respectively). One of ordinary skill in the art can identify additional IL-18 nucleic acid and protein sequences, including IL-18 variants that retain IL-18 biological activity (such as pro-inflammatory activity).

Interleukin 21 (IL-21): Also known as CVID11 and Za11 (for example, OMIM 605384), IL-21 aids in regulating the immune system, for example, through natural killer (NK) cells, cytotoxic T cells, and cancerous cells. IL-21 is expressed in activated human CD4+ T cells and induces cell division/proliferation, regulates the body's response to viral infection in its target cells, alleviates allergies, is involved in the anti-tumor response. Examples of sequences are available in GENBANK® (e.g., Accession Nos. NP_068575.1 and NM_021803.4, incorporated by reference herein as available on Mar. 9, 2019, which provide exemplary protein and nucleotide sequences for IL-21, respectively). One of ordinary skill in the art can identify additional IL-21 nucleic acid and protein sequences, including IL-21 variants that retain IL-21 biological activity (such as immune system regulation activity).

Interleukin 22 (IL-22): Also known as interleukin 10-related T cell-derived inducible factor (ILTIF), IL-D110, IL-TIF, ILTIF, TIFIL-23, TIFa, and zcyto18 (e.g., OMIM 605330), IL-22 is produced by activated NK and T cells and is involved in the innate immune response, such as in epithelial cells, for example, respiratory and gut epithelial cells. IL-22 also aids in regulating autoimmunity and tissue regeneration. IL-22 contributes to immune disease through stimulating inflammatory responses, having both pro-inflammatory and tissue-protective functions. Examples of sequences are available in GENBANK® (e.g., Accession Nos. AAH70261.1 and NM_020525.5, incorporated by reference herein as available on Mar. 9, 2019, which provide exemplary protein and nucleotide sequences for IL-22, respectively). One of ordinary skill in the art can identify additional IL-22 nucleic acid and protein sequences, including IL-22 variants that retain IL-22 biological activity (such as pro-inflammatory and tissue-protective activity).

Interleukin 23 (IL-23): Also known as interleukin 23, p19 subunit, p19, and SGRF (e.g., OMIM 605580), IL-23 increases inflammation and facilitates autoimmune disease (such as multiple sclerosis, arthritis, intestinal inflammation, and psoriasis. IL-23 also aids in regulating the immune response, such as against viral, bacterial, and fungal infections. Examples of sequences are available in GENBANK® (e.g., Accession Nos. AAH67511.1 and NM_016584.3, incorporated by reference herein as available on Mar. 9, 2019, which provide exemplary protein and nucleotide sequences for IL-23, respectively). One of ordinary skill in the art can identify additional IL-23 nucleic acid and protein sequences, including IL-23 variants that retain IL-23 biological activity (such as pro-inflammatory activity).

Inflammation: A biological response to harmful stimuli, which is particular for the stimuli. Inflammation can be acute or chronic. Acute inflammation is the initial response to the stimuli, including increased movement of plasma and leukocytes (especially granulocytes) from the blood to injured tissues. Chronic inflammation (prolonged inflammation) is a progressive shift in the type of cells at the site of inflammation (such as an increase in mononuclear cells) and includes simultaneous destruction and healing of the inflamed tissue. Abnormalities in the inflammatory response can lead to disease (e.g., myopathies, cancer, and vascular and/or cardiovascular disease). Inflammation can be assessed in multiple ways (see, e.g., Cooper et al., Genome Biol., 6(1): R5, 2005; Newton and Dixit, Cold Spring Harb Perspect Biol, 4(3):pii: a006049, 2012, both of which are incorporated herein by reference, indicating various biomarkers relevant to assaying inflammation). In some examples, inflammation can be assessed by measuring levels of expression of tumor necrosis factor (TNF), interleukin (IL)-6, IL-1b, C-reactive protein (CRP), and/or adenomatous polyposis coli (APC) genes compared with a control subject (e.g., a subject without inflammation). "Ocular inflammation" is inflammation of the eye.

Inflammatory disease or disorder: A disorder that is caused by inflammation. Inflammation can lead to inflammatory or immune (such as autoimmune) diseases or disorders, such as rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, skin disorders (including dermatomyositis and psoriasis), and the like. Thus, some inflammatory disorders may also be characterized as immune disorders, such as autoimmune disorders.

Inhibiting or treating a disease: Inhibiting the full development of a disease or condition, for example, in a subject who is at risk for a disease, such as corneal haze or scarring, dry eye disease, or ocular inflammation. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well-known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated, produced apart from, or purified away from other biological components in the cell of the organism in which the component naturally occurs, such as other chromosomal and extrachromosomal DNA and RNA as well as proteins. Nucleic acids, peptides, and proteins that have been "isolated" thus include nucleic acids and proteins purified by standard purification methods. The term also embraces nucleic acids, peptides, and proteins prepared by recombinant expression in a host cell as well as chemically synthesized nucleic acids.

Jacalin (Jac): A lectin from jackfruit seeds that is both a potent T cell mitogen and an apparently T cell-independent activator of human B cells for the secretion of immunoglobulins. Jacalin is a D-Gal-binding lectin and belongs to a family of galactose-binding lectins containing the Jacalin-like lectin domain. The lectin is blood group non-specific after neuraminidase treatment and agglutinates human erythrocytes. Post-translational proteolytic modification of Jacalin yields a novel carbohydrate-binding site involving the N terminus of the a-chain. Jac sequences are publicly available. GENBANK® Accession Nos. AAA32680.1 and L03798.1, incorporated herein by reference as available on Mar. 9, 2018, provide exemplary jackfruit Jac protein and nucleotide sequences, respectively.

Lectins: Lectins are carbohydrate-binding proteins, macromolecules that are highly specific for sugar moieties and occur ubiquitously in nature. Most lectins do not possess enzymatic activity but may bind to a soluble carbohydrate or to a carbohydrate moiety that is a part of a glycoprotein or glycolipid; they typically agglutinate certain animal cells and/or precipitate glycoconjugates. Exemplary lectins include wheat germ agglutinin (WGA), concanavalin A (conA), and jacalin (Jac).

Linker: Linkers, or spacers, are short amino acid or nucleic acid sequences used to separate multiple domains in a single protein. Linkers can be rigid, for example, to prohibit unwanted interactions between discrete segments, such as protein domains. Other linkers can be flexible, connecting various segments in a single molecule, such as a protein or nucleic acid, without otherwise interfering with the function of the molecule. In specific examples, a linker can include SEQ ID NO: 9 or SEQ ID NO: 19.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction.

Further, "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Ocular surface: The surface of the eye, including the cornea, the conjunctiva, and the tear ducts which connect to them as well as the eyelids.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, e.g., Remington's Pharmaceutical Sciences, 1289-1329, 1990, incorporated herein by reference). Except insofar as any conventional carrier is incompatible with the active ingredient, its use in the therapeutic or pharmaceutical compositions is contemplated.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, pellet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound, biologic, or composition capable of inducing a desired therapeutic or prophylactic effect when properly administered to a subject or a cell.

Polypeptide: Three or more covalently attached amino acids. The term encompasses proteins, protein fragments, and protein domains. A "collagen-binding" polypeptide is a polypeptide with the ability to specifically bind collagen.

The term "polypeptide" is specifically intended to cover naturally occurring proteins, as well as those which are recombinantly or synthetically produced. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

Conservative amino acid substitutions are those substitutions that do not substantially affect or decrease a function of a protein, such as the ability of the protein to exert a synergistic effect in the treatment cancer when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well-known. The following six groups are examples of amino acids that are considered to be conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

Non-conservative substitutions are those that reduce an activity or function of the protein, such as the ability to induce a synergistic response when administered to a subject. For instance, if an amino acid residue is essential for a function of the protein, even an otherwise conservative substitution may disrupt that activity. Thus, a conservative substitution does not alter the basic function of a protein of interest.

Protein A refers to any form of protein A polypeptide or variation thereof that retains immunoglobulin-binding activity. For example, protein A may be a 42 kDa surface protein originally found in the cell wall of the bacteria *Staphylococcus aureus* and/or a recombinant protein that includes protein A or a variant thereof. Protein A of *Staphylococcus aureus* is encoded by the spa gene, and it is composed of five homologous Ig-binding domains that fold into a three-helix bundle, each domain of which can bind proteins from many mammalian species, most notably immunoglobulin G. Protein A is used in biochemical research because it can bind immunoglobulins; protein A binds the heavy chain within the Fc region of most immunoglobulins and within the Fab region of the human VH3 family. Examples of sequences are available in GENBANK® (e.g., Accession Nos. X61307.1 and AAB05743.1, incorporated by reference as available on Mar. 9, 2018, which provide exemplary nucleotide and protein sequences for protein A); other examples are available herein (e.g., SEQ ID NO: 9).

Protein G refers to any form of protein G polypeptide or variation thereof that retains immunoglobulin-binding activity. For example, protein G may be an immunoglobulin-binding protein expressed in group C and G Streptococcal bacteria, which, similar to protein A, has multiple homologous Ig-binding domains but with differing binding specificities and/or a recombinant protein that includes protein A or a variant thereof. Protein G can be a 65 kDa (G148 protein G) and a 58 kDa (C40 protein G) cell surface protein that can be used to purify antibodies through its binding to the Fab and Fc regions. Examples of sequences are available in GENBANK® (e.g., accession nos. Y00428.1 and CAA37410.1, incorporated by reference as available on Mar. 9, 2018, which provide exemplary nucleotide and protein sequences for protein A); other examples are available herein (e.g., SEQ ID NO: 10).

Protein L refers to any form of protein L polypeptide or variation thereof that retains immunoglobulin-binding activity. For example, protein L may be an antibody-binding protein expressed at the surface of approximately 10% of *Peptostreptococcus magnus* isolates that contains four or five Ig-binding domains that bind kappa light chains and/or a recombinant protein that includes protein A or a variant thereof. Examples of sequences are available in GEN-BANK® (e.g., accession nos. L04466.1 and AAA67503.1, incorporated by reference as available on Mar. 9, 2018, which provide exemplary nucleotide and protein sequences for protein A).

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides. A purified population of nucleic acids or proteins is greater than about 90%, 91%, 92%, 93%, 94%, 95%, 96%, 97%, 98%, 99%, or 100% pure, or free other nucleic acids or proteins, respectively.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well-known in the art. Various programs and alignment algorithms are described in Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA*, 85:2444, 1988; Higgins and Sharp, *Gene*, 73:237, 1988; Higgins and Sharp, *CABIOS*, 5:151, 1989; Corpet et al., *Nucleic Acids Research*, 16:10881, 1988; and Pearson and Lipman, *Proc. Natl. Acad. Sci. USA*, 85:2444, 1988. Altschul, et al., *Nature Genet.*, 6:119, 1994 presents a detailed consideration of sequence alignment methods and homology calculations.

The NCBI Basic Local Alignment Search Tool (BLAST) (Altschul, et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, sequence identity counted over the full length alignment with the amino acid sequence of the factor using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Sjögren's syndrome: A systemic autoimmune disease in which immune cells attack and destroy the exocrine glands that produce saliva and tears. The hallmark symptoms of the disorder are Xerostomia (dry mouth) and xerophthalmia (conjunctivitis sicca, dry eyes). Sjögren's syndrome can also cause skin, nose, and vaginal dryness, and can affect other organs of the body, including the kidneys, blood vessels, lungs, liver, pancreas, and brain. Sjögren's syndrome can occur in all age groups of both women and men. However, nine out of ten Sjögren's patients are women, with the average age of onset being in the late 40s. Sjögren's syndrome can occur independently, referred to as primary Sjögren's syndrome, or may develop years after the onset of an associated rheumatic disorder, referred to as secondary Sjögren's syndrome.

Xerostomia and xerophthalmia are usually the first detected symptoms of Sjögren's syndrome (Fox et al., *Lancet* 1, 1432-1435, 1985). It has been postulated that immunologically-activated or apoptotic glandular epithelial cells that expose autoantigens in predisposed individuals could drive autoimmune-mediated tissue injury (see, e.g., Voulgarelis et al., *Nat Rev Rheumatol,* 6, 529-537, 2010; Xanthou et al., *Clin Exp Immunol* 118, 154-163, 1999). Immune activation in this patient can present as focal, mononuclear (T cell, B cell, and macrophage) cell infiltrates proximal to the ductal epithelial cells (epithelitis) and forms sialadenitis. CD4+T-lymphocytes constitute 60-70 percent of the mononuclear cells infiltrating the salivary glands (Skopouli et al., *J Rheumatol,* 18, 210-214, 1991). Abnormal activation of proinflammatory Th1 (Bombardierei et al., *Arthritis Res Ther,* 6, R447-R456, 2004; Vosters et al., *Arthritis Rheum,* 60, 3633-3641, 2009) and Th17 (see, e.g., Nguyen et al., *Arthritis and Rheumatism,* 58, 734-743, 2008) cells have been reported in the human or condition and in animal models.

Small molecular weight compounds (small molecules): A low-molecular-weight (<900 daltons) organic compound that may help regulate a biological process. The upper molecular-weight limit for a small molecule is approximately 900 daltons, which allows for the possibility to rapidly diffuse across cell membranes so that they can reach intracellular sites of action. In addition, this molecular weight cutoff is a necessary but insufficient condition for oral bioavailability. This term can also include a molecule that binds to a specific biological target, such as a specific protein or nucleic acid, and acts as an effector, altering the activity or function of the target. Small molecules can have a variety of biological functions, serving as cell signaling molecules, drugs in medicine, pesticides in farming, and in many other roles.

Specifically binding agent: An agent (such as a protein or polypeptide) that binds substantially or preferentially only to a defined target, such as a protein (such as IL-9, IL-6, IL-1β, IL-1α, TNFα, IL-18, IFNγ, IL-12, GM-CSF, TGF-β, IL-21, IL-22, and IL-23), enzyme, polysaccharide, nucleic acid, or a small molecule. For example, an agent that specifically binds a protein binds substantially only the defined protein or to a specific region within the protein. For example, an "agent that specifically binds IL-9, IL-6, IL-1β, IL-1α, TNFα, IL-18, IFNγ, IL-12, GM-CSF, TGF-β, IL-21, IL-22, and IL-23" includes antibodies and other agents that bind substantially to IL-9, IL-6, IL-1β, IL-1α, TNFα, IL-18, IFNγ, IL-12, GM-CSF, TGF-β, IL-21, IL-22, and IL-23, respectively. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: As used herein, the term "subject" refers to a mammal and includes, without limitation, humans, domestic animals (e.g., dogs or cats), farm animals (e.g., cows, horses, or pigs), and laboratory animals (mice, rats, hamsters, guinea pigs, pigs, rabbits, dogs, or monkeys). In some examples, the term "subject" includes control subject, a subject in need of a treatment, a subject with a condition or disease, or a patient. In some embodiments, the patient or subject is an adult, child, or infant. In some embodiments, the patient or subject is a human.

Tumor necrosis factor (TNFα)-binding protein 1 (TBP1) refers to any form of TBP1. This is a soluble protein that is derived from a ubiquitous membrane receptor (e.g., tumor necrosis factor receptor 1) by proteolysis, and it binds TNFα.

TNFα: Tumor necrosis factor (TNF, tumor necrosis factor α, TNFα, cachexin, or cachectin) is a cell signaling protein (cytokine) involved in systemic inflammation and is one of the cytokines that make up the acute phase reaction. It is produced chiefly by activated macrophages, although it can be produced by many other cell types, such as CD4+ lymphocytes, NK cells, neutrophils, mast cells, eosinophils, and neurons. Exemplary protein and nucleotide sequences for TNFα are available at GENBANK® (e.g., Accession Nos. P01375.1 and NM_001199054.1, respectively, incorporated by reference herein as available on Mar. 9, 2018).

Transforming growth factor beta-receptor (TGFβr1): Also known as TGFBR1 and activing receptor-like kinase 5 (ALK5; e.g., OMIM 190181), TGFβr1 is a serine/threonine kinase receptor for transforming growth factor-beta (TGFβ). Inhibitors of TGFβr1 have been developed, including the peptides P17 and P144 (see Patent Pub. No. US20120315256, incorporated herein by reference).

Transforming growth factor β (TGFβ): Also known as TGFB1 (e.g., OMIM 190180), TGFβ is a cytokine in the TGF superfamily. Activated TGFβ activates different downstream substrates and regulatory proteins, inducing transcription of different target genes for cell differentiation, chemotaxis, proliferation, and activation of many immune cells. As TGFβ exhibits immunosuppressive functions, an increase in TGFβ expression often correlates with cancer malignancy, and disregulation of its immunosuppressive functions is implicated autoimmune diseases. Exemplary protein and nucleotide sequences for TGFβ are available at GENBANK® (e.g., Accession Nos. NP_000651.3 and NM_000660.6, respectively, incorporated by reference herein as available on Mar. 9, 2018).

Tear film: The layer of fluid including an aqueous layer covered by a lipid layer that covers the exposed area of the globe of the eye.

Therapeutic agent: The term "therapeutic agent" or "therapeutic," when used in a generic sense, includes treating agents, prophylactic agents, and replacement agents.

Therapeutic protein: A protein that achieves a desired effect when administered to a subject, such as in the eye of the subject. A therapeutic protein can have a direct effect, such as a cytokine or cytokine antibody, or an indirect effect, such as Protein A, Protein G, Protein L or similar proteins found on the surface of Gram-positive bacteria, which can bind a monoclonal or polyclonal antibody that has a desired therapeutic effect.

Therapeutically effective amount: The term "therapeutically effective amount" refers to that amount of an active ingredient (such as a fusion protein) that is sufficient to effect treatment when administered to a mammal in need of such treatment. The therapeutically effective amount will vary depending upon the subject and disease condition being treated, the weight and age of the subject, the severity of the disease condition, the manner of administration and the like, which can readily be determined by a prescribing physician.

Treating, treatment, and therapy: Any success or indicia of success in the attenuation or amelioration of an injury, pathology, or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or improving vision. The treatment may be assessed by objective or subjective parameters; including the results of a physical examination, neurological examination, or psychiatric evaluations.

Vascular endothelial growth factor A (VEGF-A): Also known as VEGF (e.g., OMIM 192240), VEGF-A is a pleiotropic cytokine. VEGF-A is linked to POEMS syndrome, also known as Crow-Fukase syndrome as well as proliferative and nonproliferative diabetic retinopathy. VEGF-A also has a cardiovascular and neuroprotective effect. Exemplary protein and nucleotide sequences for VEGF-A are available at GENBANK® (e.g., Accession Nos. AAH65522.2 and NM_015485.5, respectively, incorporated by reference herein as available on Mar. 9, 2019).

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating, or the like. A vector can be a viral vector.

von Willebrand factor (vWF): Also known as factor VIII-von Willebrand factor (F8VWF; e.g., OMIM 613160), vWF is a blood glycoprotein involved in hemostasis that includes a collagen-binding domain. vWF's primary function is binding to other proteins, in particular factor VIII, and it is important in platelet adhesion to wound sites. vWF has been shown to interact with collagen. vWF sequences are publicly available. For example, GENBANK® Accession Nos. AAB59458.1, AAP41950.1, and Q62935.2, incorporated by reference herein as available on Sep. 14, 2017, disclose exemplary human, rat, and mouse vWF protein sequences, and GENBANK® Accession Nos. NM_000552.4, AJ224673.1, and NM_011708.4, incorporated by reference herein as available on Mar. 9, 2018, disclose exemplary human, rat, and mouse vWF nucleotide sequences, respectively.

Wheat germ agglutinin (WGA): A lectin (carbohydrate-binding protein is a lectin that protects wheat (*Triticum vulgaris*) from insects, yeast, and bacteria. It binds to N-acetyl-D-glucosamine and Sialic acid. In mammals the N-acetyl-D-glucosamine that WGA binds to is found in cartilage and the cornea, among other places, and sialic acid is found in mucous membranes (e.g., the lining of the inner nose and digestive tract). Examples of sequences are available in GENBANK® (e.g., Accession Nos. AAA34256.1 and M25536.1, incorporated herein by reference as available on Mar. 9, 2018, which provide exemplary protein and nucleotide sequences for WGA, respectively); other examples are available herein (e.g., SEQ ID NO: 13).

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and, Harlow and Lane, *Using Antibodies: A Laboratory Manual*, Cold Spring Harbor Laboratory Press, 1999. In addition, the materials, methods, and examples are illustrative only and not intended to be limiting.

II. Fusion Protein

Local application of therapeutic compounds to a tissue of a human subject is especially challenging because the compounds are washed out too quickly in some tissues to have significant effects. Attaching a domain that anchors therapeutic proteins to the surface of a tissue, so they are retained on the tissue surface and, therefore, can act for prolonged periods of time presents a versatile solution that can be applied to treat many conditions. Methods and compositions are disclosed herein for a fusion protein that includes an anchor domain and a therapeutic protein. The methods and compositions described herein include administering the fusion protein in a pharmaceutical composition to a tissue of a subject, such as to treat inflammation.

The presently disclosed methods utilize fusion polypeptides comprising an anchor domain and a therapeutic protein. In some embodiments, the anchor protein includes a collagen-binding polypeptide, a heparin-binding polypeptide, or a lectin. In other embodiments, the therapeutic protein includes (1) an anti-inflammatory cytokine, such as interleukin (IL)-10, IL-1Ra, IL-6, IL-9, IL-21, IL-22, granulocyte-colony stimulating factor (G-CSF), vascular endothelial growth factor A (VEGF-A), IL-4, IL-5, IL-13, and transforming growth factor (TGF)β, or (2) an antagonist of or antibody that specifically binds a pro-inflammatory cytokine, such as IL-9, IL-6, IL-1β, IL-1α, tumor necrosis factor alpha (TNFα), IL-18, interferon (IFN)γ, IL-12, granulocyte-macrophage colony-stimulating factor (GM-CSF), TGFβ, IL-21, IL-22, IL-23, IL-4, IL-5, IL-13, IL-17F, IL-17A, and VEGF-A.

A. Anchor Domains

The disclosed fusion proteins include an anchor domain that allows the fusion protein to adhere to a tissue surface through non-covalent bonds. These anchor domains can bind collagen, heparin, heparan sulfate, or a carbohydrate.

Exemplary collagen-binding anchor domains from the von Willebrand factor (vWF) are found in GENBANK® Accession Nos. AAB59458.1, AAP41950.1, and Q62935.2, incorporated by reference herein as available on Sep. 14, 2017, and as follows:

```
                                    (SEQ ID NO: 1)
           WREPSFMALS (SEQ ID NO: 2)
           WREPSFCALS

Additional variants
of use are:
                                    (SEQ ID NO: 20)
           YREPSFMALS, (SEQ ID NO: 21)
           WKEPSFMALS, (SEQ ID NO: 22)
           WRDPSFMALS, (SEQ ID NO: 23)
           WREASFMALS, (SEQ ID NO: 24)
           WREPTFMALS, (SEQ ID NO: 25)
           WREPSYMALS,
or
                                    (SEQ ID NO: 26)
           WREPSFAALS.
```

An exemplary collagen-binding anchor domain from *Clostridium* collagenase (ColH) are found in GENBANK® Accession No. BAA06251.1, incorporated by reference herein as available on Mar. 9, 2018, and as follows:

```
                                           (SEQ ID NO: 3)
EIKDLSENKLPVIYMHVPKSGALNQKVVFYGKGTYDPDGSIAGYQWDFGD

GSDFSSEQNPSHVYTKKGEYTVTLRVMDSSGQMSEKTMKIKITDPVYPIG

TEKEPNNSKETASGPIVPGIPVSGTIENTSDQDYFYFDVITPGEVKIDIN

KLGYGGATWVVYDENNNAVSYATDDGQNLSGKFKADKPGRYYIHLYMFNG

SYMPYRINIEGSVGR
```

Exemplary heparin-binding (HS) anchor domains are as follows:

```
                                    (SEQ ID NO: 4)
           KRKKKGKGLGKKRDPSLRKYK (SEQ ID NO: 5)
           KRKKKGKGLGKKRDPCLRKYK
```

Carbohydrate-binding anchor domains include lectins and fragments thereof. Exemplary lectins are wheat germ agglutinin (WGA), concanavalin A (conA), and jacalin (Jac). An exemplary carbohydrate-binding anchor domain from ConA is:

```
(GENBANK ® Accession No: CAA25787.1,
incorporated by reference herein as
available on Mar. 9, 2019)
                                           (SEQ ID NO: 6)
MAISKKSSLFLPIFTFITMFLMVVNKVSSSTHETNALHFMFNQFSKDQKD

LILQGDATTGTDGNLELTRVSSNGSPQGSSVGRALFYAPVHIWESSAVVA

SFEATFTFLIKSPDSHPADGIAFFISNIDSSIPSGSTGRLLGLFPDANVI

RNSTTIDFNAAYNADTIVAVELDTYPNTDIGDPSYPHIGIDIKSVRSKKT

AKWNMQNGKVGTAHIIYNSVDKRLSAVVSYPNADSATVSYDVDLDNVLPE

WVRVGLSASTGLYKETNTILSWSFTSKLKSNEIPDIATVV
```

An exemplary carbohydrate-binding anchor domain from WGA is:

```
(GENBANK ® Accession Nos.: AAA34256.1,
AAA34258.1, and AAA34257.1, incorporated
by reference herein as available on
Mar. 9, 2018)
                                           (SEQ ID NO: 7)
MKMMSTRALALGAAAVLAFAAATAQAQRCGEQGSNMECPNNLCCSQYGYC

GMGGDYCGKGCQNGACWTSKRCGSQAGGATCTNNQCCSQYGYCGFGAEYC

GAGCQGGPCRADIKCGSQAGGKLCPNNLCCSQWGFCGLGSEFCGGGCQSG

ACSTDKPCGKDAGGRVCTNNYCCSKWGSCGIGPGYCGAGCQSGGCDGVFA

EAITANSTLLQE
```

An exemplary carbohydrate-binding anchor domain from Jac is:

```
(GENBANK ®: AAA32680.1, incorporated
by reference herein as available on
Mar. 9, 2018)
                                           (SEQ ID NO: 8)
MAYSSLLSLSVLALLFSISSADTRKWFLANGINQNPIGIIEAAVGVSEDL

LNLNGMEAKNDEQSGISQTVIVGPWGAKVSTSSNGKAFDDGAFTGIREIN

LSYNKETAIGDFQVVYDLNGSPYVGQNHKSFITGFTPVKISLDFPSEYIM

EVSGYTGNVSGYVVVRSLTFKTNKKTYGPYGVTSGTPFNLPIENGLIVGF

KGSIGYWLDYFSMYLSL
```

One of skill in the art can readily identify fragments and variants of these anchor domains, see below. The anchor domain can be directly bound to a therapeutic polypeptide, or a linker can be inserted between the anchor domain and the therapeutic polypeptide.

In some examples, the anchor domain can be directly bound to a therapeutic polypeptide, such as by a covalent bond between amino acids of the anchor domain and therapeutic peptide. The anchor domain can be directly bound to a therapeutic polypeptide by binding at either or both termini of the anchor domain or therapeutic peptide, between side chains of amino acids of the anchor domain and therapeutic peptide, or between a side chain of the anchor domain or therapeutic peptide and a terminus of the anchor domain or therapeutic peptide.

In some examples, a linker can be inserted between the anchor domain and the therapeutic polypeptide. In some embodiments, the linker may be a amino acid sequence (such as a non-biologically active amino acid sequence) that connects the anchor domain and therapeutic peptide, for example, without affecting secondary and/or tertiary structures of these components of the fusion protein. The linker can link the anchor domain in a N-terminal to C-terminal order or a C-terminal to N-terminal order. In some embodiments, the linker may produce a curve that can set anchor domain and therapeutic peptide as a specific angle to one another and/or position active sites on the anchor domain and therapeutic peptide on particular faces of the fusion protein. Exemplary linkers are set forth below:

(SEQ ID NO: 9)
GGGGS (SEQ ID NO: 19)
EAAAKEAAAK

B. Therapeutic Polypeptides

The disclosed fusion proteins include a therapeutic polypeptide. In some embodiments, the therapeutic polypeptide can be, for example, administering to the tissue of the subject a therapeutically effective amount of the fusion protein of claim 1, wherein the therapeutic polypeptide comprises at least one of (1) an anti-inflammatory cytokine, such as interleukin (IL)-10, IL-1Ra, IL-6, IL-9, IL-21, IL-22, granulocyte-colony stimulating factor (G-CSF), vascular endothelial growth factor A (VEGF-A), IL-4, IL-5, IL-13, and transforming growth factor (TGF)β, or (2) an antagonist of or antibody that specifically binds a pro-inflammatory cytokine, such as IL-9, IL-6, IL-1β, IL-1α, tumor necrosis factor alpha (TNFα), IL-18, interferon (IFN) γ, IL-12, granulocyte-macrophage colony-stimulating factor (GM-CSF), TGFβ, IL-21, IL-22, IL-23, IL-4, IL-5, IL-13, IL-17F, IL-17A, and VEGF-A. In exemplary embodiments, the therapeutic polypeptide includes IL-10, IL-1Ra, IL-6, IL-9, IL-21, IL-22, G-CSF, TGFβ, P17, P144, a TNF receptor 1 polypeptide (such as TBP1), IL-4, IL-5, IL-13, or VEGF-A. In some exemplary embodiments, the therapeutic polypeptide includes an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17A, or VEGF-A. In some exemplary embodiments, the therapeutic polypeptide includes an immunoglobulin-binding (Ig) polypeptide and/or an antibody that specifically binds IFNγ, protein A, protein G, and/or protein L. In specific examples, the antagonist is not an antibody, or is a non-antibody antagonist.

One of skill in the art can readily identify therapeutic polypeptides of use. In some embodiments, the therapeutic protein is IL-10. An amino acid sequence for human IL-10 and a cDNA encoding this amino acid sequence are provided in GENBANK® Accession Nos. NP_000563.1 and CR542028, respectively, each of which are incorporated by reference herein as available on Sep. 14, 2017. A murine IL-10 and a cDNA encoding this amino acid sequence are provided in GENBANK® Accession Nos. EDL39722.1 and MUSIL10Z, respectively, each of which are incorporated by reference herein as available on Sep. 14, 2017, see also Fujio, K. et al., *Adv Immunol*, 105:99-130, 2010, incorporated herein by reference.

In some embodiments, the therapeutic protein is protein A. An exemplary protein A immunoglobulin-binding polypeptide is:

(SEQ ID NO: 10)
ADNKFNKEQQNAFYEILHLPNLNEEQRNGFIQSLKDDPSQSANLLAEAKK

LNDAQAPKADNKFNKEQQNAFYEILHLPNLTEEQRNGFIQSLKDDPSVSK

EILAEAKKLNDAQAPK

Further, an amino acid sequence for *Staphylococcus aureus* protein A and a cDNA encoding this amino acid sequence are provided in GENBANK® Accession No. X61307.1, incorporated by reference herein as available on Mar. 9, 2018.

In some embodiments, the therapeutic protein is protein G. An exemplary protein G immunoglobulin-binding polypeptide is:

(SEQ ID NO: 11)
KTFTVTEKPEVIDASELTPAVTTYKLVINGKTLKGETTTKAVDAETAEKA

FKQYANDNGVDGVWTYDDATKTFTVTE

Further, an amino acid sequence for *Streptococcus* sp. GX7805 protein G and a cDNA encoding this amino acid sequence are provided in GENBANK® Accession No. Y00428.1, incorporated by reference herein as available on Mar. 9, 2018.

In some embodiments, the therapeutic protein is protein L. An amino acid sequence for *Finegoldia magna* protein L and a cDNA encoding this amino acid sequence are provided in GENBANK® Accession No. M86697.1, incorporated by reference herein as available on Mar. 9, 2018.

In some embodiments, the therapeutic protein is an inhibitor of TNFα polypeptide from the TNF receptor 1. An exemplary polypeptide sequence of this inhibitor is:

(SEQ ID NO: 12)
DSVCPQGKYIHPQNNSICCTKCHKGTYLYNDCPGPGQDTDCRECESGSFT

ASENHLRHCLSCSKCRKEMGQVEISSCTVDRDTVCGCRKNQYRHYWSENL

FQCFNCSLCLNGTVHLSCQEKQNTVCTCHAGHLRENECVSCSNCKKSLEC

TKLCLPQIEN

Further, an amino acid sequence for a human inhibitor of TNFα polypeptide from the TNF receptor 1 and a cDNA encoding this amino acid sequence are provided in GENBANK® Accession Nos. NP_001056 and NG_007506, respectively, incorporated by reference herein as available on Mar. 9, 2018.

In some embodiments, the therapeutic protein is an inhibitor of TGFβ. For example, the inhibitor can include amino acids 730 to 743 of the type III receptor of human TGFβ1. Amino acid sequences for human and rat inhibitors of TGFβ1 (such as P144) are provided in U.S. Pat. No. 7,582,609, which is incorporated herein by reference. For example, the protein can include the sequence TSLDASII-WAMMQN (SEQ ID NO: 13). Amino acid sequences for inhibitors of TGFβ1 (such as P17) are provided in U.S. Pat. Pub. No. 2010/022280, which is incorporated herein by reference. For example, the protein can include the sequence KRIWFIPRSSWYERA (SEQ ID NO: 14).

In some embodiments, the therapeutic protein is IL-1Ra. Exemplary sequences for IL-1Ra are known in the art. For example, protein and nucleotide sequences for IL-1Ra are available at GENBANK® (e.g., Accession Nos. CAA36262.1 and AJ005835.1, respectively, incorporated by reference herein as available on Mar. 9, 2018).

In some embodiments, the therapeutic protein is IL-6. Exemplary sequences for IL-6 are known in the art. For example, protein and nucleotide sequences for IL-6 are available at GENBANK® (e.g., Accession Nos. P05231.1 and NM_001318095.1, respectively, incorporated by reference herein as available on Mar. 9, 2019).

In some embodiments, the therapeutic protein is IL-9. Exemplary sequences for IL-9 are known in the art. For example, protein and nucleotide sequences for IL-9 are available at GENBANK® (e.g., Accession Nos. AAC17735.1 and NM_000590.1, respectively, incorporated by reference herein as available on Mar. 9, 2019).

In some embodiments, the therapeutic protein is IL-21. Exemplary sequences for IL-21 are known in the art. For example, protein and nucleotide sequences for IL-21 are available in GENBANK® (e.g., Accession Nos. NP_068575.1 and NM_021803.4, incorporated by reference herein as available on Mar. 9, 2019).

In some embodiments, the therapeutic protein is IL-22. Exemplary sequences for IL-22 are known in the art. For example, protein and nucleotide sequences for IL-22 are available in GENBANK® (e.g., Accession Nos. AAH70261.1 and NM_020525.5, incorporated by reference herein as available on Mar. 9, 2019).

In some embodiments, the therapeutic protein is G-CSF. Exemplary sequences for G-CSF are known in the art. For example, protein and nucleotide sequences for G-CSF are available in GENBANK® (e.g., Accession Nos. NP_000750.1 and NM_000759.3, incorporated by reference herein as available on Mar. 9, 2019).

In some embodiments, the therapeutic protein is TGFβ. Exemplary sequences for TGFβ are known in the art. For example, protein and nucleotide sequences for TGFβ are available at GENBANK® (e.g., Accession Nos. NP_000651.3 and NM_000660.6, respectively, incorporated by reference herein as available on Mar. 9, 2018).

In some embodiments, the therapeutic protein is VEGF-A. Exemplary sequences for VEGF-A are known in the art. For example, protein and nucleotide sequences for VEGF-A are available at GENBANK® (e.g., Accession Nos. AAH65522.2 and NM_015485.5, respectively, incorporated by reference herein as available on Mar. 9, 2019).

In some embodiments, the therapeutic protein is IL-4. Exemplary sequences for IL-4 are known in the art. For example, protein and nucleotide sequences for IL-4 are available at GENBANK® (e.g., Accession Nos. P05112.1 and MH644812.1, respectively, incorporated by reference herein as available on Mar. 9, 2019).

In some embodiments, the therapeutic protein is IL-5. Exemplary sequences for IL-5 are known in the art. For example, protein and nucleotide sequences for IL-5 are available at GENBANK® (e.g., Accession Nos. NP_000870.1 and NM_000879.3, respectively, incorporated by reference herein as available on Mar. 9, 2019).

In some embodiments, the therapeutic protein is IL-13. Exemplary sequences for IL-13 are known in the art. For example, protein and nucleotide sequences for IL-13 are available at GENBANK® (e.g., Accession Nos. AAH96141.2 and U31120.1, respectively, incorporated by reference herein as available on Mar. 9, 2019).

In some embodiments, the therapeutic protein is an antibody that specifically binds TGFβ. These antibodies are known in the art. Exemplary amino acid sequences for antibodies that specifically bind TGFβ1 are provided in U.S. Pat. No. 7,527,791 and include the 1D11 anti-TGFβ antibody (such as in Biswas et al., PLoS One. 6(11): e27090, 2011), which are incorporated herein by reference in their entireties.

In some embodiments, the therapeutic protein is an antibody that specifically binds TNFα. Exemplary amino acid sequences for antibodies that specifically bind TNFα are provided in U.S. Pat. No. 6,258,562 and include XT22 anti-TNFα antibody (Invitrogen®), which are incorporated herein by reference in their entireties.

In some embodiments, the therapeutic protein is an antibody that specifically binds IL-1β. These antibodies are known in the art. Exemplary amino acid sequences for antibodies that specifically bind IL-1β are provided in U.S. Pat. No. 8,623,367 and include the MM425B anti-IL-1β antibody (Invitrogen®), which are incorporated herein by reference in their entireties.

In some embodiments, the therapeutic protein is an antibody that specifically binds IL-6. These antibodies are known in the art. Exemplary amino acid sequences for antibodies that specifically bind IL-6 are provided in U.S. Pat. No. 7,291,721 and include the anti-IL-6 MPS-20F3 antibody (R&D Systems), which are incorporated herein by reference in their entireties.

In some embodiments, the therapeutic protein is an antibody that specifically binds IL-17A. These antibodies are known in the art. Exemplary amino acid sequences for antibodies that specifically bind IL-17A are provided in U.S. Pat. No. 7,838,638 and include the TC11-18H10.1 anti-IL-17A antibody (Biolegend), which are incorporated herein by reference in their entireties.

In some embodiments, the therapeutic protein is an antibody that specifically binds IFNγ. These antibodies are known in the art. Exemplary amino acid sequences for antibodies that specifically bind IFNγ are provided in U.S. Pat. No. 7,084,257, which is incorporated herein by reference.

In some embodiments, the therapeutic protein is an antibody that specifically binds IL-9. These antibodies are known in the art. Exemplary amino acid sequences for antibodies that specifically bind IL-9 are provided in U.S. Pat. Pub. No. 2005/0002934, which is incorporated herein by reference.

In some embodiments, the therapeutic protein is an antibody that specifically binds IL-1α. These antibodies are known in the art. Exemplary amino acid sequences for antibodies that specifically bind IL-1α are provided in U.S. Pat. Pub. No. 2012/0275996 and include the MAB4001 anti-IL-1α antibody (R&D Systems), which are incorporated herein by reference in their entireties.

In some embodiments, the therapeutic protein is an antibody that specifically binds IL-18. These antibodies are known in the art. Exemplary amino acid sequences for antibodies that specifically bind IL-18 are provided in U.S. Pat. Pub. No. 2005/0147610, which is incorporated herein by reference.

In some embodiments, the therapeutic protein is an antibody that specifically binds IFNγ. These antibodies are known in the art. Exemplary amino acid sequences for antibodies that specifically bind IFNγ are provided in U.S. Pat. Pub. No. 2006/109191, which is incorporated herein by reference.

In some embodiments, the therapeutic protein is an antibody that specifically binds IL-12. These antibodies are known in the art. Exemplary amino acid sequences for antibodies that specifically bind IL-12 are provided in U.S. Pat. No. 6,914,128, which is incorporated herein by reference.

In some embodiments, the therapeutic protein is an antibody that specifically binds GM-CSF. These antibodies are known in the art. Exemplary amino acid sequences for antibodies that specifically bind GM-CSF are provided in Int. Pat. Pub. No. WO2006/122797, which is incorporated herein by reference.

In some embodiments, the therapeutic protein is an antibody that specifically binds IL-21. These antibodies are known in the art. Exemplary amino acid sequences for antibodies that specifically bind IL-21 are provided in Int. Pat. Pub. No. WO2010/055366, which is incorporated herein by reference.

In some embodiments, the therapeutic protein is an antibody that specifically binds IL-22. These antibodies are known in the art. Exemplary amino acid sequences for antibodies that specifically bind IL-22 are provided in Int. Pat. Pub. No. WO2005/000897, which is incorporated herein by reference.

In some embodiments, the therapeutic protein is an antibody that specifically binds IL-23. These antibodies are known in the art. Exemplary amino acid sequences for antibodies that specifically bind IL-23 are provided in U.S. Pat. No. 7,491,391, which is incorporated herein by reference.

In some embodiments, the therapeutic protein is an antibody that specifically binds VEGF-A. These antibodies are known in the art. Exemplary amino acid sequences for antibodies that specifically bind VEGF-A are provided in Int. Pat. Pub. No. WO2007/140534, which is incorporated herein by reference.

In some embodiments, the therapeutic protein is an antibody that specifically binds IL-4. These antibodies are known in the art. Exemplary amino acid sequences for antibodies that specifically bind IL-4 are provided in U.S. Pat. No. 5,705,154, which is incorporated herein by reference.

In some embodiments, the therapeutic protein is an antibody that specifically binds IL-5. These antibodies are known in the art. Exemplary amino acid sequences for antibodies that specifically bind IL-5 are provided in U.S. Pat. Pub. No. 2003/0194404, which is incorporated herein by reference.

In some embodiments, the therapeutic protein is an antibody that specifically binds IL-13. These antibodies are known in the art. Exemplary amino acid sequences for antibodies that specifically bind IL-13 are provided in U.S. Pat. No. 7,915,388, which is incorporated herein by reference.

In some embodiments, the therapeutic protein is an antibody that specifically binds IL-17F. These antibodies are known in the art. Exemplary amino acid sequences for antibodies that specifically bind IL-17F are provided in U.S. Pat. No. 7,790,163, which is incorporated herein by reference.

Peptides that are similar to the anchor domains, therapeutic polypeptides, and linkers disclosed above can be used as well as fragments thereof that retain the therapeutic activity. These anchor domains and therapeutic polypeptides may contain substitutions, deletions, or additions. The differences are preferably in regions that are not significantly conserved among different species. Such regions can be identified by aligning the amino acid sequences of related proteins from various animal species. Generally, the biological effects of the peptide are retained. For example, a polypeptide at least 75%, 80%, 85%, 90%, 95%, 96%, 97%, 98%, or 99% identical to one of these polypeptides can be utilized. Polypeptides are of use that include at most 1, 2, 3, 4, 5, 6, 7, 8, 9, or 10 conservative amino acid substitutions. Generally, polypeptides are of use provided they retain at least 75%, 80%, 85%, 90%, 95%, 96%, 97%, 98%, or 99% of the biological function of the native polypeptide, or have increased biological function as compared to the native polypeptide.

In some embodiments, a fragment of the therapeutic protein is utilized. Generally a fragment of use retains at least 75%, 80%, 85%, 90%, 95%, 96%, 97%, 98%, or 99% of the biological function of the native polypeptide, or has increased biological function as compared to the native polypeptide.

C. Fusion Proteins

A fusion protein of use in the methods disclosed herein includes at least two components: an anchor domain and a therapeutic protein. In some embodiments, the anchor domain can be attached to the therapeutic protein by a linker polypeptide, such as a GGGGS linker (SEQ ID NO: 9). In one embodiment, the therapeutic protein includes, in N-terminal to C-terminal order, the anchor domain and the therapeutic polypeptide. In another embodiment, the therapeutic protein includes, in N terminal to C-terminal order, the therapeutic polypeptide and the anchor domain. In either of these embodiments, a linker can be included between the anchor domain and the therapeutic polypeptide. Optionally, other components can be included at the N or C terminus, such as labels or a domain used for solubility and/or purification. In other embodiments, the fusion protein can include one or more copies of an anchor domain, therapeutic polypeptide (e.g., one of more copies of P144 or P17, such as at least about 1, 2, 3, 4, or 5 copies of P144 or P17 or about 2 copies of P144 or P17), or linker (e.g., one or more copies of SEQ ID NO: 9 or SEQ ID NO: 19, such as at least about 1, 2, 3, 4, or 5 copies of SEQ ID NO: 9 or SEQ ID NO: 19 or about 2 copies of SEQ ID NO: 9 or SEQ ID NO: 19). Additional information on therapeutic polypeptides and fusion proteins is provided below.

Also encompassed herein are therapeutic polypeptides that are fused to a heterologous peptide, such as a peptide that can be used for detecting; purifying; stabilizing; or solubilizing the polypeptide. In particular non-limiting examples, a solubilization domain can be included, such as to enhance solubility. Suitable solubilization domains include a maltose binding protein and the small ubiquitin-like modifier (SUMO).

In some embodiments, the fusion protein includes a collagen-binding domain, such as a collagen-binding polypeptide from von Willebrand factor (vWF) or *Clostridium* collagenase (ColH) and a therapeutically effective, Ig-binding polypeptide from protein A, protein G, and/or protein L. The Ig-binding polypeptide can include the entire protein A, protein G, and/or protein L or an Ig-binding fragment thereof. Exemplary polypeptides that include a protein G polypeptide as the Ig-binding polypeptide and a vWF polypeptide as the anchor domain are as follows:

MWREPSFMALSAS<u>GGGGSGGGGSAS</u>MGTPAVTTYKLVINGKTLKGETTTK

AVDAETAEKAFKQYANDNGVDGVWTYDDATKTFTVTEVNTPAVTTYKLVI

NGKTLKGETTTKAVDAETAEKAFKQYANDNGVDGVWTYDDATKTFTVTEI

GENLYFQGIDENLYFQGGSHHHHHH (SEQ ID NO: 15; linkers are underlined)

MSKKHHHHHHH<u>GGGGSAS</u>MGTPAVTTYKLVINGKTLKGETTTKAVDAET

AEKAFKQYANDNGVDGVWTYDDATKTFTVTEVNTPAVTTYKLVINGKTLK

GETTTKAVDAETAEKAFKQYANDNGVDGVWTYDDATKTFTVTEIGENLYF

QGIDENLYFQGGSAGGGGSGGGGSASWREPSFMALS (SEQ ID NO:

16, linkers are underlined)

In other embodiments, the therapeutically effective polypeptide can be a polypeptide from an inhibitor of TNFα polypeptide from the TNF receptor 1 or an inhibitor of TGFβ. The polypeptide from an inhibitor of TNFα polypeptide from the TNF receptor 1 or an inhibitor of TGFβ can include the entire inhibitor protein or a therapeutically effective fragment thereof. In some examples, the anchor domain can be a vWF polypeptide, and the therapeutic polypeptide can be an inhibitor of TGFβ. Exemplary polypeptides that include tandem repeats of P144 and P17, respectively, as the inhibitor and a vWF polypeptide as the anchor domain are as follows:

MSKKWREPSFMALSAS<u>GGGGSGGGGS</u>EAAAKTSLDASIIWAMMQN<u>EAAAK</u>

<u>EAAAK</u>TSLDASIIWAMMQN<u>GGGGS</u>HHHHHHHH (SEQ ID NO: 17;

linkers are underlined)

MSKKWREPSFMALSAS<u>GGGGSGGGGSGGGGS</u>KRIWFIPRSSWYERA<u>GGGG</u>

<u>SGGGGS</u>KRIWFIPRSSWYERA<u>GGGGS</u>HHHHHHHH (SEQ ID NO: 18;

linkers are underlined)

In additional embodiments, the fusion protein includes a collagen-binding domain, such as a collagen-binding polypeptide from von Willebrand factor (vWF) or *Clostridium* collagenase (ColH) or a heparin sulfate-binding domain and a therapeutically effective polypeptide from IL-10. The polypeptide from IL-10 can include the entire IL-10 protein or a therapeutically effective fragment thereof.

In some embodiments, the fusion protein includes a carbohydrate-binding anchor domain from lectins and fragments thereof. In specific examples of fusion proteins, wheat germ agglutinin (WGA) is fused to a therapeutically effective antibody against IL-17A (such as TC11-18H10.1 anti-IL-17A antibody (Biolegend)).

In some embodiments, the fusion protein includes a carbohydrate-binding anchor domain from lectins and fragments thereof. In specific examples of fusion proteins, wheat germ agglutinin (WGA) is fused to a therapeutically effective antibody against IL-17A (such as MM425B anti-IL-1β antibody (Invitrogen®)).

Also included are peptide derivatives of the anchor domains, therapeutically effective polypeptide, and/or fusion protein, which are differentially modified during or after synthesis, such as by benzylation, glycosylation, acetylation, phosphorylation, amidation, PEGylation, or derivatization by known protecting/blocking groups. For example PEGylation can be used to increase half-life of biologicals (Turecek P. L. et al. (2016) J. Pharm. Sci. 105, 460-475), and amidation can improve biological properties of drugs (Pan, Y. et al. (2007), 229-34)

In some embodiments, the anchor domain or therapeutic peptides can be peptidomimetics or include elements of peptidomimetics, such as non-naturally occurring amino acids, D stereoisomers of naturally occurring amino acids, or non-α amino acids. Various examples of non-naturally occurring amino acids are known in the art and can be included in either or both of the anchor domain and the therapeutic peptides of fusion protein of embodiments. In some embodiments, peptides can include at least one amino acid or every amino acid that is a D stereoisomer. Other peptides can include at least one amino acid that is reversed. The amino acid that is reversed may be a D stereoisomer. Every amino acid of a peptide may be reversed and/or every amino acid can be a D stereoisomer.

Any of the disclosed anchor domains, therapeutically effective polypeptides, or fusion proteins can be readily synthesized by automated solid phase procedures well-known in the art. Techniques and procedures for solid phase synthesis are described in Solid *Phase Peptide Synthesis: A Practical Approach*, by E. Atherton and R. C. Sheppard, published by IRL, Oxford University Press, 1989. Alternatively, these peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116: 4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing peptides of the present disclosure are described in Nakagawa et al., *J. Am. Chem. Soc.* 107:7087-7092, 1985.

D. Polynucleotides and Host Cells

Polynucleotides encoding the fusion proteins disclosed herein are also provided. These polynucleotides include DNA, cDNA, and RNA sequences, which encode the fusion protein. The coding sequence includes variants that result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, *Biochemistry*, 3.sup.rd Edition, W.H. 5 Freeman and Co., NY).

A nucleic acid encoding the fusion protein can be cloned or amplified by in vitro methods, such as the polymerase chain reaction (PCR), the ligase chain reaction (LCR), the transcription-based amplification system (TAS), the self-sustained sequence replication system (3SR), and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well-known to persons skilled in the art. PCR methods are described in, for example, U.S. Pat. No. 4,683,195; Mullis et al., Cold Spring Harbor *Symp. Quant. Biol.* 51:263, 1987; and Erlich, ed., *PCR Technology*, (Stockton Press, N Y, 1989). Polynucleotides also can be isolated by screening genomic or cDNA libraries with probes selected from the sequences of the desired polynucleotide under stringent hybridization conditions.

A polynucleotide sequence encoding the fusion protein can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, a ribosome binding site, transcription terminators, transcriptional regulators (e.g., AraC and LacI) a start codon (e.g., ATG) in front of a protein-encoding gene, splicing signal for introns, maintenance of the correct reading frame of that gene to permit proper translation of mRNA, and stop codons.

The polynucleotides encoding the fusion protein include a recombinant DNA, which is incorporated into a vector in an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

In one embodiment, vectors are used for expression in yeast, such as *Saccharomyces cerevisiae* or *Kluyveromyces lactis*. Several promoters are known to be of use in yeast expression systems such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. The polynucleotides can also be designed to express in insect cells.

The fusion protein can be expressed in a variety of yeast strains. For example, seven pleiotropic drug-resistant transporters, YOR1, SNQ2, PDR5, YCF1, PDR10, PDR11, and PDR15 together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the fusion protein disclosed herein. A number of viral vectors have been constructed, including polyoma, SV40 (Madzak et al., *J. Gen. Virol.*, 73:15331536, 1992), adenovirus (Berkner, *Cur. Top. Microbiol. Immunol.*, 158:39-6, 1992; Berliner et al., *Bio Techniques*, 6:616-629, 1998; Gorziglia et al., *J. Virol.*, 66:4407-4412, 1992; Quantin et al., *Proc. Nad. Acad. Sci. USA*, 89:2581-2584, 1992; Rosenfeld et al., *Cell*, 68:143-155, 1992; Wilkinson et al., *Nucl. Acids Res.*, 20:2233-2239, 1992; Stratford-Perricaudet et al., *Hum. Gene Ther.*, 1:241-256, 1990), vaccinia virus (Mackett et al., *Biotechnology*, 24:495-499, 1992), adeno-associated virus (Muzyczka, *Curr. Top. Microbiol. Immunol.*, 158:91-123, 1992; On et al., *Gene*, 89:279-282, 1990), herpes viruses including HSV and EBV (Margolskee, *Curr. Top. Microbiol. Immunol.*, 158:67-90, 1992; Johnson et al., *J. Virol.*, 66:29522965, 1992; Fink et al., *Hum. Gene Ther.* 3:11-19, 1992; Breakfield et al., *Mol. Neurobiol.*, 1:337-371, 1978; Fresse et al., *Biochem. Pharmacol.*, 40:2189-2199, 1990), Sindbis viruses (H. Herweijer et al., *Human Gene Therapy*, 6:1161-1167, 1995; U.S. Pat. Nos. 5,091,309 and 5,2217,879), alphaviruses (S. Schlesinger, *Trends Biotechnol.* 11:18-22, 1993; I. Frolov et al., *Proc. Natl. Acad. Sci. USA*, 93:11371-11377, 1996) and retroviruses of avian (Brandyopadhyay et al., *Mol. Cell Biol.*, 4:749-754, 1984; Petropouplos et al., *J. Virol.*, 66:3391-3397, 1992), murine (Miller, *Curr. Top. Microbiol. Immunol.*, 158:1-24, 1992; Miller et al., *Mol. Cell Biol.*, 5:431-437, 1985; Sorge et al., *Mol. Cell Biol.*, 4:1730-1737, 1984; Mann et al., *J. Virol.*, 54:401-407, 1985), and human origin (Page et al., *J. Virol.*, 64:5370-5276, 1990; Buchschalcher et al., *J. Virol.*, 66:2731-2739, 1992). Baculovirus (*Autographa californica* multinuclear polyhedrosis virus; AcMNPV) vectors are also known in the art and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a fusion protein is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors, and poliovirus vectors.

DNA sequences encoding the fusion protein can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts cells also can include microbial, insect, and mammalian host cells. Methods of expressing DNA sequences having eukaryotic or viral sequences in prokaryotes are well-known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), *Methods in Enzymology: Cell Culture*, volume 58, Academic Press, Inc., Harcourt Brace Jovanovich, N.Y., 1979). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods, *Methods in Enzymology*, 350: 87-96, 2002).

Transformation of a host cell with recombinant DNA can be carried out by conventional techniques as are well-known to those skilled in the art. Where the host is prokaryotic, such as, but not limited to, *E. coli*, competent cells that are capable of DNA uptake can be prepared from cells harvested after exponential growth phase and subsequently treated by the CaCl$_2$ method using procedures well-known in the art. Alternatively, MgCl$_2$ or RbCl can be used. Transformation can also be performed after forming a protoplast of the host cell, if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a C-terminal endostatin polypeptide and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see, for example, *Eukaryotic Viral Vectors*, Cold Spring Harbor Laboratory, Gluzman ed., 1982).

The fusion proteins herein can include a variety of additional amino acid or nucleic acid sequences available in the art, for example, to provide a label, enhance solubility, aid in protein purification, or any combination thereof. Therefore the additional amino acid or nucleic acid sequences can include a label, solubility enhancing sequence, purification tag, or combinations thereof, such as glutathione S-transferase, FLAG, or galactose binding domain (such as in Kimple et al., Curr Protoc Protein Sci., 73:Unit 9.9, 2013). Further included are post-translational modifications to at least one of the amino acids of the fusion proteins herein (such as post-translational modification of the anchor domain and/or therapeutic peptide). Examples of post-translational modifications include benzyl, glycosyl, acetyl, phosphoryl, amide, and PEG modifications, and combinations thereof. In specific examples, at least one amino acid is PEGylated, such as to increase the half-life of the fusion protein (such as in Turecek et al., J. Pharm. Sci., 105, 460-475, 2016). In specific example, at least one amino acid is amidated, for example to improve biological properties of the fusion protein.

E. Chemical Conjugation

While molecular methods can be used to synthesize fusion proteins, chemical methods can alternatively be used to synthesize fusion protein by linking an anchor domain to a therapeutic polypeptide. In some examples, an anchor domain (e.g., a lectin carbohydrate-binding domain, such as WGA, conA, and Jac, or a collagen- or heparin-binding domain) can be covalently bound to a therapeutic polypeptide (e.g., an Ig-binding polypeptide or a TGFβ antagonist, a TNFα antagonist, an IL-1β antagonist, an IL-6 antagonist, or an IFNγ antagonist) through chemical conjugation. Various types of chemical reagents can be used (see, e.g., Ido et al., JBC, 287(31): 26377-26387, 2012, and U.S. Pat. Pub. No. 2003/0040496, both incorporated herein by reference). In some examples, 1-ethyl-3-(3-dimethylaminopropyl)carbodiimide hydrochloride (EDC) is used for chemical conjugation (see, e.g., Ido et al., JBC, 287(31): 26377-26387, 2012, incorporated herein by reference). In some non-limiting examples, at least about 1-2, 2-5, 5-10, 10-15, 15-20, 20-25, or 25-30 mM or at least about 2, 5, 6, 10, 15, 20, or 25 mM EDC can be used. In further non-limiting embodiments, N-hydroxysulfosuccinimide (Sulfo-NHS) can be used in addition to the ECD (see, e.g., Ido et al., JBC, 287(31): 26377-26387, 2012, incorporated herein by reference). In some examples, at least about 5-10, 10-20, 20-30, 30-40-, 40-50, 50-75, 75-100, or 100-200 mM or at least about 5, 10, 25, 50, or 100 mM Sulfo-NHS can be used in addition to the ECD.

In other embodiments, alternative chemical conjugation (i.e., cross-linking) reagents may be used to form covalent bonds between amino groups and thiol groups and to introduce thiol groups into proteins (see, e.g., U.S. Pat. Pub. No. 2003/0040496, incorporated herein by reference). Additional alternative chemical conjugation (i.e., cross-linking) reagents can be found in the PIERCE CATALOG, ImmunoTechnology Catalog & Handbook, 1992-1993, which describes the preparation of and use of such reagents and provides a commercial source for such reagents (incorporated herein by reference; see also, e.g., Cumber et al., Bioconjugate Chem. 3:397-401, 1992; Thorpe et al., Cancer Res. 47:5924-5931, 1987; Gordon et al., Proc. Natl. Acad Sci. 84:308-312, 1987; Walden et al., J. Mol. Cell Immunol. 2:191-197, 1986; Carlsson et al., Biochem. J. 173:723-737, 1978; Mahan et al., Anal. Biochem., 162:163-170, 1987; Wawryznaczak et al., Br. J. Cancer 66:361-366, 1992; Fattom et al., Infection & Immun. 60:584-589, 1992, all of which are incorporated herein by reference). These reagents include, but are not limited to N-succinimidyl-3-(2-pyridyldithio)propionate (SPDP; disulfide linker); sulfosuccinimidyl 6-[3-(2-pyridyldithio)propionamido]hexanoate (sulfo-LC-SPDP); succinimidyloxycarbonyl-α-methyl benzyl thiosulfate (SMBT, hindered disulfate linker); succinimidyl 6-[3-(2-pyridyldithio) propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3'-dithiopropionate (SAED); sulfosuccinimidyl 7-azido-4-methylcoumarin-3-acetate (SAMCA); sulfosuccinimidyl 6-[alpha-methyl-alpha-(2-pyridyldithio)toluamido]hexanoate (sulfo-LC-SMPT); 1,4-di-[3'-(2'-pyridyldithio)propionamido]butane (DPDPB); 4-succinimidyloxycarbonyl-methyl-(2-pyridylthio)toluene (SMPT, hindered disulfate linker); sulfosuccinimidyl6[-methyl-2-pyridyldithio)toluamido]hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinmidyl(4-iodoacetyl)aminobenzoate (SIAB; thioether linker); sulfosuccinimidyl(4-iodoacetyl) aminobenzoate (sulfo-SIAB); succinimidyl4(p-maleimidophenyl)butyrate (SMPB); sulfosuccinimidyl4-(p-maleimidophenyl)butyate (sulfo-SMPB); and azidobenzoyl hydrazide (ABH).

III. Pharmaceutical Compositions and Methods of Treatment

Compositions and methods are disclosed herein for treating a subject, such as a mammalian subject (e.g., a human or veterinarian subject), with an inflammatory or immune disorder (such as an autoimmune disease) in a tissue. In some examples, the methods can ameliorate a sign or symptom of the inflammatory or immune disorder in a subject. Administering the fusion protein is sufficient to treat, inhibit, and/or prevent the inflammatory or immune disorder.

The methods include administering a therapeutically effective amount of a fusion protein that includes an anchor domain and a therapeutic polypeptide. In some examples, the anchor domain can be a carbohydrate-binding anchor domain from a lectin. A carbohydrate-binding anchor domain from any lectin that specifically binds an surface of a tissue (such as a surface containing cartilage or a surface of the bladder or mouth) can be used (see, e.g., Uusitalo et al., Histochemical Journal, 26: 787-798, 1994, which is incorporated herein by reference in its entirety). Non-limiting examples of lectins can include wheat germ agglutinin (WGA), jacalin (jac), and concanavalin A (conA). In other examples, the anchor domain is a collagen-binding anchor domain from von Willebrand factor (vWF) or *Clostridium* collagenase (ColH). In other examples, the anchor domain can be a heparin-binding anchor domain.

In some examples, the therapeutic polypeptide can be at least one of (1) an anti-inflammatory cytokine, such as interleukin (IL)-10, IL-1Ra, IL-6, IL-9, IL-21, IL-22, granulocyte-colony stimulating factor (G-CSF), transforming growth factor beta (TGFβ), IL-4, IL-5, IL-13, or vascular endothelial growth factor A (VEGF-A), or (2) an antagonist of or antibody against a pro-inflammatory cytokine, such as IL-9, IL-6, IL-1β, IL-1α, tumor necrosis factor alpha (TNFα), IL-18, interferon (IFN)γ, IL-12, granulocyte-macrophage colony-stimulating factor (GM-CSF), transforming growth factor beta (TGFβ), IL-21, IL-22, IL-23, IL-4, IL-5, IL-13, IL-17F, IL-17A, or VEGF-A. In exemplary embodiments, the therapeutic polypeptide includes IL-10, IL-1Ra, IL-6, IL-9, IL-21, IL-22, G-CSF, TGFβ, P17, P144, a TNF receptor 1 polypeptide (such as TBP1), IL-4, IL-5, IL-13, or VEGF-A. In some exemplary embodiments, the therapeutic polypeptide includes an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17A, IL-17F or VEGF-A. In some exemplary embodiments, the therapeutic polypeptide includes an immunoglobulin (Ig)-binding polypeptide or a fragment thereof, and the method can further include administering an antibody that specifically binds an Ig-binding polypeptide or fragment thereof. In specific examples, the antagonist is not an antibody, or is a non-antibody antagonist.

In further embodiments, where an Ig-binding polypeptide is administered as a therapeutic polypeptide, an additional therapeutically effective amount of an antibody is administered. In some examples, the antibody can be an antibody that specifically binds TGFβ1, TNFα, IL-10, IL-6, IFNγ, IL-9, IL-6, IL-1α, GM-CSF, IL-21, IL-22, IL-23, IL-4, IL-5, IL-13, IL-17F, IL-17A, or VEGF-A.

In some embodiments, the methods include administering a fusion protein that includes a collagen-binding anchor domain from von Willebrand factor (vWF) and a TGFβ1 antagonist or an Ig-binding polypeptide. In certain examples, the TGFβ1 antagonist can be P17 or p177. In other examples, the Ig-binding polypeptide can be protein A, protein G, or protein L or an fragment thereof, and the method can further include administering an antibody that specifically binds a protein A, protein G, or protein L or a fragment thereof.

In other embodiments, the methods include administering a fusion protein that includes a carbohydrate-binding anchor domain from WGA as an anchor domain and a TGFβ1 antagonist, a TNFα antagonist, an IL-1β antagonist, an IL-6 antagonist, an interferon (IFN)γ antagonist, or IL-10 as a therapeutic polypeptide. In some non-limiting examples, the antibody can be an antibody that specifically binds TGFβ1, TNFα, IL-10, IL-6, IFNγ, IL-9, IL-6, IL-1α, GM-CSF, IL-21, IL-22, IL-23, IL-4, IL-5, IL-13, IL-17F, IL-17A, or VEGF-A.

In further embodiments, the methods include administering a fusion protein that includes a heparin-binding anchor domain as an anchor domain and a TNFα antagonist. In some non-limiting examples, the TNFα antagonist can be an inhibitor of TNFα polypeptide from the TNF receptor 1.

In additional embodiments, a subject is selected that has or is at risk for at least one inflammatory or immune disorder that affects a tissue. The subject can have a disorder in any tissue, and the disorder can be a chronic or an acute disorder. Methods for selecting subjects with an inflammatory or immune disorder are known in the medical arts and can be used to select the subjects described herein. In some non-limiting examples, the tissue is a tissue in the mouth, bladder, nasal cavity, gastrointestinal tract, a lung, joint (or other cartilage-containing tissue), reproductive system, or eye.

In some examples, the methods include treating or inhibiting an inflammatory or immune disorder. The inflammatory or immune disorder can be any type of inflammatory or immune disorder, such as a cytokine storm, or can be an inflammatory or immune disorder associated with another condition and/or disease (e.g., infection). In specific embodiments, the subject has chronic obstructive pulmonary disease, asthma, bronchitis, rhinosinusitis, mucositis, left-sided ulcerative colitis, inflammatory bowel disease, periodontal disease, peri-implantitis, interstitial cystitis, atrophic vaginitis, or arthritis, or Sjögren's syndrome.

In some embodiments, the inflammatory or immune disorder is an inflammatory disorder. Examples of inflammatory disorders include rheumatoid arthritis, osteoarthritis, osteolytis, tendonitis, synovitis, peripheral vascular disease, and inflammatory respiratory diseases (such as chronic obstructive pulmonary disease, fibrosis, emphysema, acute respiratory distress syndrome, and pneumonia). The methods herein can also be used to treat pain associated with inflammation, such as pain associated with traumatic injury, muscle strain, arthritis (rheumatoid arthritis and osteoarthritis), synovitis, sacroiliac joint disorders, back disorders, post-surgical injections, tendon injections, sports medicine procedure (for example, ACL repair, MCL repair, BTB repair, patella repair, or cartilage repair), contusions, muscle strains, post traumatic osteoarthritis. In some examples, the inflammation is chronic, and the inflammatory disorder can include hay fever, periodontitis, atherosclerosis, rheumatoid arthritis, or cancer. Other examples of inflammatory disorders that can be treated using the methods herein include those disclosed in U.S. Pat. Pub. Nos. 20140274895 and 20140274913, both of which are incorporated herein by reference in their entireties.

In some embodiments, the inflammatory or immune disorder is an immune disorder, such as autoimmune disease. Exemplary immune disorders, such as autoimmune diseases, include allograft rejection, systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome.

In some examples, the subject (e.g., a subject with an inflammatory or immune disorder, such as an autoimmune disease, transplant rejection, inflammation, or an inflammatory disease) is also administered one or more immunomodulatory therapies (e.g., immunomodulatory biologics, such as muromonab, ipilimumab, abatacept, belatacept, tremelimumab, BMS-936558, CT-011, MK-3475, AMP224, BMS-936559, MPDL3280A, MEDI4736, MGA271, IMP321, BMS-663513, PF-05082566, CDX-1127, anti-OX40, huMAb, OX40L, and TRX518, e.g., Yao et al., Nat Rev Drug Discov, 12(2): 130-146, 2013, and Kamphorst et al., Vaccine, 33(0 2): B21-B28, 2015, both of which are incorporated herein by reference in their entireties; modulatory cytokines, such as IL-7; mTOR modulatory agents, such as rapamycin; antimicrobial therapy, such as vaccination, antifungals, and/or antibiotics), anti-inflammatory agents (NSAIDS; antileukotrines; immune selective anti-inflammatory derivatives, ImSAIDs; bioactive compounds with anti-inflammatory activities, such as plumbagin and plumericin; and/or steroids), disease-modifying antirheumatic drugs (DMARDs, such as methotrexate, sulfasalazine, leflunomide, hydroxychloroquine, tofacitinib, infliximab, etanercept, adalimumab, certolizumab, golimumab, tocilizumab, anakinra, abatacept, and/or rituximab), antimalarial drugs (e.g., chloroquine and hydroxychloroquine), medical procedures (including surgery and stem cell transplantation); immunosuppressive agents (e.g., for preventing rejection of transplanted organs or tissues, treating autoimmune diseases, and/or inflammatory diseases; e.g., glucocorticoids, such as prednisone, dexamethasone, and hydrocortisone; cytostatics, such as alkylating agents and antimetabolites; antibodies, such as Atgam, thymoglobuline, and T-cell receptor- and IL-2 receptor-directed antibodies; immunophilin-targeting agents, such as cyclosporin, tacrolimus, sirolimus, and everolimus; interferons (IFNs), such as IFNλ and IFNβ; opioids; TNF binding proteins, such as infliximab, etanercept, and adalimumab; mycophenolate; and small biological agents, such as fingolimod and myriocin), immune tolerance therapy (e.g., for treating subjects at risk for tissue or organ transplantation rejection, subjects with allergies, and/or subjects with autoimmune disease; e.g., T or B cell-targeting or T or B cell-suppressing drugs, such as CAMPATH-1H, calcineurin inhibitors, rituximab, epratuzumab, belimumab, and atacicept; anti-cluster of differentiation (CD)3 antibodies; abatacept; induction of hematopoietic chimerism, such as mixed hematopoietic chimerism, in which the bone marrow of an organ or a tissue recipient is replaced with the donor's bone marrow or a mixture of the donor and recipient bone marrow to reduce organ or tissue transplant rejection; antigen desensitization; see Nepom et al., Immunol Rev; 241(1): 49-62, 2011, incorporated herein by reference), antihistamines, helminthic therapies (e.g., deliberate infestation of the subject with a helminth or with the ova of a helminth for treating immune disorders).

In specific embodiments, the tissue with an inflammatory or immune disorder includes a joint (or other cartilage-containing tissue). In some embodiments, the methods include selecting a subject with rheumatoid arthritis (a systemic disorder in which immune cells attack and inflame the membrane around joints, heart, lungs, and eyes), scleroderma (an autoimmune condition that causes scar tissue to form in the skin, internal organs (including the gastrointestinal tract), and small blood vessels), granulomatosis (such as with polyangiitis or Wegener's granulomatosis, which is a form of vasculitis, or inflammation of the blood vessels, that affects the nose, lungs, kidneys, and other organs), Churg-Strauss syndrome (an autoimmune vasculitis that affects cells in the blood vessels of the lungs, gastrointestinal system, skin, and nerves), systemic lupus erythematosus lupus (SLE; a disease that causes inflammation of the connective tissue in every organ of the body, including the brain, skin, blood, to the lungs), microscopic polyangiitis (an autoimmune disease that affects cells in blood vessels in organs throughout the body), polymyositis/dermatomyositis (inflammation and degeneration of the muscles), or other inflammatory or immune disorder that affects the joints (or other cartilage-containing tissue). In some examples, the methods include administering to the joint (such as directly administering) a therapeutically effective amount of a fusion protein that includes an anchor domain and a therapeutic polypeptide, thereby treating the inflammatory or immune disorder. In some examples, the methods include administering a therapeutically effective amount of a fusion protein that includes an anchor domain and a therapeutic polypeptide, thereby treating the inflammatory or immune disorder. For example, the anchor domain can include a lectin carbohydrate binding domain, such as WGA; vWF; ColH; or HS, and the therapeutic polypeptide can include IL-10, IL-1Ra, IL-6, IL-9, IL-21, IL-22, G-CSF, TGFβ, P17, P144, a TNF receptor 1 polypeptide (such as TBP1), IL-4, IL-5, IL-13, VEGF-A, or an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A. In specific, non-limiting examples, the anchor domain includes WGA, and the therapeutic polypeptide includes an antibody that specifically binds a pro-inflammatory cytokine (such as IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A).

In specific embodiments, the tissue with an inflammatory or immune disorder includes the mouth. In some embodiments, the methods include selecting a subject with pemphigus, bullous pemphigoid, cicatrical pemphigoid, epidermolysis bullosa, SLE, myasthenia gravis, dermatomyositis, systemic sclerosis, idiopathic thrombocytopenic purpura (ITP), Sjogren's syndrome, benign lymphoepithelial lesion (or Mikulicz's diease), aphthous stomatitis, periodontal disease, or giant cell arteritis. In some examples, the methods include administering to the tissue in the mouth (such as directly administering) a therapeutically effective amount of a fusion protein that includes an anchor domain and a therapeutic polypeptide, thereby treating the inflammatory or immune disorder. For example, the anchor domain can include a lectin carbohydrate binding domain, such as WGA; vWF; ColH; or HS, and the therapeutic polypeptide can include IL-10, IL-1Ra, IL-6, IL-9, IL-21, IL-22, G-CSF, TGFβ, P17, P144, a TNF receptor 1 polypeptide (such as TBP1), IL-4, IL-5, IL-13, VEGF-A, or an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A. In specific, non-limiting examples, the anchor domain includes WGA, and the therapeutic polypeptide includes an antibody that specifically binds a pro-inflammatory cytokine (such as IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A).

In specific embodiments, the tissue with an inflammatory or immune disorder includes the bladder. In some embodiments, the methods include selecting a subject with interstitial cystitis. In some examples, the methods include administering to the bladder (such as directly administering) a therapeutically effective amount of a fusion protein that includes an anchor domain and a therapeutic polypeptide, thereby treating the inflammatory or immune disorder. For example, the anchor domain can include a lectin carbohydrate binding domain, such as WGA; vWF; ColH; or HS, and the therapeutic polypeptide can include IL-10, IL-1Ra, IL-6, IL-9, IL-21, IL-22, G-CSF, TGFβ, P17, P144, a TNF receptor 1 polypeptide (such as TBP1), IL-4, IL-5, IL-13, VEGF-A, or an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A. In specific, non-limiting examples, the anchor domain includes WGA, and the therapeutic polypeptide includes an antibody that specifically binds a pro-inflammatory cytokine (such as IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A).

In specific embodiments, the tissue with an inflammatory or immune disorder includes the eye. In some embodiments, the methods include selecting a subject with dry eye disease (DED; see, e.g., U.S. Patent Pub. No. 2006/0281739, incorporated herein by reference). In some non-limiting examples, the DED can be caused by keratoconjunctivitis sicca, Sjorgen's syndrome, corneal injury, age-related dry eye, Stevens-Johnson syndrome, congenital alachrima, pharmacological side effects, infection, Riley-Day syndrome, conjunctival fibrosis, eye stress, glandular and tissue destruction, ocular cicatrical pemphogoid, blepharitis, autoimmune and other immunodeficient disorders, allergies, diabetes, lacrimal gland deficiency, lupus, Parkinson's disease, Sjogren's syndrome, rheumatoid arthritis, rosacea, environmental exposure to excessively dry air, airborne particulates, smoke, smog, and/or an inability to blink. In some examples, the methods include administering a therapeutically effective amount of a fusion protein that includes an anchor domain and a therapeutic polypeptide, thereby treating the inflammatory or immune disorder. For example, the anchor domain can include a lectin carbohydrate binding domain, such as WGA; vWF; ColH; or HS, and the therapeutic polypeptide can include IL-10, IL-1Ra, IL-6, IL-9, IL-21, IL-22, G-CSF, TGFβ, P17, P144, a TNF receptor 1 polypeptide (such as TBP1), IL-4, IL-5, IL-13, VEGF-A, or an antagonist of or antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A. In specific, non-limiting examples, the anchor domain includes WGA, and the therapeutic polypeptide includes an antibody that specifically binds IL-17A or IL-23 (such as provided in U.S. Pat. No. 7,838,638, the TC11-18H10.1 anti-IL-17A antibody (Biolegend), or U.S. Pat. No. 7,491,391).

In some embodiments, the fusion protein is administered locally. Local modes of administration include topical application, such as ointments and topical solutions, or any other pharmaceutical dosage form formulated for administration to the tissue of interest. Administration can include an extended release formulation, such as by dissociation of the fusion protein or, if collagen is bound, though digestion of collagen by collagenases. In an embodiment, significantly smaller amounts of the therapeutic polypeptide (compared with systemic approaches) may exert an effect when administered locally compared to when the therapeutic polypeptide is administered systemically (for example, intravenously).

A suitable topical formulation of a fusion protein containing a carbohydrate-binding anchor domain from a lectin, collagen-binding anchor domain from von Willebrand factor (vWF) or *Clostridium* collagenase (ColH), or a heparin-binding anchor domain and a therapeutic polypeptide that includes IL-10, IL-1Ra, IL-6, IL-9, IL-21, IL-22, G-CSF, TGFβ, P17, P144, a TNF receptor 1 polypeptide (such as TBP1), IL-4, IL-5, IL-13, or VEGF-A; an antagonist of or an antibody that specifically binds IL-9, IL-6, IL-1β, IL-1α, TNFα, IL-18, interferon IFNγ, IL-12, GM-CSF, TGFβ, IL-21, IL-22, IL-23, IL-4, IL-5, IL-13, IL-17F, IL-17A, or VEGF-A; an immunoglobulin-binding (Ig) polypeptide and/or an antibody that specifically binds IFNγ, protein A, protein G, and/or protein L; or an effective fragment or variant thereof and is, for example, drops containing, for example, about 0.1, 1, 10, 100, 1,000, or 10,000 μM of the fusion protein. In some embodiments, the fusion protein can be administered at a dose in the range of about 0.1, 1, 10, 100, 1,000, or 10,000 M or about 0.01, 0.1, 1, 10, 100, or 1000 μg/ml per day, either as a single dose or as divided doses. In a specific non-limiting example, the dose is administered about 1, 2, or 3 times daily. In some embodiments, the fusion protein is administered for at least 1, 2, 3, 4, 5, 6, 7, 8, 9, 10, 11, 12, 13, or 14 days or 3 or 4 weeks.

A pharmaceutical composition can be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the principal active ingredients, the vehicles and compositions can include various formulatory ingredients, such as anti-microbial preservatives and tonicity agents. For example, antimicrobial preservatives include: benzalkonium chloride, thimerosal, chlorobutanol, methylparaben, propylparaben, phenylethyl alcohol, EDTA, sorbic acid, POLYQUAD® and other agents equally well known to those skilled in the art. Such preservatives, if employed, will typically be used in an amount from about 0.0001 wt. % to 1.0 wt. %. Suitable agents that may be used to adjust tonicity or osmolality of the compositions include: mannitol, dextrose, glycerine, and propylene glycol. If used, such agents will be employed in an amount of about 0.1 wt. % to 10.0 wt. %. However, the composition does not include preservatives or tonicity agents that are known to adversely affect or irritate tissue.

In addition to the active ingredient, a pharmaceutical composition can further comprise one or more additional pharmaceutically active agents. Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.01% to about 10% (w/w) active ingredient; although, the concentration of the active ingredient may be as high as the solubility limit of the active ingredient in the solvent. Formulations for topical administration may further comprise one or more of the additional ingredients described herein.

The pharmaceutical compositions may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, water, 1,3-butane diol, Ringer's solution, isotonic sodium chloride solution, and fixed oils such as synthetic mono- or di-glycerides, glycerin, vegetable oils such as cottonseed oil, olive oil, grapeseed oil, tea tree oil, almond oil, avocado oil, sesame oil, evening primrose oil, sunflower oil, kukui nut oil, jojoba oil, walnut oil, peanut oil, pecan oil, macadamia nut oil, coconut oil, and the like and combinations thereof, organic esters such as ethyl oleate, and water-oil emulsions. Other parenterally administrable formulations that are useful include those that comprise the active ingredient in microcrystalline form, in a liposomal preparation, or as a component of a biodegradable polymer systems. Compositions for sustained release or implantation may comprise pharmaceutically acceptable polymeric or hydrophobic materials, such as an emulsion, an ion exchange resin, a sparingly soluble polymer, or a sparingly soluble salt.

A pharmaceutical composition of the invention may be prepared, packaged, or sold in a formulation suitable for ophthalmic administration. Such formulations may, for example, be in the form of drops including, for example, a 0.01% to 10% (w/w) solution or suspension of the active ingredient in an aqueous or oily liquid carrier.

In some embodiments, the compositions can be formulated into gels, creams, lotions, or ointments. Gels are semi-solid dispersion of liquid or oil particles in a semi-solid medium and may include, for example, petroleum jelly and coco butter. In these mixtures, the fusion proteins may be in the form of a suspension or form a gel with the excipient and can be mixed with solids such as starches and methyl cellulose. Creams refer to semi-solid emulsions of oil and water in approximately equal proportions. They are divided into two types: oil-in-water (O/W) creams, composed of small droplets of oil dispersed in a continuous phase, and water-in-oil (W/O) creams, composed of small droplets of water dispersed in a continuous oily phase. Creams can provide a barrier to protect the skin. Lotions are low- to medium-viscosity topical preparation. Most lotions are oil-in-water emulsions containing an emulsifier, such as cetyl alcohol to prevent separation of these two phases, and include, for example, fragrances, glycerol, petroleum jelly, dyes, preservatives, proteins, and stabilizing agents. Ointments are compositions in which oil and water are provided in a ratio of from 7:1 to 2:1, from 5:1 to 3:1, or 4:1. Ointments are generally formulated using oils, waxes, water, alcohols, petroleum products, water, and other agents to prepare formulations with various viscosities and solvent properties. Commonly used ointment formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

Pharmaceutical compositions for sustained release or implantation may include pharmaceutically acceptable polymeric or hydrophobic materials such as an emulsion, an ion exchange resin, a sparingly soluble polymer, or a sparingly soluble salt. Such drops may further comprise buffering agents, salts, or one or more other of the additional ingredients described herein. Other administrable formulations that are useful include those that comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example, in Genaro, ed., *Remington's Pharmaceutical Sciences*, Mack Publishing Co., Easton, Pa., 1985, and U.S. Pat. No. 6,534,059, which is incorporated herein by reference. In some embodiments, additional pharmaceutically active drugs can be included in the vehicles of to make ophthalmic compositions. Drugs which can be delivered in vehicles include, but are not limited to, steroids, growth factors, antioxidants, aldose reductase inhibitors, non-steroidal anti-inflammatories, immunomodulators, anti-allergics, antimicrobials, and beta-blockers.

Exemplary salts include pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, hydroxybutyric, galactaric, and galacturonic acid.

In some embodiments, pharmaceutical compositions may further include hydrocortisone or any steroid within Groups I to VII in the US classification system. Group I steroids include, but are not limited to, clobetasol propionate, betamethasone dipropionate, halobetasol, and diflorasone diacetate. Group II steroids include, but are not limited to, fluocinonide, halcinonide, amcinonide, and desoximetasone. Group III steroids include, but are not limited to, triamcinolone acetonide, mometasone furoate, fluticasone propionate, betamethasone dipropionate, and halometasone. Group IV steroids include, but are not limited to, fluocinolone acetonide, hydrocortisone valerate, hydrocortisone butyrate, flurandrenolide, triamcinolone acetonide, and mometasone furoate. Group V steroids include, but are not limited to, fluticasone propionate, desonide, fluocinolone acetonide, and hydrocortisone valerate. Group VI steroids include, but are not limited to, alclometasone dipropionate, triamcinolone acetonide, fluocinolone acetonide, and desonide. Group VII steroids include, but are not limited to, hydrocortisone (2.5%) and hydrocortisone (1%). The amount of hydrocortisone or steroid within Groups I to VII in the pharmaceutical composition is not particularly limited, so long as it is a therapeutically effective amount. An amount may be from about 0.01% to about 5%, relative to the total amount of the pharmaceutical composition, or about 0.1% to about 1%, relative to the total amount of the pharmaceutical composition.

In some embodiments, pharmaceutical composition may further include an antibiotic compound. The antibiotic compound is not particularly limited and may be at least one member selected from the group consisting of ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam. The amount of the antibiotic compound in the topical formulation is not particularly limited, so long as it is a therapeutically effective amount. An amount is from about 0.01% to about 5%, relative to the total amount of the pharmaceutical composition, more preferably from about 0.1% to about 1%, relative to the total amount of the pharmaceutical composition.

In some embodiments, pharmaceutical compositions may further include an antiseptic compound. The antiseptic compound is not particularly limited, and may be at least one member selected from the group consisting of iodine, manuka honey, octenidine dihydrochloride, phenol, polyhexanide, sodium chloride, sodium hypochlorite, calcium hypochlorite, sodium bicarbonate, methyl paraben, and sodium dehydroacetate. The amount of the antiseptic compound in the pharmaceutical composition is not particularly limited, so long as it is a therapeutically effective amount. An amount may be from 0.01% to 5%, relative to the total amount of the pharmaceutical composition, more preferably from 0.1% to 1%, relative to the total amount of the pharmaceutical composition.

In some embodiments, pharmaceutical compositions may further include an antifungal agent. The antifungal agent is not particularly limited, and may be at least one member selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, and balsam of Peru. The amount of the antifungal agent in the pharmaceutical composition is not particularly limited, so long as it is a therapeutically effective amount. An amount may be from about 0.01% to about 5%, relative to the total amount of the pharmaceutical composition, more preferably from about 0.1% to about 1%, relative to the total amount of the pharmaceutical composition.

In some embodiments, pharmaceutical compositions may include a humectant, which can be referred to as a soothing, smoothing, moisturizing, or protective agent. The humectant is not particularly limited and may be at least one member selected from the group consisting of calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. Sodium lauryl sulphate and calamine are the most preferred humectants. The amount of the humectant in the topical formulation is not particularly limited, so long as it is a therapeutically effective amount. An amount may be from about 0.01% to about 5%, relative to the total amount of the pharmaceutical composition, more preferably about 0.1% to about 1%, relative to the total amount of the pharmaceutical composition.

In some embodiments, pharmaceutical compositions may contain a UV-absorbing compound, which can be referred to as a sunscreen agent. The UV-absorbing compound is not particularly limited and may be at least one member selected from the group consisting of glyceryl PABA, padimate, roxadimate, dioxybenzone, oxybenzone, sulisonbenzone, octocrylene, octyl methoxycinnamate, ethoxyethyl p-methoxycinnamate, homomenthyl salicylate, ethylhexyl salicylate, trolamine salicylate, avobenzone, ecamsule, ensulizole, bemotrizinol, and bisoctrizole. The amount of the UV-absorbing compound in the pharmaceutical composition is not particularly limited, so long as it is a therapeutically effective amount. An amount may be from about 0.01% to about 5%, relative to the total amount of the pharmaceutical composition or about 0.1% to about 1%, relative to the total amount of the pharmaceutical composition.

In some embodiments, pharmaceutical composition may include an analgesic agent. The analgesic agent is not particularly limited and is preferably at least one member selected from the group consisting of methyl salicylate, codeine, morphine, methadone, pethidine, buprenorphine, hydromorphine, levorphanol, oxycodone, fentanyl, and a non-steroidal anti-inflammatory drug (NSAID). The amount of the analgesic agent in the topical formulation is not particularly limited, so long as it is a therapeutically effective amount. An amount may be from about 0.01% to about 5%, relative to the total amount of the pharmaceutical composition, or about 0.1% to about 1%, relative to the total amount of the pharmaceutical composition.

Dosage treatment may be a single dose schedule or a multiple dose schedule to ultimately deliver the amount specified above. The doses can be intermittent. Moreover, the subject may be administered as many doses as appropriate. In some embodiments, the subject is administered a fusion protein prior to the onset of a condition. Administration may be provided as a single administration or a periodic bolus. Thus, the disclosed compositions can be administered hourly, 1, 2, 3, or 4 times daily, daily, every other day, or weekly. The disclosed compositions can be administered when the subject experiences a "flare-up" of the disease condition.

Individual doses are typically not less than an amount required to produce a measurable effect on the subject and may be determined based on the pharmacokinetics and pharmacology for absorption, distribution, metabolism, and excretion ("ADME") of the subject composition or its by-products and, thus, based on the disposition of the composition within the subject. This includes consideration of the route of administration as well as dosage amount, which can be adjusted for local applications. Effective amounts of dose and/or dose regimen can readily be determined empirically from preclinical assays, from safety and escalation and dose range trials, individual clinician-patient relationships, as well as in vitro and in vivo assays. Generally, these assays will evaluate inflammation, the rate of tear formation, the integrity of the corneal epithelium by staining with dyes, or expression of a biological component (cytokine, specific inflammatory cell, microglia, etc.) that affects inflammation or the rate of tear formation.

In some embodiments, the method results in a therapeutic benefit, such as preventing the development of, halting the progression of, and/or reversing the progression of a disorder and/or inflammation.

In some embodiments, the method includes the step of detecting that a therapeutic benefit has been achieved. Measures of therapeutic efficacy will be applicable to the particular disease being modified and will recognize the appropriate detection methods to use to measure therapeutic efficacy.

Effective treatment can be measured by many methods known to those of skill in the art. For example, neutrophil infiltration at a site of inflammation can be measured. In order to assess neutrophil infiltration myeloperoxidase activity can be measured. Myeloperoxidase is a hemoprotein present in azurophilic granules of polymorphonuclear leukocytes and monocytes. It catalyzes the oxidation of halide ions to their respective hypohalous acids, which are used for microbial killing by phagocytic cells. Thus, a decrease in myeloperoxidase activity in a tissue reflects decreased neutrophil infiltration and can serve as a measure of inhibition of inflammation.

In another example, effective treatment can be assayed by measuring cytokine levels in the subject. Cytokine levels in body fluids or cell samples are determined by conventional methods. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well-known in the art and are described, for example, in Czerkinsky et al., *J. Immunol. Methods* 110:29-36, 1988; Olsson et al. *J. Clin. Invest.* 86:981-985, 1990; and EP 957359. Variations of the standard immunospot assay are well-known in the art and can be used to detect alterations in cytokine production in the methods of the disclosure (see, for example, U.S. Pat. Nos. 5,939,281 and 6,218,132).

Antibodies suitable for use in immunospot assays, which are specific for secreted cytokines, as well as detection reagents and automated detection systems, are well-known in the art and generally are commercially available. Appropriate detection reagents are also well-known in the art and commercially available, and include, for example, secondary antibodies conjugated to fluorochromes, colored beads, and enzymes the substrates of which can be converted to colored products (for example, horseradish peroxidase and alkaline phosphatase). Other suitable detection reagents include secondary agents conjugated to ligands (for example, biotin) that can be detected with a tertiary reagent (for example, streptavidin) that is detectably labeled as above.

Other methods for measuring cytokine levels in the subject are well known in the art and can be used as an alternative to immunospot assays. Such methods include ELISA, which can be used to measure the amount of cytokine secreted by T-cells into a supernatant (see, for example, Vandenbark et al., *Nature Med.* 2:1109-1115, 1996). Alternatively, the expression of cytokine mRNA can be determined by standard immunological methods, which include reverse transcriptase polymerase chain reaction (RT-PCR) and in-situ hybridization.

The disclosure is illustrated by the following non-limiting Examples.

VI. Examples

The following examples are provided to illustrate particular features of certain embodiments, but the scope of the claims should not be limited to those features exemplified.

Example 1

Binding of Anchor Domains Fused to a Heterologous Protein

Domains to four different collagen-binding domains were fused to a reporter protein (LacZ). The LacZ fusion proteins were applied to collagen III columns (Sigma-Aldrich®) to analyze the binding of these compounds and eluted with high salt concentrations. LacZ was detected by hydrolysis of ortho-Nitrophenyl-β-galactoside. FIG. 1 shows that all anchor domains with the LacZ bound to collagen. A control protein without an anchor domain did not bind. The binding of the four fusion proteins containing anchor domains demonstrates that the anchor domains are functional.

Example 2

Binding to Collagen I and IV

Figure 2:
FIG. 2 is a bar graph showing LacZ fusion proteins binding to collagen I and collagen IV.

The cornea contains two major forms of collagen: collagen I, which is present in large amounts in the stroma, and collagen IV, which is present in the basement membrane and is accessible after superficial damage to the cornea. As illustrated in FIG. 2, LacZ coupled to all four collagen-binding anchor domains binds both types of collagen with similar efficiencies. The indicated LacZ fusion proteins bound to CORNING™ BIOCOAT™ Collagen I or IV plates.

Example 3

Binding of Anchored LacZ Fusion Proteins to Rabbit Eyes Ex Vivo

Figure 3:
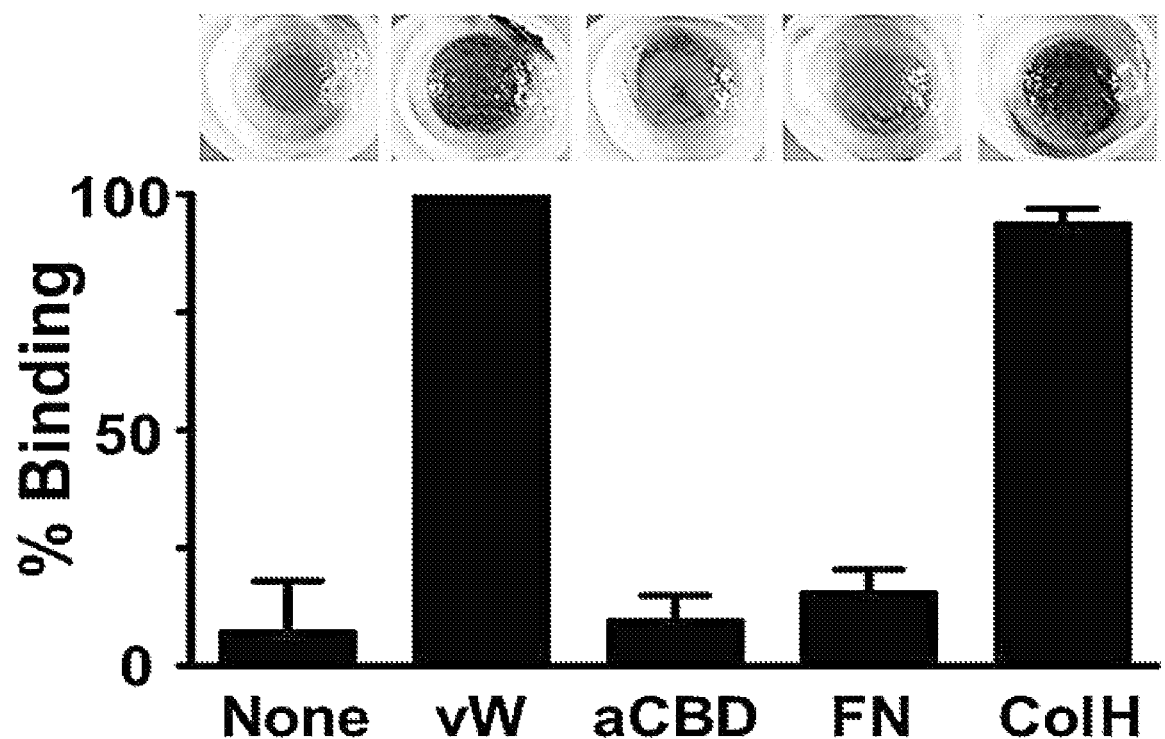
FIG. 3 shows rabbit eyes that were (PelFreez Biologicals) wounded by scraping with sandpaper. Equal amounts, determined by enzymatic activity, of the LacZ fusion proteins were applied to eyes for two minutes, washed, and the proteins detected with X-gal (top row). Staining intensities were determined with the ImageJ program and are illustrated in the bar graph.

To determine binding to corneas, LacZ fusion proteins were applied to wounded rabbit eyes ex vivo. Incubation was for two minutes to simulate the short residency time on the cornea when applied in eye drops. Binding varied widely, which can be due to masked binding sites in the tissues. A 10-amino acid sequence from the bovine von Willebrand Factor (vWF) and a 223-amino acid domain from *Clostridium histolyticum* collagenase H bind bound most efficiently (see FIG. 3). No protein bound to unwounded eyes. The vWF binding domain (WREPSFMALS) was used because it is a short sequence that is easily cloned and engineered (for instance, to create mutants with different binding affinities) and is unlikely to induce an immune response.

Example 4

Adapter Mediates Biding of Antibodies

Figure 4:
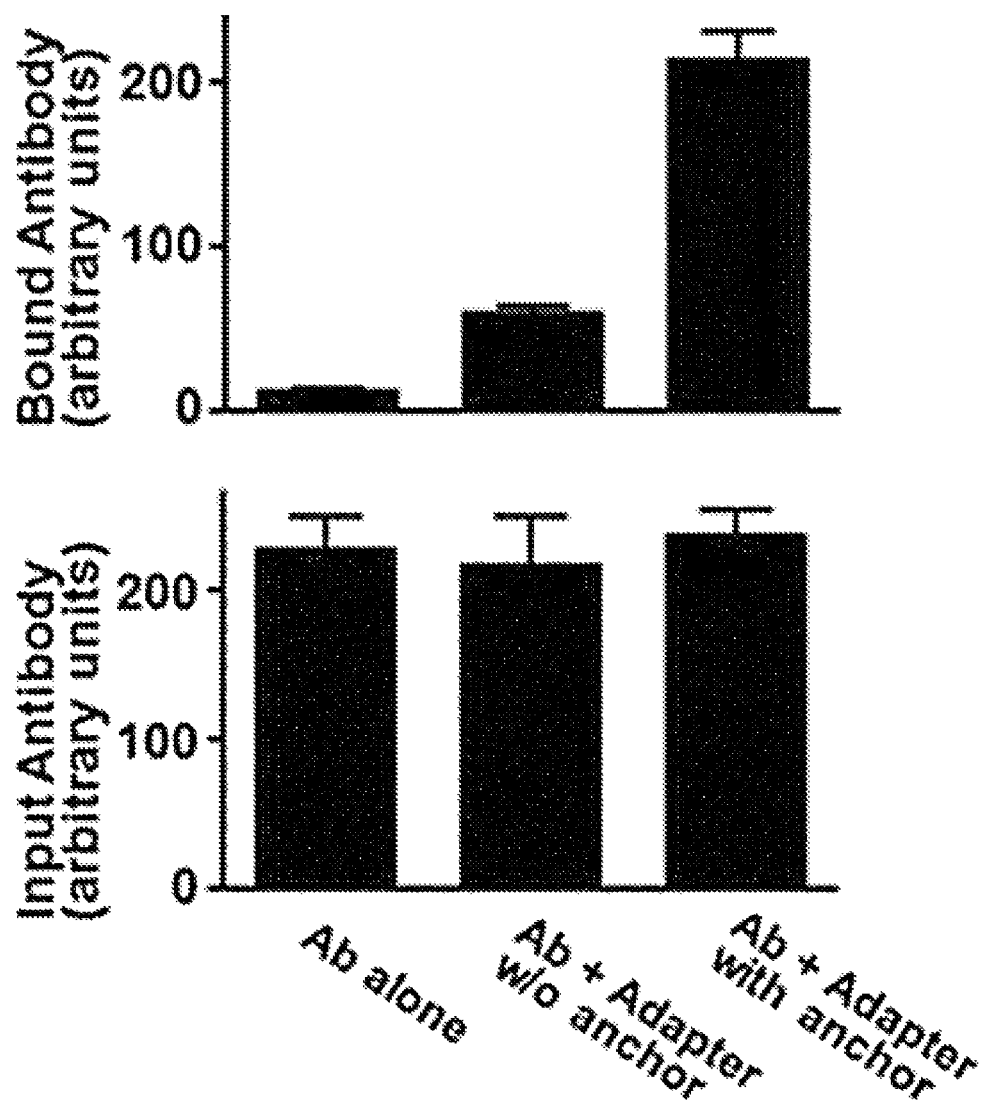
FIG. 4 are bar graphs showing alkaline phosphatase conjugated goat anti-human IgG (Invitrogen) was incubated with the adaptor (the immunoglobulin-binding domain of protein G coupled to the von Willebrand binding domain) and with or without the vWF anchor. Input antibody (bottom) and bound antibody (top) are shown.

Alkaline phosphatase-conjugated goat anti-human IgG (Invitrogen®) was incubated with a 10-fold molar excess of the adaptor with or without the vWF anchor as described below. Samples were diluted to 50 µl in hepes buffered saline (HBS) with 0.1% BSA and incubated in collagen I-coated BioCoat™ 96-well plates (Corning®) for two hours with constant agitation. After extensive washing, the bound antibody was detected using a standard colorimetric assay with para-nitrophenylphosphate (see, FIG. 4). The top shows bound antibody; the bottom shows the amount of input antibody. The "adapter" contains the vWF domain and the two C-terminal antibody-binding domains of protein G, which has a strong affinity to antibodies and has been used extensively as an affinity tag in the tandem affinity purification procedure. The adapter can be attached to any antibody with affinity to protein G, and the complex binds to collagen. Similar fusion proteins can be constructed with protein A and L; thus, almost any antibody can be attached to collagen with an adapter.

Example 5

Attaching Lectin Wheat Germ Agglutinin as an Anchor

Figure 5:
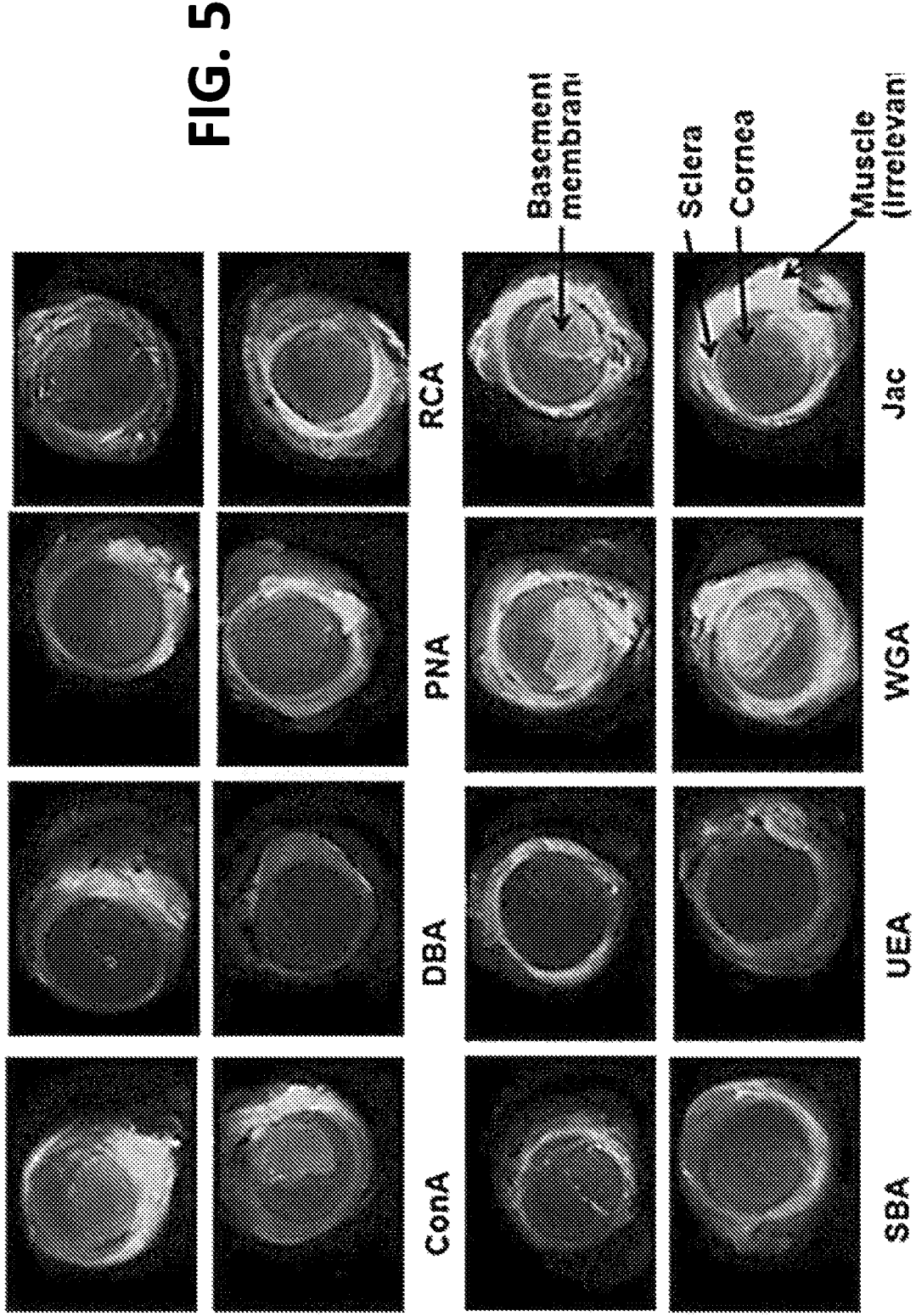
FIG. 5 shows images of fluorescein-labeled lectins (ConA, Concanavalin A; DBA, *Dolichos biflorus* agglutinin; PNA, peanut agglutinin; RCA, *Ricinus* communisagglutinin; SBA, soybean agglutinin; UEA, *Ulex europaeus* agglutinin; WGA, wheat germ agglutinin; Jac, jacalin) attached to rabbit eyes.

Rabbit eyes were exposed to *Pseudomonas aeruginosa*, which induced lesions in many of the eyes. The next day, equal amounts of fluorescein-labeled lectins (ConA, Concanavalin A; DBA, *Dolichos biflorus* agglutinin; PNA, peanut agglutinin; RCA, *Ricinus* communisagglutinin; SBA, soybean agglutinin; UEA, *Ulex europaeus* agglutinin; WGA, wheat germ agglutinin; Jac, jacalin, from Vector Labs) in 10 µl HBS with 0.1% BSA were applied to the surface of the eyes for two minutes, and the eyes were washed and photographed using a fluorescence stereo microscope. FIG. 5 shows the results from two experiments. Wheat germ agglutinin (WGA) bound strongly to the surfaces of the cornea and the sclera as well as to wounded regions.

Figure 6B:
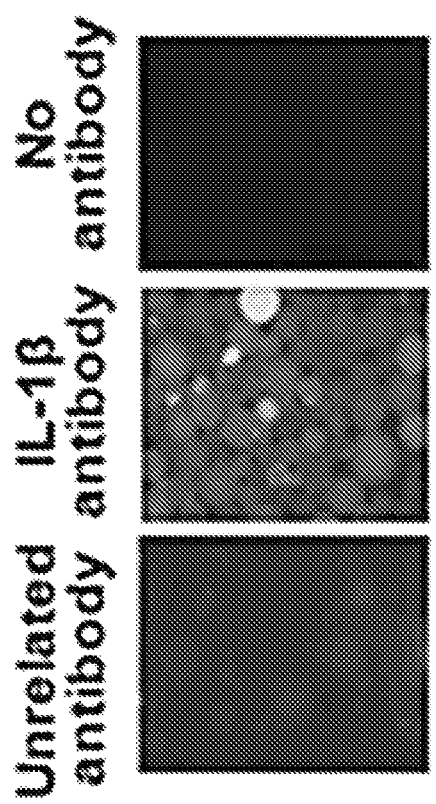
FIG. 6B shows images of unlabeled WGA conjugated antibodies that are specific for IL-1β were bound to acetyl-glucosamine (GlnAc) beads and incubated with Alexa Fluor 488-labeled IL-1β.
Figure 6C:
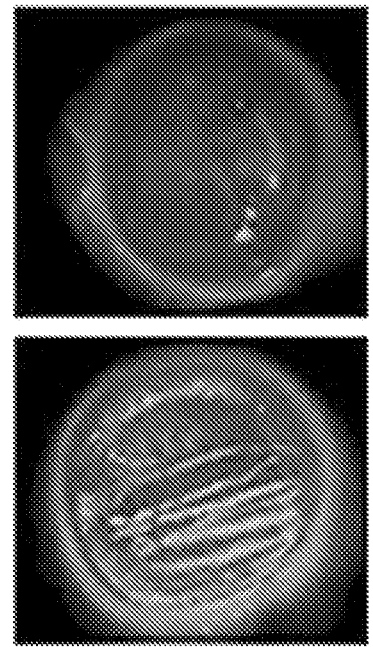
FIG. 6C shows images of fresh rabbit eyes that were scraped and incubated with WGA conjugated Alexa Fluor 488-labeled IL-1β antibodies.
Figure 6A:
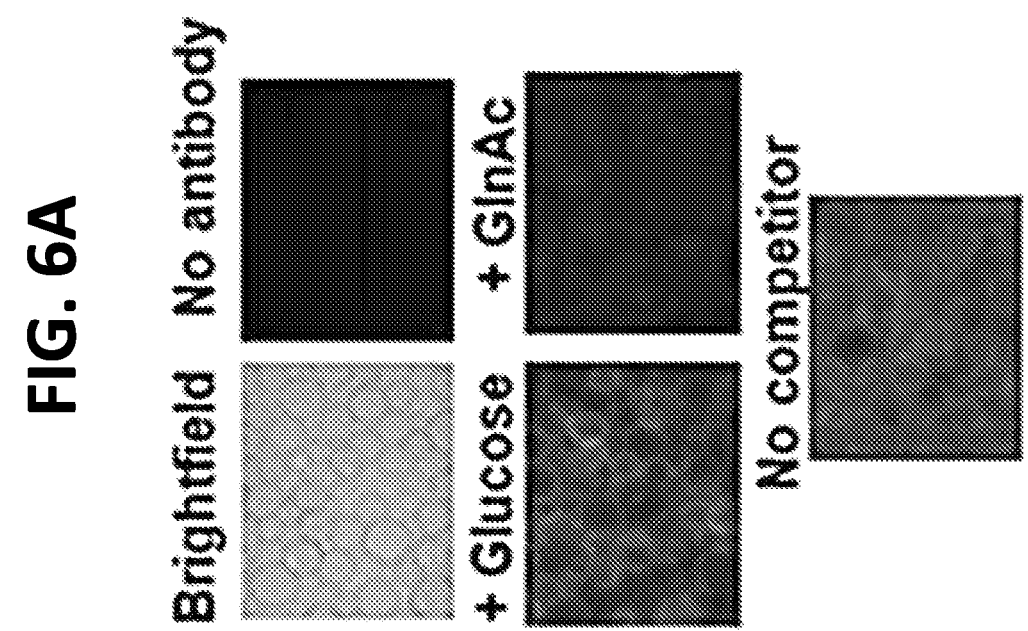
FIG. 6A shows images of anti-IL-1β antibody (Invitrogen) conjugated to WGA and labeled with Alexa Fluor 488 and incubated with GlnAc agarose beads.

MM425B anti IL-1β antibody (Invitrogen®) was conjugated to WGA and labeled with Alexa Fluor® 488 and incubated with GlnAc agarose beads with 0.2 M competitors as indicated. The beads were photographed with a fluorescence microscope as shown in FIG. 6A. Unlabeled WGA-conjugated antibodies were bound to acetyl-glucosamine (GlnAc) beads and incubated with Alexa Fluor® 488-labeled IL-10 as shown in FIG. 6B. Fresh rabbit eyes were scraped 40 times with a 30-gauge needle and incubated for 2 minutes with WGA-conjugated Alexa Fluor 488-labeled IL-1β antibodies as shown in FIG. 6C. The data show that the complexes retain both the affinities for the sugar and antigen recognition by an antibody.

Example 6

Retention of FITC-Labeled WGA in Mice

Figure 7:
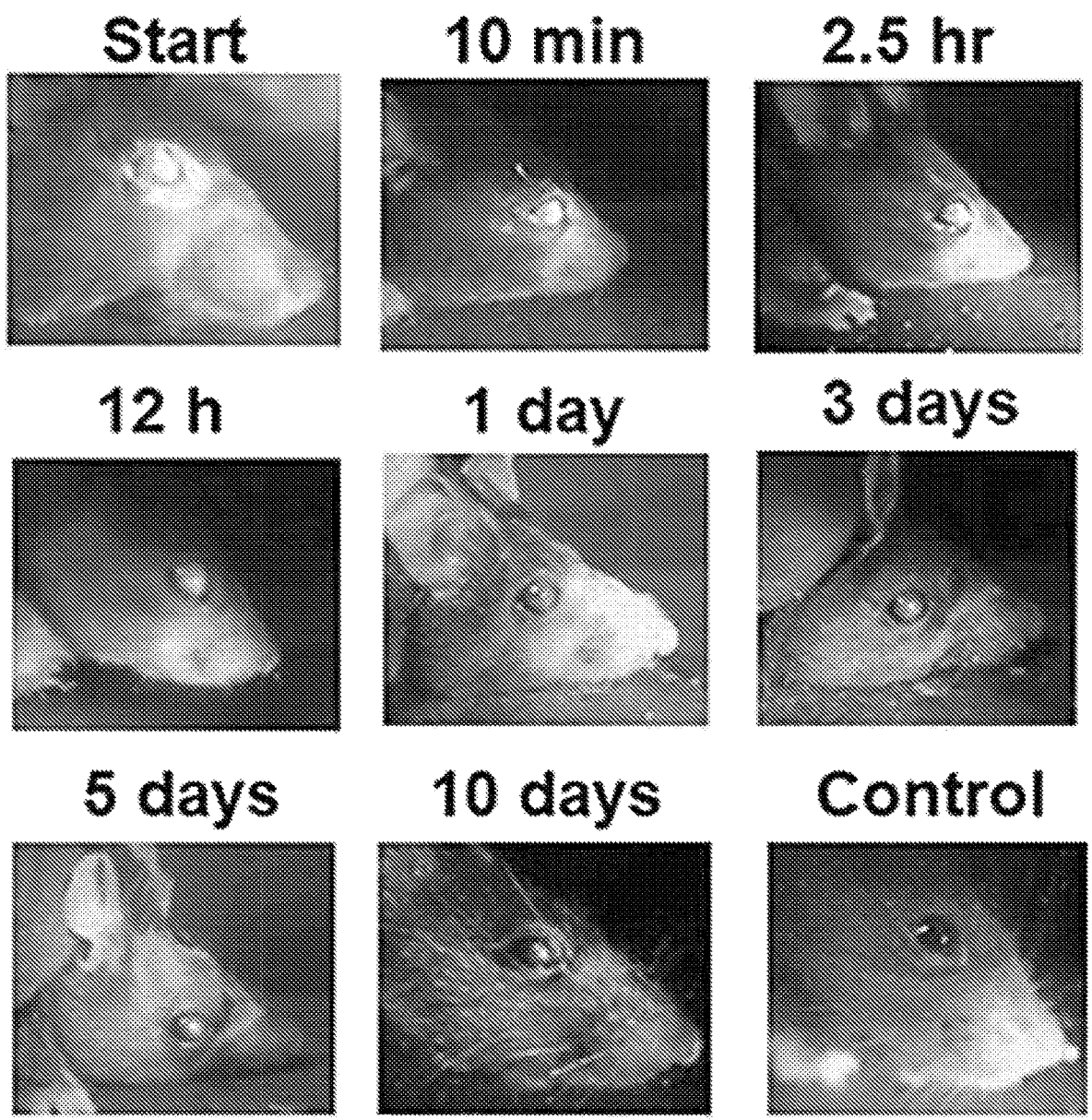
FIG. 7 is a collection of images showing retention of fluorescently-labeled WGA to the eyes of live mice.

Mice were wounded with an Algerbrush. FITC-labeled WGA (Vector Laboratories) was applied to the eyes, which were photographed as shown in FIG. 7. The same mouse is shown at the indicated times. The retention time of fluorescently labeled WGA can be determined using live mice. As shown in FIG. 7, the fluorescence from a single dose of labeled WGA can be followed for at least 5 days. It should be noted that the epithelium covers the wound after 1-2 days in this model, which should aid in containing the drugs.

Example 7

WGA Confers GlcNAc-Binding Activity to Antibodies

Two hundred micrograms of anti-mouse IL-17A antibody (clone TC11-18H10, BD® Biosciences) was transferred to an Amicon® 100 kDa cut-off spin filter, washed two times with 100 µl conjugation buffer (0.1 M HEPES, pH 7.5), and washed once with 2× concentrated conjugation buffer. Alexa Fluor® 488 TFP ester (Invitrogen®) was dissolved in acetone, and 40 µg aliquots were dried down in 0.2 ml PCR tubes (Thermo Scientific™). This labeling reagent was dissolved in the concentrated antibody solution, allowed to react for 6-8 hours at room temperature, and then stored at 4° C. for at least two days before use.

Three hundred twenty microliters of wheat germ agglutinin (Vector Labs) (1 mg/ml) in MES buffer (50 mM MES, 500 mM NaCl, pH 6.0) was activated by adding 20 µl 160 mM EDC (1-ethyl-3-(3-dimethylaminopropyl)carbodiimide hydrochloride) and 20 µl 200 mM sulfo-NHS (N-hydroxysulfosuccinimide). The coupling reagents were removed by three washes with 100 µl MES buffer diluted 10-fold in an Amicon® 10 kDa cut-off spin filter unit. The labeled antibody was divided into two Amicon® 100 kDa cut-off spin filter units, washed three times in conjugation buffer, and concentrated. One hundred microliters of conjugation buffer dried down in Eppendorf tubes was dissolved in the activated WGA to increase the pH, which was added to the antibody in an Amicon units. One hundred microliters of 10-fold diluted MES buffer was added to 100 µl dried conjugation buffer and added to another Amicon unit. They were then incubated for at least 24 hours at 4° C. and washed 3 times with 100 µl HBS (20 mM HEPES, pH 7.2, 100 mM NaCl), and the volume was then adjusted to 100 µl.

Figure 8:
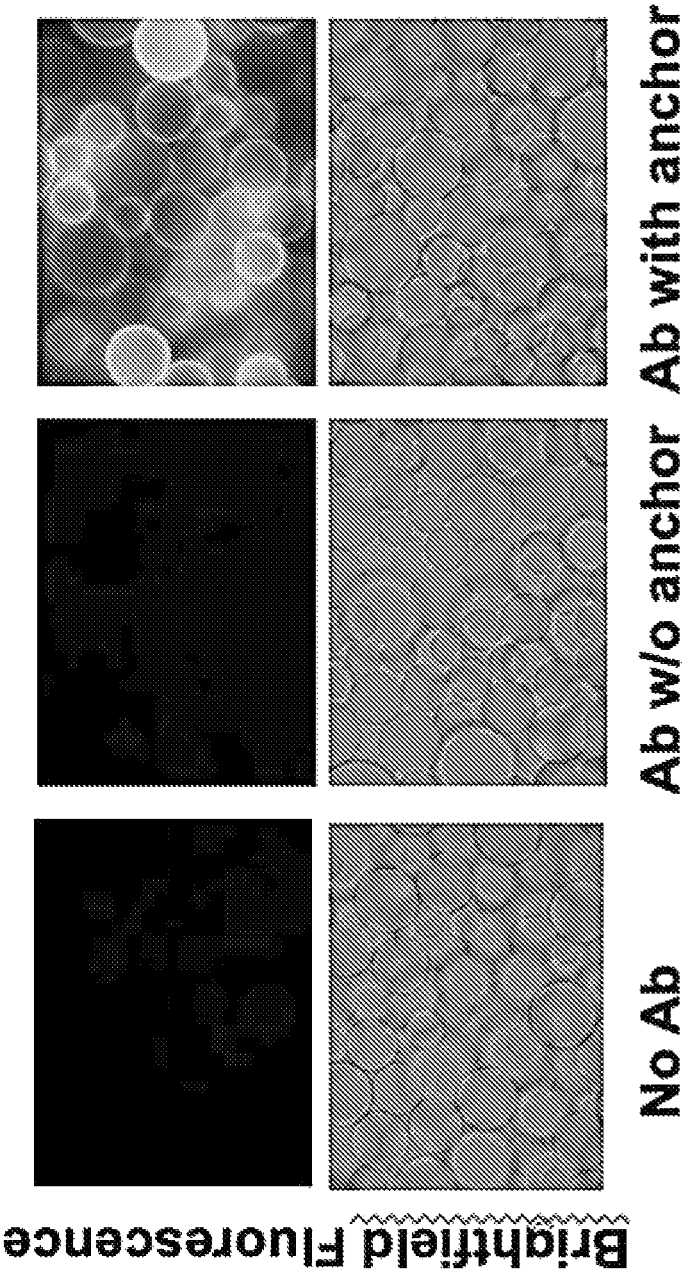
FIG. 8 shows images of fluorescently labeled IL-17A antibody-WGA fusion proteins bound to agarose beads.

To test binding, approximately 10 µl GlcNAc agarose beads (Sigma®) were washed twice with HBS, the supernatant carefully aspirated, and 1 µl of the labeled and conjugated WGA was added, and the tube was placed on a mechanical agitator. After 10 minutes, the beads were washed five times with 200 µl HBS, and an aliquot of the beads was transferred to a microscope slide and photographed with a 20× objective using a fluorescence microscope. The resulting images are shown in FIG. 8.

Example 8

Antibodies Conjugated to WGA Bind to Multiple Tissues

Figure 9:
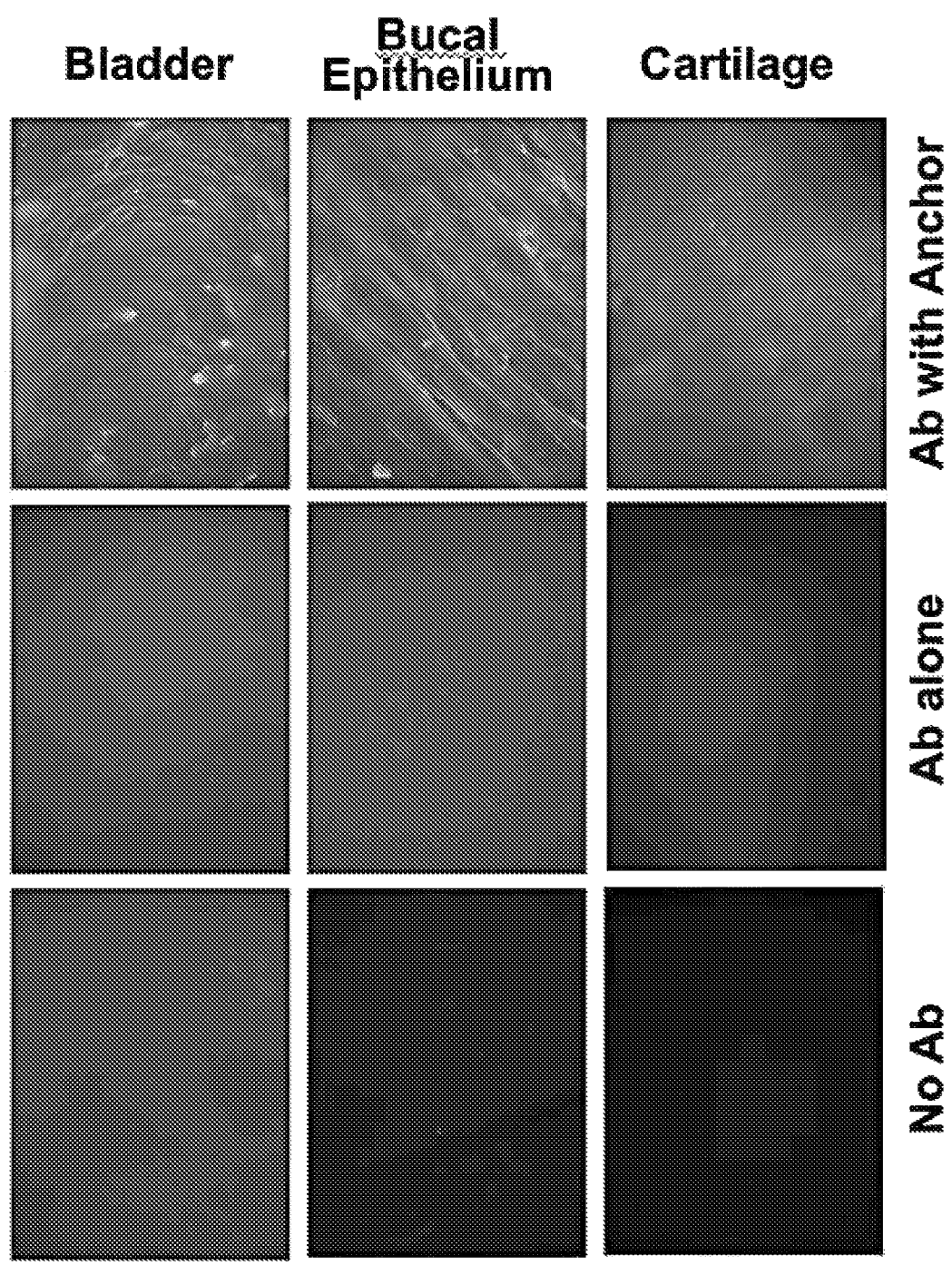
FIG. 9 shows binding of WGA to bladder, buccal epithelium, and cartilage tissues.

New Zealand White rabbits (7-8 weeks old) were euthanized, and the organs were retrieved and dissected. The bladder and buccal epithelium was stretched onto glass microscope slides, and 5 µl of the WGA conjugated and control Alexa Fluor®-labeled antibody was prepared as described in Example 7 and then applied with a 10-minute incubation thereafter. Photographs were collected with a fluorescence microscope using a 20× objective (see, FIG. 9).

Example 9

Antibodies Conjugated to WGA Bind Human Cornea

Figure 10:
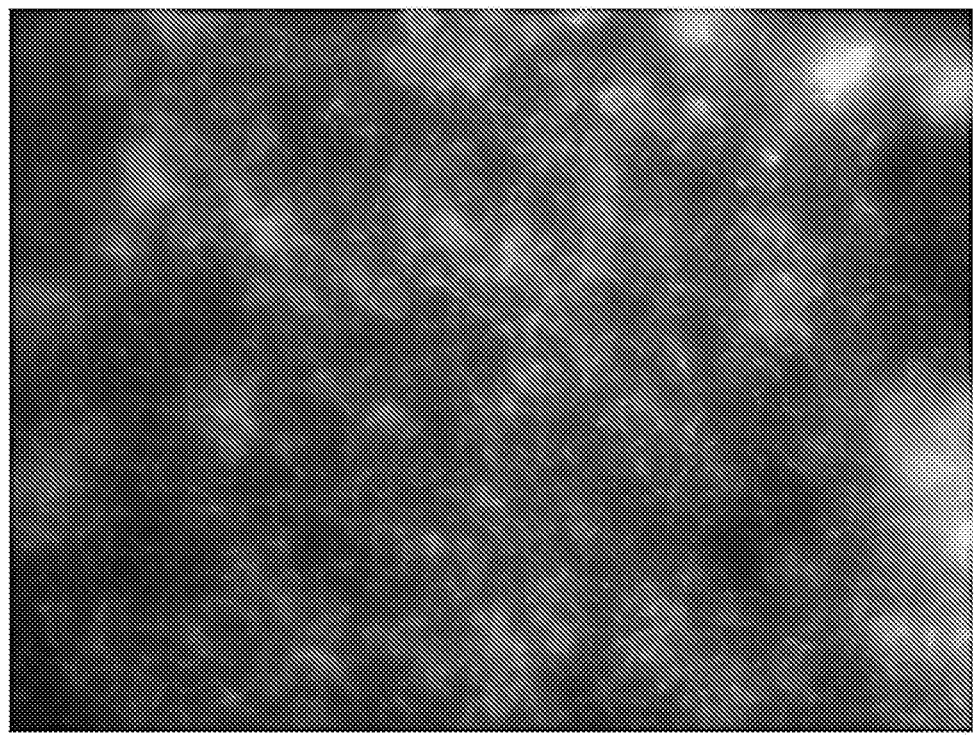
FIG. 10 shows an image of fluorescently labeled WGA-conjugated antibody bound to human cornea.

Outdated human corneas from an eye bank were treated with Alexa Fluor®-labeled antibodies as described in Example 8. Photographs were collected with a 10× objective. FIG. 10 shows an image of fluorescently labeled antibody bound to human cornea.

Example 10

WGA Bind to the Eyes of Mice for at Least 25 Hours In Vivo

Figure 11:
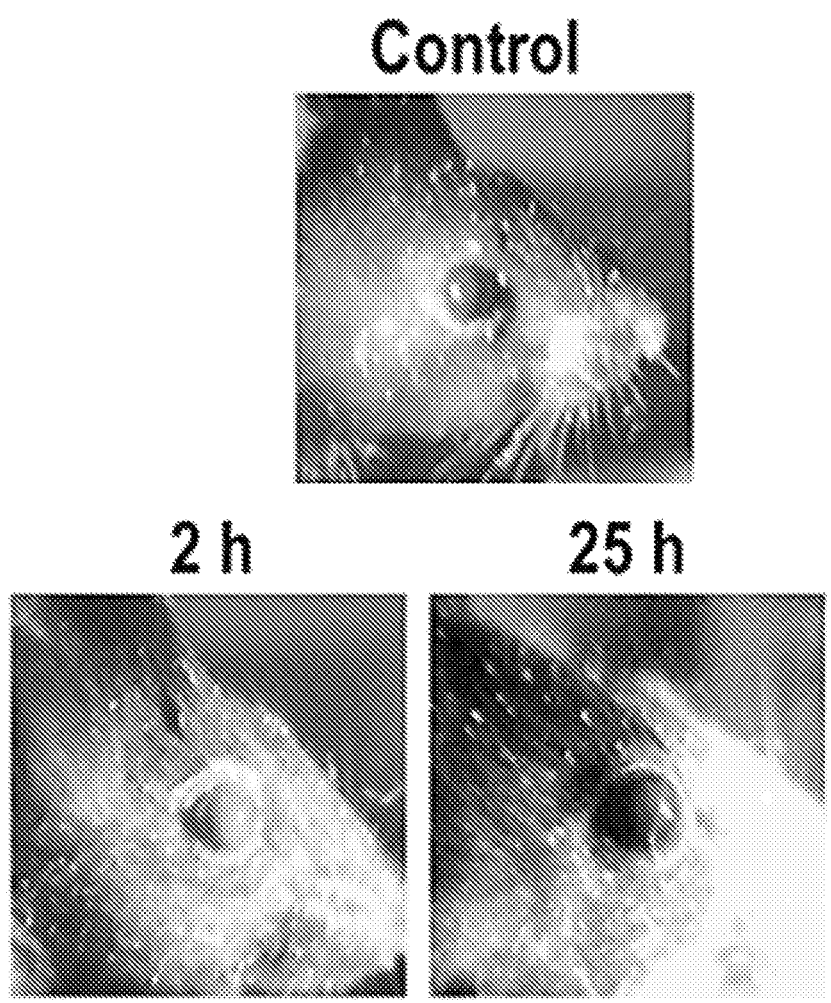
FIG. 11 shows images of a live mouse that had the extraorbital lacrimal glands removed and treated once with fluorescently labeled WGA.

Two hundred microliters of fluorescein-labeled WGA (Vector Labs) was washed in phosphate-buffered saline and concentrated in an Amicon™ 10 kDa cut-off spin filter unit. Next, 0.5 µl was applied to the eyes of 6-8-week-old C57BL/6 mice and photographed with a camera fitted for fluorescent microscopy at the indicated times after application. FIG. 11 shows fluorescence from bound antibodies continuing for up to 25 hours.

Example 11

Antibodies Conjugated to WGA Bind to the Surface of Eyes for at Least 8 Hours

Dry eye was induced by removing the extraorbital lacrimal glands of 6-8-week-oled female-c57BL/6 mice as described (Stevenson, W. et al. (2014), Cornea, 33, 1336-1341). The mice were used two months later. Labeled IL-17A antibodies were produced and conjugated as described in Example 7. These antibodies were applied to the eyes and photographed with a camera fitted for fluorescent photography. FIG. 12A shows that the labeled antibodies were washed out quickly without a WGA anchor, but were retained with an anchor. FIG. 12B shows that the labeled antibody can be detected 8 hours after application when conjugated to a WGA anchor. Antibodies conjugated to WGA bound the surface of the eyes for at least 8 hours, whereas unconjugated antibodies were washed out within 5-15 minutes in a mouse model of dry eye.

Example 12

Antibodies Conjugated to WGA Retain their Ability to Bind Ligands

Unlabeled antibodies were bound to GlcNAc agarose beads as described in Example 7. Ligands were obtained from PeproTech®, dissolved at 100 mg/ml, and labeled in the same way as the antibodies in Example 7. The reactions were quenched by adding ethanolamine to 5 mM, diluted five-fold, and used without further purification by incubation with GlcNAc beads as described in Example 7. FIG. 13A shows beads bound to the indicated antibodies incubated with Alexa Fluor® 488-labeled IL-1β or TGFβ. FIG. 13B shows beads bound to anti-IL-17A antibodies and incubated with Alexa Fluor 488®-labeled IL-17A.

Example 13

An Antibody Against IL-17A Applied Once a Day is Effective at Treating an Inflammatory Condition (Dry Eye) when Conjugated to WGA.

In FIG. 14A, calibration of scores for the dry eye model is shown. Dry eye was induced and photographed as in Example 11. A score of 4 represents severe dry eye, and a score of 1 is very mild disease or disease-free. FIG. 14B shows the effect of treatment of eyes with an anti-IL17A antibody (clone TC11-18H10, BD® Biosciences) without anchor. Application and photography were performed at the same time of day to minimize possible circadian effects. One microgram of the antibodies without anchor was applied daily to the eyes of the mice using a 2 µl pipette where indicated. The baseline is the mean of scores from four sets of photographs taken in the days before application of the therapeutic proteins. Photography was then also performed on days 1, 5, 8, 10, 12, 15, 17, 19, 21, 23, 26, 29, 32, 34, and 36. The intensities of staining were scored by a masked observer. The columns show the means, and error bars indicate the standard errors of measurement. FIG. 14C shows the effect of treating eyes with an antibody that includes the WGA anchor. These experiments were performed in parallel to the measurements in B, and the columns represent the observed reduction in scores (the scores of mice treated with an antibody without that anchor minus the scores of eyes treated with the antibody with a WGA anchor). The numbers are p values comparing the two groups each day (with and without anchor) using the double-tailed Student's t test. Decreases in staining were observed after 8-12 days of treatment, which was reversed 5-10 days after termination of treatment.

In view of the many possible embodiments to which the principles of the disclosed invention may be applied, it should be recognized that the illustrated embodiments are only examples of the invention and should not be taken as limiting the scope of the invention. We, therefore, claim as our invention all that comes within the scope and spirit of these claims.

We claim:

1. A fusion protein comprising an anchor domain and a therapeutic polypeptide, wherein
   - the anchor domain comprises a wheat germ agglutinin (WGA) anchor domain, and
   - the therapeutic polypeptide comprises
     - an antibody that specifically binds to, and is an antagonist of, interleukin (IL)-17A.

2. The fusion protein of claim 1, wherein:
   - the WGA anchor binding domain comprises the amino acid sequence of SEQ ID NO: 7.

3. The fusion protein of claim 1, further comprising a linker between the anchor binding domain and the therapeutic domain.

4. The fusion protein of claim 3, wherein linker has the amino acid sequence of SEQ ID NO:9 or SEQ ID NO: 19.

5. The fusion protein of claim 1, further comprising a label, solubility enhancing sequence, purification tag, or combinations thereof.

6. The fusion protein of claim 1, wherein the anchor domain, therapeutic peptide or combination thereof are benzylated, glycosylated, acetylated, phosphorylated, amidated, pegylated, and combinations thereof.

7. A method for treating an inflammation of tissue in a subject, comprising administering to the tissue of the subject a therapeutically effective amount of the fusion protein of claim 1 thereby treating the inflammation of the tissue in the subject.

8. The method of claim 7, wherein the tissue is in a mouth, a bladder, a nasal cavity, a gastrointestinal tract, a lung, a joint, an eye, or the reproductive system of a subject.

9. A pharmaceutical composition comprising a therapeutically effective amount of the fusion protein of claim 1 and a pharmaceutically acceptable carrier formulated for external and/or topical administration to a tissue.

10. A unit dose dispenser comprising the pharmaceutical composition claim 9.

11. The pharmaceutical composition of claim 9, wherein the pharmaceutical composition is formulated as a gel, cream, lotion, or ointment.

12. A method for treating an inflammation of an eye in a subject, comprising administering to the eye of the subject a therapeutically effective amount of the fusion protein of claim 1, thereby treating the inflammation of the eye in the subject.

13. The method of claim 12, wherein the subject has dry eye.

14. The method of claim 12, wherein the subject has Sjögren's syndrome.

* * * * *

SEQUENCE LISTING

<160> NUMBER OF SEQ ID NOS: 26

<210> SEQ ID NO 1
<211> LENGTH: 10

```
<212> TYPE: PRT
<213> ORGANISM: Artificial Sequence
<220> FEATURE:
<223> OTHER INFORMATION: vWF polypeptide

<400> SEQUENCE: 1

Trp Arg Glu Pro Ser Phe Met Ala Leu Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: vWF polypeptide

<400> SEQUENCE: 2

Trp Arg Glu Pro Ser Phe Cys Ala Leu Ser
1               5                   10

<210> SEQ ID NO 3
<211> LENGTH: 215
<212> TYPE: PRT
<213> ORGANISM: Artificial Sequence
<220> FEATURE:
<223> OTHER INFORMATION: Clostridium polypeptide

<400> SEQUENCE: 3

Glu Ile Lys Asp Leu Ser Glu Asn Lys Leu Pro Val Ile Tyr Met His
1               5                   10                  15

Val Pro Lys Ser Gly Ala Leu Asn Gln Lys Val Val Phe Tyr Gly Lys
            20                  25                  30

Gly Thr Tyr Asp Pro Asp Gly Ser Ile Ala Gly Tyr Gln Trp Asp Phe
        35                  40                  45

Gly Asp Gly Ser Asp Phe Ser Ser Glu Gln Asn Pro Ser His Val Tyr
    50                  55                  60

Thr Lys Lys Gly Glu Tyr Thr Val Thr Leu Arg Val Met Asp Ser Ser
65                  70                  75                  80

Gly Gln Met Ser Glu Lys Thr Met Lys Ile Lys Ile Thr Asp Pro Val
                85                  90                  95

Tyr Pro Ile Gly Thr Glu Lys Glu Pro Asn Asn Ser Lys Glu Thr Ala
            100                 105                 110

Ser Gly Pro Ile Val Pro Gly Ile Pro Val Ser Gly Thr Ile Glu Asn
        115                 120                 125

Thr Ser Asp Gln Asp Tyr Phe Tyr Phe Asp Val Ile Thr Pro Gly Glu
    130                 135                 140

Val Lys Ile Asp Ile Asn Lys Leu Gly Tyr Gly Gly Ala Thr Trp Val
145                 150                 155                 160

Val Tyr Asp Glu Asn Asn Asn Ala Val Ser Tyr Ala Thr Asp Asp Gly
                165                 170                 175

Gln Asn Leu Ser Gly Lys Phe Lys Ala Asp Lys Pro Gly Arg Tyr Tyr
            180                 185                 190

Ile His Leu Tyr Met Phe Asn Gly Ser Tyr Met Pro Tyr Arg Ile Asn
        195                 200                 205

Ile Glu Gly Ser Val Gly Arg
    210                 215

<210> SEQ ID NO 4
<211> LENGTH: 21
<212> TYPE: PRT
```

```
<213> ORGANISM: Artificial Sequence
<220> FEATURE:
<223> OTHER INFORMATION: HS-binding polypeptide

<400> SEQUENCE: 4

Lys Arg Lys Lys Lys Gly Lys Gly Leu Gly Lys Lys Arg Asp Pro Ser
1               5                   10                  15

Leu Arg Lys Tyr Lys
            20

<210> SEQ ID NO 5
<211> LENGTH: 21
<212> TYPE: PRT
<213> ORGANISM: Artificial Sequence
<220> FEATURE:
<223> OTHER INFORMATION: HS-binding polypeptide

<400> SEQUENCE: 5

Lys Arg Lys Lys Lys Gly Lys Gly Leu Gly Lys Lys Arg Asp Pro Cys
1               5                   10                  15

Leu Arg Lys Tyr Lys
            20

<210> SEQ ID NO 6
<211> LENGTH: 290
<212> TYPE: PRT
<213> ORGANISM: Artificial Sequence
<220> FEATURE:
<223> OTHER INFORMATION: ConA polypeptide

<400> SEQUENCE: 6

Met Ala Ile Ser Lys Lys Ser Ser Leu Phe Leu Pro Ile Phe Thr Phe
1               5                   10                  15

Ile Thr Met Phe Leu Met Val Val Asn Lys Val Ser Ser Ser Thr His
            20                  25                  30

Glu Thr Asn Ala Leu His Phe Met Phe Asn Gln Phe Ser Lys Asp Gln
        35                  40                  45

Lys Asp Leu Ile Leu Gln Gly Asp Ala Thr Thr Gly Thr Asp Gly Asn
    50                  55                  60

Leu Glu Leu Thr Arg Val Ser Ser Asn Gly Ser Pro Gln Gly Ser Ser
65                  70                  75                  80

Val Gly Arg Ala Leu Phe Tyr Ala Pro Val His Ile Trp Glu Ser Ser
                85                  90                  95

Ala Val Val Ala Ser Phe Glu Ala Thr Phe Thr Phe Leu Ile Lys Ser
            100                 105                 110

Pro Asp Ser His Pro Ala Asp Gly Ile Ala Phe Phe Ile Ser Asn Ile
        115                 120                 125

Asp Ser Ser Ile Pro Ser Gly Ser Thr Gly Arg Leu Leu Gly Leu Phe
    130                 135                 140

Pro Asp Ala Asn Val Ile Arg Asn Ser Thr Thr Ile Asp Phe Asn Ala
145                 150                 155                 160

Ala Tyr Asn Ala Asp Thr Ile Val Ala Val Glu Leu Asp Thr Tyr Pro
                165                 170                 175

Asn Thr Asp Ile Gly Asp Pro Ser Tyr Pro His Ile Gly Ile Asp Ile
            180                 185                 190

Lys Ser Val Arg Ser Lys Lys Thr Ala Lys Trp Asn Met Gln Asn Gly
        195                 200                 205

Lys Val Gly Thr Ala His Ile Ile Tyr Asn Ser Val Asp Lys Arg Leu
    210                 215                 220
```

Ser Ala Val Val Ser Tyr Pro Asn Ala Asp Ser Ala Thr Val Ser Tyr
225                 230                 235                 240

Asp Val Asp Leu Asp Asn Val Leu Pro Glu Trp Val Arg Val Gly Leu
            245                 250                 255

Ser Ala Ser Thr Gly Leu Tyr Lys Glu Thr Asn Thr Ile Leu Ser Trp
        260                 265                 270

Ser Phe Thr Ser Lys Leu Lys Ser Asn Glu Ile Pro Asp Ile Ala Thr
    275                 280                 285

Val Val
    290

<210> SEQ ID NO 7
<211> LENGTH: 212
<212> TYPE: PRT
<213> ORGANISM: Artificial Sequence
<220> FEATURE:
<223> OTHER INFORMATION: WGA polypeptide

<400> SEQUENCE: 7

Met Lys Met Met Ser Thr Arg Ala Leu Ala Leu Gly Ala Ala Ala Val
1               5                   10                  15

Leu Ala Phe Ala Ala Thr Ala Gln Ala Gln Arg Cys Gly Glu Gln
            20                  25                  30

Gly Ser Asn Met Glu Cys Pro Asn Asn Leu Cys Cys Ser Gln Tyr Gly
        35                  40                  45

Tyr Cys Gly Met Gly Gly Asp Tyr Cys Gly Lys Gly Cys Gln Asn Gly
    50                  55                  60

Ala Cys Trp Thr Ser Lys Arg Cys Gly Ser Gln Ala Gly Gly Ala Thr
65                  70                  75                  80

Cys Thr Asn Asn Gln Cys Cys Ser Gln Tyr Gly Tyr Cys Gly Phe Gly
                85                  90                  95

Ala Glu Tyr Cys Gly Ala Gly Cys Gln Gly Gly Pro Cys Arg Ala Asp
                100                 105                 110

Ile Lys Cys Gly Ser Gln Ala Gly Gly Lys Leu Cys Pro Asn Asn Leu
            115                 120                 125

Cys Cys Ser Gln Trp Gly Phe Cys Gly Leu Gly Ser Glu Phe Cys Gly
        130                 135                 140

Gly Gly Cys Gln Ser Gly Ala Cys Ser Thr Asp Lys Pro Cys Gly Lys
145                 150                 155                 160

Asp Ala Gly Gly Arg Val Cys Thr Asn Asn Tyr Cys Cys Ser Lys Trp
                165                 170                 175

Gly Ser Cys Gly Ile Gly Pro Gly Tyr Cys Gly Ala Gly Cys Gln Ser
            180                 185                 190

Gly Gly Cys Asp Gly Val Phe Ala Glu Ala Ile Thr Ala Asn Ser Thr
        195                 200                 205

Leu Leu Gln Glu
    210

<210> SEQ ID NO 8
<211> LENGTH: 217
<212> TYPE: PRT
<213> ORGANISM: Artificial Sequence
<220> FEATURE:
<223> OTHER INFORMATION: Jac polypeptide

<400> SEQUENCE: 8

Met Ala Tyr Ser Ser Leu Leu Ser Leu Ser Val Leu Ala Leu Leu Phe

```
               1               5                  10                 15
            Ser Ile Ser Ser Ala Asp Thr Arg Lys Trp Phe Leu Ala Asn Gly Ile
                           20                  25                  30

Asn Gln Asn Pro Ile Gly Ile Ile Glu Ala Ala Val Gly Val Ser Glu
                           35                  40                  45

Asp Leu Leu Asn Leu Asn Gly Met Glu Ala Lys Asn Asp Glu Gln Ser
                50                  55                  60

Gly Ile Ser Gln Thr Val Ile Val Gly Pro Trp Gly Ala Lys Val Ser
             65                  70                  75                  80

Thr Ser Ser Asn Gly Lys Ala Phe Asp Asp Gly Ala Phe Thr Gly Ile
                               85                  90                  95

Arg Glu Ile Asn Leu Ser Tyr Asn Lys Glu Thr Ala Ile Gly Asp Phe
                           100                 105                 110

Gln Val Val Tyr Asp Leu Asn Gly Ser Pro Tyr Val Gln Asn His
                           115                 120                 125

Lys Ser Phe Ile Thr Gly Phe Thr Pro Val Lys Ile Ser Leu Asp Phe
                           130                 135                 140

Pro Ser Glu Tyr Ile Met Glu Val Ser Gly Tyr Thr Gly Asn Val Ser
            145                 150                 155                 160

Gly Tyr Val Val Val Arg Ser Leu Thr Phe Lys Thr Asn Lys Lys Thr
                               165                 170                 175

Tyr Gly Pro Tyr Gly Val Thr Ser Gly Thr Pro Phe Asn Leu Pro Ile
                           180                 185                 190

Glu Asn Gly Leu Ile Val Gly Phe Lys Gly Ser Ile Gly Tyr Trp Leu
                           195                 200                 205

Asp Tyr Phe Ser Met Tyr Leu Ser Leu
                           210                 215

<210> SEQ ID NO 9
<211> LENGTH: 5
<212> TYPE: PRT
<213> ORGANISM: Artificial Sequence
<220> FEATURE:
<223> OTHER INFORMATION: linker

<400> SEQUENCE: 9

Gly Gly Gly Gly Ser
1               5

<210> SEQ ID NO 10
<211> LENGTH: 116
<212> TYPE: PRT
<213> ORGANISM: Artificial Sequence
<220> FEATURE:
<223> OTHER INFORMATION: Ig-binding polypeptide

<400> SEQUENCE: 10

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Ala Asp Asn Lys Phe Asn
        50                  55                  60

Lys Glu Gln Gln Asn Ala Phe Tyr Glu Ile Leu His Leu Pro Asn Leu
65                  70                  75                  80
```

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys
        115

<210> SEQ ID NO 11
<211> LENGTH: 77
<212> TYPE: PRT
<213> ORGANISM: Artificial Sequence
<220> FEATURE:
<223> OTHER INFORMATION: Ig-binding polypeptide

<400> SEQUENCE: 11

Lys Thr Phe Thr Val Thr Glu Lys Pro Glu Val Ile Asp Ala Ser Glu
1               5                   10                  15

Leu Thr Pro Ala Val Thr Thr Tyr Lys Leu Val Ile Asn Gly Lys Thr
            20                  25                  30

Leu Lys Gly Glu Thr Thr Thr Lys Ala Val Asp Ala Glu Thr Ala Glu
        35                  40                  45

Lys Ala Phe Lys Gln Tyr Ala Asn Asp Asn Gly Val Asp Gly Val Trp
    50                  55                  60

Thr Tyr Asp Asp Ala Thr Lys Thr Phe Thr Val Thr Glu
65                  70                  75

<210> SEQ ID NO 12
<211> LENGTH: 161
<212> TYPE: PRT
<213> ORGANISM: Artificial Sequence
<220> FEATURE:
<223> OTHER INFORMATION: TNF receptor 1 polypeptide

<400> SEQUENCE: 12

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn

<210> SEQ ID NO 13
<211> LENGTH: 14

```
<212> TYPE: PRT
<213> ORGANISM: Artificial Sequence
<220> FEATURE:
<223> OTHER INFORMATION: P144 polypeptide

<400> SEQUENCE: 13

Thr Ser Leu Asp Ala Ser Ile Ile Trp Ala Met Met Gln Asn
1               5                   10

<210> SEQ ID NO 14
<211> LENGTH: 15
<212> TYPE: PRT
<213> ORGANISM: Artificial Sequence
<220> FEATURE:
<223> OTHER INFORMATION: P17 polypeptide

<400> SEQUENCE: 14

Lys Arg Ile Trp Phe Ile Pro Arg Ser Ser Trp Tyr Glu Arg Ala
1               5                   10                  15

<210> SEQ ID NO 15
<211> LENGTH: 176
<212> TYPE: PRT
<213> ORGANISM: Artificial Sequence
<220> FEATURE:
<223> OTHER INFORMATION: Exemplary fusion protein

<400> SEQUENCE: 15

Met Trp Arg Glu Pro Ser Phe Met Ala Leu Ser Ala Ser Gly Gly Gly
1               5                   10                  15

Gly Ser Gly Gly Gly Gly Ser Ala Ser Met Gly Thr Pro Ala Val Thr
                20                  25                  30

Thr Tyr Lys Leu Val Ile Asn Gly Lys Thr Leu Lys Gly Glu Thr Thr
            35                  40                  45

Thr Lys Ala Val Asp Ala Glu Thr Ala Glu Lys Ala Phe Lys Gln Tyr
        50                  55                  60

Ala Asn Asp Asn Gly Val Asp Gly Val Trp Thr Tyr Asp Asp Ala Thr
65                  70                  75                  80

Lys Thr Phe Thr Val Thr Glu Val Asn Thr Pro Ala Val Thr Thr Tyr
                85                  90                  95

Lys Leu Val Ile Asn Gly Lys Thr Leu Lys Gly Glu Thr Thr Thr Lys
            100                 105                 110

Ala Val Asp Ala Glu Thr Ala Glu Lys Ala Phe Lys Gln Tyr Ala Asn
        115                 120                 125

Asp Asn Gly Val Asp Gly Val Trp Thr Tyr Asp Asp Ala Thr Lys Thr
    130                 135                 140

Phe Thr Val Thr Glu Ile Gly Glu Asn Leu Tyr Phe Gln Gly Ile Asp
145                 150                 155                 160

Glu Asn Leu Tyr Phe Gln Gly Gly Ser His His His His His His
                165                 170                 175

<210> SEQ ID NO 16
<211> LENGTH: 186
<212> TYPE: PRT
<213> ORGANISM: Artificial Sequence
<220> FEATURE:
<223> OTHER INFORMATION: Exemplary fusion protein

<400> SEQUENCE: 16

Met Ser Lys Lys His His His His His His His Gly Gly Gly Gly
1               5                   10                  15
```

```
Ser Ala Ser Met Gly Thr Pro Ala Val Thr Thr Tyr Lys Leu Val Ile
            20                  25                  30

Asn Gly Lys Thr Leu Lys Gly Glu Thr Thr Thr Lys Ala Val Asp Ala
        35                  40                  45

Glu Thr Ala Glu Lys Ala Phe Lys Gln Tyr Ala Asn Asp Asn Gly Val
50                  55                  60

Asp Gly Val Trp Thr Tyr Asp Asp Ala Thr Lys Thr Phe Thr Val Thr
65                  70                  75                  80

Glu Val Asn Thr Pro Ala Val Thr Thr Tyr Lys Leu Val Ile Asn Gly
                85                  90                  95

Lys Thr Leu Lys Gly Glu Thr Thr Thr Lys Ala Val Asp Ala Glu Thr
            100                 105                 110

Ala Glu Lys Ala Phe Lys Gln Tyr Ala Asn Asp Asn Gly Val Asp Gly
        115                 120                 125

Val Trp Thr Tyr Asp Asp Ala Thr Lys Thr Phe Thr Val Thr Glu Ile
130                 135                 140

Gly Glu Asn Leu Tyr Phe Gln Gly Ile Asp Glu Asn Leu Tyr Phe Gln
145                 150                 155                 160

Gly Gly Ser Ala Gly Gly Gly Ser Gly Gly Gly Ser Ala Ser
                165                 170                 175

Trp Arg Glu Pro Ser Phe Met Ala Leu Ser
            180                 185

<210> SEQ ID NO 17
<211> LENGTH: 82
<212> TYPE: PRT
<213> ORGANISM: Artificial Sequence
<220> FEATURE:
<223> OTHER INFORMATION: Exemplary fusion protein

<400> SEQUENCE: 17

Met Ser Lys Lys Trp Arg Glu Pro Ser Phe Met Ala Leu Ser Ala Ser
1               5                   10                  15

Gly Gly Gly Gly Ser Gly Gly Gly Ser Glu Ala Ala Lys Thr
            20                  25                  30

Ser Leu Asp Ala Ser Ile Ile Trp Ala Met Met Gln Asn Glu Ala Ala
        35                  40                  45

Ala Lys Glu Ala Ala Ala Lys Thr Ser Leu Asp Ala Ser Ile Ile Trp
50                  55                  60

Ala Met Met Gln Asn Gly Gly Gly Ser His His His His His
65                  70                  75                  80

His His

<210> SEQ ID NO 18
<211> LENGTH: 84
<212> TYPE: PRT
<213> ORGANISM: Artificial Sequence
<220> FEATURE:
<223> OTHER INFORMATION: Exemplary fusion protein

<400> SEQUENCE: 18

Met Ser Lys Lys Trp Arg Glu Pro Ser Phe Met Ala Leu Ser Ala Ser
1               5                   10                  15

Gly Gly Gly Gly Ser Gly Gly Gly Ser Gly Gly Gly Ser Lys
            20                  25                  30

Arg Ile Trp Phe Ile Pro Arg Ser Ser Trp Tyr Glu Arg Ala Gly Gly
        35                  40                  45
```

-continued

```
Gly Gly Ser Gly Gly Gly Ser Lys Arg Ile Trp Phe Ile Pro Arg
    50              55                  60
Ser Ser Trp Tyr Glu Arg Ala Gly Gly Gly Ser His His His His
65                  70                  75                  80
His His His His

<210> SEQ ID NO 19
<211> LENGTH: 10
<212> TYPE: PRT
<213> ORGANISM: Artificial Sequence
<220> FEATURE:
<223> OTHER INFORMATION: linker

<400> SEQUENCE: 19

Glu Ala Ala Ala Lys Glu Ala Ala Ala Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 20

Tyr Arg Glu Pro Ser Phe Met Ala Leu Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 21

Trp Lys Glu Pro Ser Phe Met Ala Leu Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 22

Trp Arg Asp Pro Ser Phe Met Ala Leu Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 23

Trp Arg Glu Ala Ser Phe Met Ala Leu Ser
1               5                   10

<210> SEQ ID NO 24
```

-continued

```
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 24

Trp Arg Glu Pro Thr Phe Met Ala Leu Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 25

Trp Arg Glu Pro Ser Tyr Met Ala Leu Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Collagen-binding anchor domain from the von
      Willebrand factor

<400> SEQUENCE: 26

Trp Arg Glu Pro Ser Phe Ala Ala Leu Ser
1               5                   10
```